(12) United States Patent
Tsaklakidis et al.

(10) Patent No.: US 8,129,373 B2
(45) Date of Patent: Mar. 6, 2012

(54) CARBONYL COMPOUNDS

(75) Inventors: Christos Tsaklakidis, Weinheim (DE); Dieter Dorsch, Ober-Ramstadt (DE); Werner Mederski, Zwingenberg (DE); Bertram Cezanne, Mörfelden-Walldorf (DE); Johannes Gleitz, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 12/817,314

(22) Filed: Jun. 17, 2010

(65) Prior Publication Data

US 2010/0256131 A1 Oct. 7, 2010

Related U.S. Application Data

(62) Division of application No. 10/551,557, filed as application No. PCT/EP2004/002350 on Mar. 8, 2004, now Pat. No. 7,906,516.

(60) Provisional application No. 60/483,897, filed on Jul. 2, 2003.

(30) Foreign Application Priority Data

Apr. 3, 2003 (DE) .................. 103 15 377
Jun. 30, 2003 (DE) .................. 103 29 295

(51) Int. Cl.

| A61K 31/5377 | (2006.01) |
| A61K 31/4439 | (2006.01) |
| A61K 31/497 | (2006.01) |
| A61K 31/444 | (2006.01) |
| A61P 29/00 | (2006.01) |
| A61P 7/02 | (2006.01) |
| A61P 9/10 | (2006.01) |
| A61P 25/06 | (2006.01) |
| A61P 35/00 | (2006.01) |
| A61P 35/04 | (2006.01) |

(52) U.S. Cl. ............... 514/230.8; 514/255.05; 514/333; 514/340; 514/342; 546/278.7; 548/215

(58) Field of Classification Search .................. None
See application file for complete search history.

(56) References Cited

U.S. PATENT DOCUMENTS

| 5,705,487 | A | 1/1998 | Schacht |
| 6,635,657 | B1 | 10/2003 | Beight |
| 6,673,817 | B1 | 1/2004 | Zhu |
| 2002/0002183 | A1 | 1/2002 | Zhu |
| 2002/0055469 | A1 | 5/2002 | Pastor |
| 2003/0162787 | A1 | 8/2003 | Bigge |
| 2004/0010017 | A1 | 1/2004 | Beight |
| 2004/0038858 | A1 | 2/2004 | Dorsch |
| 2004/0087582 | A1 | 5/2004 | Dorsch |
| 2004/0097547 | A1 | 5/2004 | Taveras |
| 2004/0097550 | A1 | 5/2004 | Mederski |

FOREIGN PATENT DOCUMENTS

| GB | 1503244 | 3/1978 |
| WO | WO 9523609 | 9/1995 |
| WO | WO 0039118 | 7/2000 |
| WO | WO 0071516 | 11/2000 |
| WO | WO 0164642 | 9/2001 |
| WO | WO 0214308 | 2/2002 |
| WO | WO 0222575 | 3/2002 |
| WO | WO 0248099 | 6/2002 |
| WO | WO 02057236 | 7/2002 |
| WO | WO 02074735 | 9/2002 |
| WO | WO 02083624 | 10/2002 |
| WO | WO 03045912 | 6/2003 |
| WO | WO 03050088 | 6/2003 |

OTHER PUBLICATIONS

Pharmacyclics, http://www.wikinvest.com/stock/Pharmacyclics_(PCYC)/Pharmacyclics_Announces_Completion_Phase_Clinical_Trial_Factor_Viia (2008).*
Agnelli et al., Circulation, 2011, 9 pages.*
Tumor, 2011, http://health.nytimes.com/health/guides/disease/tumor/overview.html.*
Chawla et al., "Challenges in Polymorphism of Pharmaceuticals", CRIPS vol. 5, No. 1, Jan.-Mar. 2004 (4 Pages.*
Newman et al., "Solid-state analysis of the active pharmaceutical ingredient in drug products", DDT vol. 8, No. 19, Oct. 2003, p. 898-905.*
Bigge et al., caplus an 2003:434528.*
Database Beilstein Beilstein Insitute for Organic Chemistry, Frankfurt-Main, DE Aug. 9, 1996, XP002283422.
Database Beilsten Beilstein Institute for Organic Chemistry, Frankfurt-Main, DE; Jun. 27, 1988 XP002282645.
Database Beilstein Beilstein Institute fro Organic Chemistry, Frankfurt-Main, DE Jun. 27, 1988 XP002282646.
Database Beilstein Beilstein Institute for Organic Chemistry, Frankfurt-Main, DE Mar. 19, 1991, XP002282647.
Griesser, U.L., "The Importance of Solvates", Polymorphism: in the Pharmaceutical industry, Edited by Rolf Hilfiker, Copyright 2006 Wiley-VCH Verlag GmbH & Co. KgaA, Weinhelm ISBN: 3-527-31146-7, pp. 211-233.
Vippagunta, S. R., et al., "Crystalline Solids", Advanced Drug Delivery Reviews, 48 (2001) 3-26.
Madhusudan et al., Clinical Biochemistry 37:618-635 (2004).
Chawla et al., "Challenges in Polymorphism of Pharmaceuticals" CRIPS, 5(1), Jan.-Mar. 2004.
Newman et al., "Solid-state analysis of the active pharmaceutical ingredient in drug products" DDT, 8(19):898-905, Oct. 2003.
Hacks Chemical Dictionary, Fourth Edition, Julius Grant, p. 203 (1972).

* cited by examiner

Primary Examiner — Sun Jae Loewe
(74) Attorney, Agent, or Firm — Millen, White, Zelano & Branigan, P.C.

(57) ABSTRACT

Novel compounds of the formula (I), in which D, E, G, W, X, Y, T, $R^1$ and $R^2$ are as defined in Patent Claim 1, are inhibitors of coagulation factor Xa and can be employed for the prophylaxis and/or therapy of thromboembolic diseases and for the treatment of tumors.

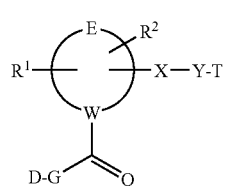

43 Claims, No Drawings

CARBONYL COMPOUNDS

This is a divisional of U.S. application Ser. No. 10/551,557, filed Oct. 3, 2005 now U.S. Pat. No. 7,906,516, which is the U.S. National Phase Application under 35 USC 371 of International Application No. PCT/EP2004/002350, filed on Mar. 8, 2004, which claims priority to U.S. application Ser. No. 60/483,897, filed Jul. 2, 2003.

This application claims the benefit of priority to U.S. application Ser. No. 60/483,897, filed Jul. 2, 2003.

The invention relates to compounds of the formula I

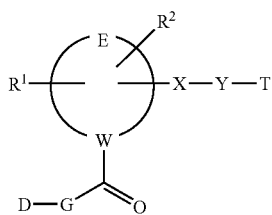

in which
$R^1, R^2$ are each, independently of one another, H, =O, Hal, A, ethynyl, $OR^3$, $N(R^3)_2$, $NO_2$, CN, $N_3$, $COOR^3$, $CON(R^3)_2$, $—[C(R^4)_2]_n$—Ar, $—[C(R^4)_2]_n$-Het, $—[C(R^4)_2]_n$-cycloalkyl, $—OCOR^3$, $NR^3COA$ or $NR^3SO_2A$, $R^1$ and $R^2$ together are alternatively a bicyclically or spirocyclically bonded 3- to 7-membered carbocyclic or heterocyclic ring having from 0 to 3 N, O and/or S atoms, $R^3$ is H, A, H—C≡C—$CH_2$—, $CH_3$—C≡C—$CH_2$—, —$CH_2$—CH(OH)—$CH_2OH$, —$CH_2$—CH(OH)—$CH_2NH_2$, —$CH_2$—CH(OH)—$CH_2$Het', $—[C(R^4)_2]_n$—Ar', $—[C(R^4)_2]_n$-Het', $—[C(R^4)_2]_n$-cycloalkyl, $—[C(R^4)_2]_n$—COOA or $—[C(R^4)_2]_n N(R^4)_2$, $R^4$ is H or A, W is N, $CR^3$ or an $sp^2$-hybridised carbon atom, E together with W is a 3- to 7-membered saturated carbocyclic or heterocyclic ring having from 0 to 3 N, from 0 to 2 O and/or from 0 to 2 S atoms, which may contain a double bond, D is a monocyclic or bicyclic, aromatic carbocyclic or heterocyclic ring having from 0 to 4 N, O and/or S atoms which is unsubstituted or monosubstituted or polysubstituted by Hal, A, $OR^3$, $N(R^3)_2$, $NO_2$, CN, $COOR^3$ or $CON(R^3)_2$, G is $—[C(R^4)_2]_n$—, $—[C(R^4)_2]_n NR^3$—, $—[C(R^4)_2]_n O$—, $—[C(R^4)_2]_n S$— or $—[C(R^4)=C(R^4)]_n$—, X is $—[C(R^4)_2]_n CONR^3[C(R^4)_2]_n$—, $—[C(R^4)_2]_n NR^3 CO[C(R^4)_2]_n$—, $—[C(R^4)_2]_n NR^3[C(R^4)_2]_n$—, $—[C(R^4)_2]_n O[C(R^4)_2]_n$—, $—[C(R^4)_2]_n CO[C(R^4)_2]_n$— or $—[C(R^4)_2]_n COO[C(R^4)_2]_n$—, Y is alkylene, cycloalkylene, Het-diyl or Ar-diyl, T is a monocyclic or bicyclic, saturated or unsaturated carbocyclic or heterocyclic ring having from 0 to 4 N, O and/or S atoms which is monosubstituted or disubstituted by =O, =S, $=NR^3$, =N—CN, =N—$NO_2$, $=NOR^3$, $=NCOR^3$, $=NCOOR^3$ or $=NOCOR^3$ and may furthermore be monosubstituted, disubstituted or trisubstituted by $R^3$, Hal, A, $—[C(R^4)_2]_n$—Ar, $—[C(R^4)_2]_n$-Het, $—[C(R^4)_2]_n$-cycloalkyl, $OR^3$, $N(R^3)_2$, $NO_2$, CN, $COOR^3$, $CON(R^3)_2$, $NR^3COA$, $NR^3CON(R^3)_2$, $NR^3SO_2A$, $COR^3$, $SO_2NR^3$ and/or $S(O)_n A$, A is unbranched or branched alkyl having 1-10 carbon atoms in which one or two $CH_2$ groups may be replaced by O or S atoms and/or by —CH=CH— groups and/or in addition 1-7H atoms may be replaced by F, Ar is phenyl, naphthyl or biphenyl, each of which is unsubstituted or monosubstituted, disubstituted or trisubstituted by Hal, A, $OR^3$, $N(R^3)_2$, $NO_2$, CN, $COOR^3$, $CON(R^3)_2$, $NR^3COA$, $NR^3CON(R^3)_2$, $NR^3SO_2A$, $COR^3$, $SO_2N(R^3)_2$, $S(O)_n A$, $—[C(R^4)_2]_n$—$COOR^3$ or $—O[C(R^4)_2]_o$—$COOR^3$, Ar' is phenyl, naphthyl or biphenyl, each of which is unsubstituted or monosubstituted, disubstituted or trisubstituted by Hal, A, $OR^4$, $N(R^4)_2$, $NO_2$, CN, $COOR^4$, $CON(R^4)_2$, $NR^4COA$, $NR^4CON(R^4)_2$, $NR^4SO_2A$, $COR^4$, $SO_2N(R^4)_2$, $S(O)_n A$, $—[C(R^4)_2]_n$—$COOR^4$ or $—O[C(R^4)_2]_o$—$COOR^4$, Het is a monocyclic or bicyclic, saturated, unsaturated or aromatic heterocyclic ring having from 1 to 4 N, O and/or S atoms which may be unsubstituted or monosubstituted, disubstituted or trisubstituted by Hal, A, $—[C(R^4)_2]_n$—Ar, $—[C(R^4)_2]_n$-Het', $—[C(R^4)_2]_n$-cycloalkyl, $OR^3$, $N(R^3)_2$, $NR^3CON(R^3)_2$, $NO_2$, ON, $—[C(R^4)_2]_n$—$COOR^3$, $—[C(R^4)_2]_n$—$CON(R^3)_2$, $NR^3COA$, $NR^3SO_2A$, $COR^3$, $SO_2NR^3$, $S(O)_m A$ and/or carbonyl oxygen, Het' is a monocyclic or bicyclic, saturated, unsaturated or aromatic heterocyclic ring having from 1 to 4 N, O and/or S atoms which may be unsubstituted or monosubstituted or disubstituted by carbonyl oxygen, =S, $=N(R^4)_2$, Hal, A, $OR^4$, $N(R^4)_2$, $NO_2$, CN, $COOR^4$, $CON(R^4)_2$, $NR^4COA$, $NR^4CON(R^4)_2$, $NR^4SO_2A$, $COR^4$, $SO_2NR^4$ and/or $S(O)_n A$, Hal is F, Cl, Br or I, n is 0, 1 or 2, o is 1, 2 or 3, and pharmaceutically usable derivatives, solvates, salts and stereoisomers thereof, including mixtures thereof in all ratios.

The invention had the object of finding novel compounds having valuable properties, in particular those which can be used for the preparation of medicaments.

It has been found that the compounds of the formula I and salts thereof have very valuable pharmacological properties and are well tolerated. In particular, they exhibit factor Xa-inhibiting properties and can therefore be employed for combating and preventing thromboembolic diseases, such as thrombosis; myocardial infarction, arteriosclerosis, inflammation, apoplexy, angina pectoris, restenosis after angioplasty and claudicatio intermittens.

The compounds of the formula I according to the invention may furthermore be inhibitors of the coagulation factors factor VIIa, factor IXa and thrombin in the blood coagulation cascade.

Aromatic amidine derivatives having an antithrombotic action are disclosed, for example, in EP 0 540 051 B1, WO 98/28269, WO 00/71508, WO 00/71511, WO 00/71493, WO 00/71507, WO 00/71509, WO 00/71512, WO 00/71515 and WO 00/71516. Cyclic guanidines for the treatment of thromboembolic diseases are described, for example, in WO 97/08165. Aromatic heterocyclic compounds having a factor Xa inhibitory activity are disclosed, for example, in WO 96/10022. Substituted N-[(aminoiminomethyl)phenylalkyl] azaheterocyclylamides as factor Xa inhibitors are described in WO 96/40679.

Other carboxamide derivatives are disclosed in WO 02/48099 and WO 02/57236, other pyrrolidine derivatives are described in WO 02/100830.

Further heterocyclic derivatives are disclosed in WO 03/045912.

The antithrombotic and anticoagulant effect of the compounds according to the invention is attributed to the inhibitory action against activated coagulation protease, known by the name factor Xa, or to the inhibition of other activated serine proteases, such as factor VIIa, factor IXa or thrombin.

Factor Xa is one of the proteases involved in the complex process of blood coagulation. Factor Xa catalyses the conversion of prothrombin into thrombin. Thrombin cleaves fibrinogen into fibrin monomers, which, after crosslinking, make an elementary contribution to thrombus formation. Activation of thrombin may result in the occurrence of thromboembolic diseases. However, inhibition of thrombin may inhibit the fibrin formation involved in thrombus formation.

The inhibition of thrombin can be measured, for example by the method of G. F. Cousins et al. in *Circulation* 1996, 94, 1705-1712.

Inhibition of factor Xa can thus prevent the formation of thrombin.

The compounds of the formula f according to the invention and salts thereof engage in the blood coagulation process by inhibiting factor Xa and thus inhibit the formation of thrombuses.

The inhibition of factor Xa by the compounds according to the invention and the measurement of the anticoagulant and antithrombotic activity can be determined by conventional in-vitro or in-vivo methods. A suitable method is described, for example, by J. Hauptmann et al. in *Thrombosis and Haemostasis* 1990, 63, 220-223.

The inhibition of factor Xa can be measured, for example by the method of T. Hara et al. in *Thromb. Haemostas.* 1994, 71, 314-319.

Coagulation factor VIIa initiates the extrinsic part of the coagulation cascade after binding to tissue factor and contributes to the activation of factor X to give factor Xa. Inhibition of factor VIIa thus prevents the formation of factor Xa and thus subsequent thrombin formation.

The inhibition of factor VIIa by the compounds according to the invention and the measurement of the anticoagulant and antithrombotic activity can be determined by conventional in-vitro or in-vivo methods. A conventional method for the measurement of the inhibition of factor VIIa is described, for example, by H. F. Ronning et al. in *Thrombosis Research* 1996, 84, 73-81.

Coagulation factor IXa is generated in the intrinsic coagulation cascade and is likewise involved in the activation of factor X to give factor Xa. Inhibition of factor IXa can therefore prevent the formation of factor Xa in a different way.

The inhibition of factor IXa by the compounds according to the invention and the measurement of the anticoagulant and antithrombotic activity can be determined by conventional in-vitro or in-vivo methods. A suitable method is described, for example, by J. Chang at al. in *Journal of Biological Chemistry* 1998, 273, 12089-12094.

The compounds according to the invention may furthermore be used for the treatment of tumours, tumour diseases and/or tumour metastases.

A correlation between tissue factor TF/factor VIIa and the development of various types of cancer has been indicated by T. Taniguchi and N. R. Lemoine in Biomed. Health Res. (2000), 41 (Molecular Pathogenesis of Pancreatic Cancer), 57-59.

The publications listed below describe an antitumoural action of TF-VII and factor Xa inhibitors of various types of tumour:
K. M. Donnelly et al. in Thromb. Haemost. 1998; 79: 1041-1047;
E. G. Fischer et al. in J. Clin. Invest. 104: 1213-1221 (1999);
B. M. Mueller et al. in J. Clin. Invest. 101: 1372-1378 (1998);
M. E. Bromberg et al. in Thromb. Haemost. 1999; 82: 88-92.

The compounds of the formula I can be employed as medicament active ingredients in human and veterinary medicine, in particular for the treatment and prevention of thromboembolic diseases, such as thrombosis, myocardial infarction, arteriosclerosis, inflammation, apoplexy, angina pectoris, restenosis after angioplasty, claudicatio intermittens, venous thrombosis, pulmonary embolism, arterial thrombosis, myocardial ischaemia, unstable angina and strokes based on thrombosis.

The compounds according to the invention are also employed for the treatment or prophylaxis of atherosclerotic diseases, such as coronary arterial disease, cerebral arterial disease or peripheral arterial disease. The compounds are also employed in combination with other thrombolytic agents in myocardial infarction, furthermore for prophylaxis for reocclusion after thrombolysis, percutaneous transluminal angioplasty (PTCA) and coronary bypass operations.

The compounds according to the invention are furthermore used for the prevention of rethrombosis in microsurgery, furthermore as anticoagulants in connection with artificial organs or in haemodialysis.

The compounds are furthermore used in the cleaning of catheters and medical aids in patients in vivo, or as anticoagulants for the preservation of blood, plasma and other blood products in vitro. The compounds according to the invention are furthermore used for diseases in which blood coagulation makes a crucial contribution toward the course of the disease or represents a source of secondary pathology, such as, for example, in cancer, including metastasis, inflammatory diseases, including arthritis, and diabetes.

The compounds according to the invention are furthermore used for the treatment of migraine (F. Morales-Asin et al., Headache, 40, 2000, 45-47).

In the treatment of the diseases described, the compounds according to the invention are also employed in combination with other thrombolytically active compounds, such as, for example, with the "tissue plasminogen activator" t-PA, modified t-PA, streptokinase or urokinase. The compounds according to the invention are administered either at the same time as or before or after the other substances mentioned.

Particular preference is given to simultaneous administration with aspirin in order to prevent recurrence of the clot formation.

The compounds according to the invention are also used in combination with blood platelet glycoprotein receptor (IIb/IIIa) antagonists, which inhibit blood platelet aggregation.

The invention relates to the compounds of the formula I and salts thereof and to a process for the preparation of compounds of the formula I according to Claims 1-16 and pharmaceutically usable derivatives, solvates, salts and stereoisomers thereof, characterised in that
a) for the preparation of compounds of the formula I in which
  W is N and
  G is NH,
a compound of the formula II

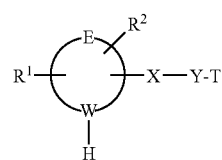

in which
$R^1$, $R^2$, E, X, Y and T are as defined in Claim 1,
and W is N,
is reacted with a compound of the formula III $$D-N=C=O \quad\quad\quad III$$

in which
D is as defined in Claim 1,
or
b) for the preparation of compounds of the formula I in which
X is —[C(R$^4$)$_2$]$_n$CONR$^3$[C(R$^4$)$_2$]$_n$—,
a compound of the formula IV

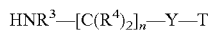   IV in which R$^3$, n, Y and T are as defined in Claim 1,
is reacted with a compound of the formula V

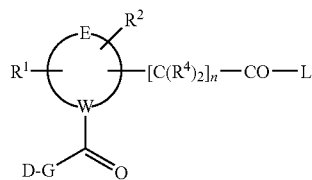   V in which
L is Cl, Br, I or a free or reactively functionally modified OH group, and R$^1$, R$^2$, R$^4$, D, E, G, W and n are as defined in Claim 1,
or
c) for the preparation of compounds of the formula I in which W is N,
a compound of the formula II

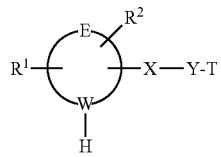   II in which
R$^1$, R$^2$, E, X, Y and T are as defined in Claim 1,
and W is N,
is reacted with a compound of the formula VI

   VI in which D and G are as defined in Claim 1, and
L is Cl, Br, I or a free or reactively functionally modified OH group,
and/or
a base or acid of the formula I is converted into one of its salts.

The invention also relates to the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds according to the invention and so-called prodrug compounds.

The term "prodrug derivatives" is taken to mean compounds of the formula I which have been modified with, for example, alkyl or acyl groups, sugars or oligopeptides and which are rapidly cleaved in the organism to form the active compounds according to the invention.

These also include biodegradable polymer derivatives of the compounds according to the invention, as described, for example, in Int. J. Pharm. 115, 61-67 (1995).

The invention also relates to mixtures of the compounds of the formula according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention also relates to pyrrolidinecarboxylic acid derivatives selected from the group consisting of
1-N-[(4-chlorophenyl)]-2-N-[(1'-methyl-[1,4']bipiperidinyl-4-yl)]-(2R,4R)-4-hydroxypyrrolidine-1,2-dicarboxamide,
1-N-[(4-chlorophenyl)]-2-N-[(3,4,5,6-tetrahydro-2H-[1,4']bipyridinyl-4-yl)]-(2R,4R)-4-hydroxypyrrolidine-1,2-dicarboxamide,
1-N-[(4-chlorophenyl)]-2-N-[(3,4,5,6-tetrahydro-2H-[1,4']bipyridinyl-4-yl)-(2R,4R)-4-ethoxypyrrolidine-1,2-dicarboxamide,
N-(4-chlorophenyl)-(2R,4R)-4-hydroxy-2-(4-pyridin-4-ylpiperazine-1-carbonyl)pyrrolidine-1-carboxamide,
N-(4-chlorophenyl)-(2R,4R)-4-hydroxy-2-[4-(2-methoxyphenyl)-piperazine-1-carbonyl]pyrrolidine-1-carboxamide,
N-(4-chlorophenyl)-(2R,4R)-2-[4-(4-fluorophenyl)piperazine-1-carbonyl]-4-hydroxypyrrolidine-1-carboxamide,
N-(4-chlorophenyl)-(2R,4R)-4-hydroxy-2-[4-hydroxy-4-(4-methoxyphenyl)piperidine-1-carbonyl]pyrrolidine-1-carboxamide,
N-(4-chlorophenyl)-(2R,4R)-4-hydroxy-2-(4-pyridin-2-ylpiperazine-1-carbonyl)pyrrolidine-1-carboxamide,
N-(4-chlorophenyl)-(2R,4R)-2-[4-(4-ethylpiperazin-1-yl)piperidine-1-carbonyl]-4-hydroxypyrrolidine-1-carboxamide,
N-(4-chlorophenyl)-(2R,4R)-2-[4-(4,6-dimethylpyrimidin-2-yl)-piperazine-1-carbonyl]-4-hydroxypyrrolidine-1-carboxamide,
N-(4-chlorophenyl)-(2R,4R)-4-hydroxy-2-[4-(1-methylpiperidin-4-yl)-piperazine-1-carbonyl]pyrrolidine-1-carboxamide;
1-N-[(4-chlorophenyl)]-2-N-{[2-(2-dimethylaminoethoxy)-4-morpholin-4-ylphenyl]}-(2R,4R)-4-hydroxypyrrolidine-1,2-dicarboxamide,
1-N-[(4-chlorophenyl)]-2-N-[(2-ethoxy-4-morpholin-4-ylphenyl)]-(2R,4R)-4-hydroxypyrrolidine-1,2-dicarboxamide,
1-N-[(4-chlorophenyl)]-2-N-[(4-morpholin-4-yl-2-propoxyphenyl)]-(2R,4R)-4-hydroxypyrrolidine-1,2-dicarboxamide,
and pharmaceutically usable derivatives, solvates, salts and stereoisomers thereof, including mixtures thereof in all ratios.

The invention also relates to cyclopentanecarboxylic acid derivatives selected from the group consisting of
N-[4-(3-oxomorpholin-4-yl)phenyl]-(rac)-2-[3-(4-chlorophenyl)-ureido]cyclopentanecarboxamide,
N-[3-methyl-4-(3-oxomorpholin-4-yl)phenyl]-(rac)-2-[3-(4-chlorophenyl)ureido]cyclopentanecarboxamide,
and pharmaceutically usable derivatives, solvates, salts and stereoisomers thereof, including mixtures thereof in all ratios.

For all radicals which occur more than once, such as, for example, A, their meanings are independent of one another.

Above and below, the radicals or parameters D, E, G, W, X, Y, T, R$^1$ and R$^2$ are as defined under the formula I, unless expressly stated otherwise.

A is alkyl, is unbranched (linear) or branched, and has 1, 2, 3, 4, 5, 6, 7, 8, 9 or 10 carbon atoms. A is preferably methyl, furthermore ethyl, propyl, iso-propyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2:, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl. A is very particularly preferably alkyl having 1, 2, 3, 4, 5 or 6 carbon atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cycloalkyl is preferably cyclopropyl, cyclobutyl, cyclopentyl, cyclohexyl or cycloheptyl.

Alkylene is preferably methylene, ethylene, propylene, butylene, pentylene or hexylene, furthermore branched alkylene.

$R^1$ and $R^2$ are each, independently of one another, preferably for example, H, =O, $COOR^3$, OH, OA, $NH_2$, alkyl having 1, 2, 3, 4, 5 or 6 carbon atoms, $N_3$, ethynyl, vinyl, allyloxy, NHCOA, $NHSO_2A$, $OCH_2COOA$ or $OCH_2COOH$.

$R^1$ is preferably H, =O, $COOR^3$, such as, for example, COOA, OH, OA, $NH_2$, alkyl having 1, 2, 3, 4, 5 or 6 carbon atoms, $N_3$, ethynyl, vinyl, allyloxy, —$OCOR^3$, such as, for example, methylcarbonyloxy, NHCOA, such as, for example, acetamino, or $NHSO_2A$, such as, for example, methylsulfonylamino; $OCH_2COOA$, such as, for example, $OCH_2COOCH_3$; or $OCH_2COOH$.

$R^2$ is preferably H, =O, OH, OA, such as, for example, methoxy, or alkyl having 1, 2, 3, 4, 5 or 6 carbon atoms.

In a further preferred embodiment,
$R^1$ is H, =O, $COOR^3$, OH, OA, $NH_2$, alkyl having 1, 2, 3, 4, 5 or 6 carbon atoms, $N_3$, ethynyl, vinyl, allyloxy, —$OCOR^3$, NHCOA, $NHSO_2A$, H—C≡C—$CH_2$—, $CH_3$—C≡C—$CH_2$—O—, —O—$CH_2$—CH(OH)—$CH_2OH$, —O—$CH_2$—CH(OH)—$CH_2NH_2$, —O—$CH_2$—CH(OH)—$CH_2$Het', $OCH_2COOCH_3$ or $OCH_2COOH$;
$R^2$ is H, =O, OH, OA or alkyl having 1, 2, 3, 4, 5 or 6 carbon atoms;
Het' is a saturated 3-6-membered heterocyclic ring having from 1 to 3 N and/or O atoms, which may be unsubstituted or monosubstituted or disubstituted by carbonyl oxygen, Hal, A, OH, $NH_2$, $NO_2$, CN, COOA or $CONH_2$.

In another preferred embodiment,
$R^1$ is ethynyl, vinyl, allyloxy, $CH_3$—C≡C—$CH_2$—O—, —O—$CH_2$—CH(OH)—$CH_2OH$, —O—$CH_2$—CH(OH)—$CH_2NH_2$, —O—$CH_2$—CH(OH)—$CH_2$Het', $OCH_2COOCH_3$ or $OCH_2COOH$,
$R^2$ is H, A or OH,
Het' is a saturated 3-6-membered heterocyclic ring having from 1 to 3 N and/or O atoms, which may be unsubstituted or monosubstituted or disubstituted by carbonyl oxygen, Hal, A, OH, $NH_2$, $NO_2$, CN, COOA or $CONH_2$.

In a further preferred embodiment,
$R^1$ is ethynyl, vinyl, allyloxy, —$CH_3$—C≡C—$CH_2$—O—, —O—$CH_2$—CH(OH)—$CH_2OH$, —O—$CH_2$—CH(OH)—$CH_2NH_2$, —O—$CH_2$—CH(OH)—$CH_2$Het', $OCH_2COOCH_3$ or $OCH_2COOH$,
$R^2$ is H, A or OH,
Het' is a saturated 3-6-membered heterocyclic ring having from 1 to 3 N and/or O atoms, which may be unsubstituted or monosubstituted or disubstituted by carbonyl oxygen.

Het' in this connection is very particularly preferably pyrrolidine, piperidine or oxazolidine, each of which is unsubstituted or monosubstituted by carbonyl oxygen.

$R^1$ and $R^2$ together are alternatively a 3- to 6-membered carbocyclic or heterocyclic ring having from 0 to 3 N, O and/or S atoms which is spirocyclically or bicyclically bonded (fused) to the

ring system. The 3- to 6-membered carbocyclic or heterocyclic ring here is, for example, phenyl, cyclopropyl, cyclobutyl, cyclopentyl, cyclohexyl, pyridyl, imidazolyl, piperidinyl or 1,3-dioxolanyl.

$R^1$ and $R^2$ together are in particular a 3- to 6-membered carbocyclic ring which is spirocyclically bonded to the

ring system. The 3- to 6-membered carbocyclic ring here is preferably cyclopropyl, cyclobutyl, cyclopentyl or cyclohexyl.

$R^3$ is preferably H or A, furthermore also phenyl, benzyl or $[C(R^4)_2]_n COOA$, such as, for example, $CH_2COOCH_3$.

$R^4$ is preferably H or A, very particularly preferably H.

$COR^2$, $COR^3$ and $COR^4$ are, for example, CHO or —COA.

—COA (acyl) is preferably acetyl, propionyl, furthermore also butyryl, pentanoyl, hexanoyl or, for example, benzoyl.

Hal is preferably F, Cl or Br, but alternatively I.

Ar is, for example, phenyl, o-, m- or p-tolyl, o-, m- or p-ethylphenyl, o-, m- or p-propylphenyl, or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl; o-, m- or p-(N,N-di-methylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-phenoxyphenyl, further preferably 2,3-, 2,4-, 2,5-, 2,6-, 3,4- or 3,5-di-fluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar is preferably, for example, phenyl which is unsubstituted or monosubstituted, disubstituted or trisubstituted by Hal, A, $OR^2$, $OR^3$, $SO_2A$, $COOR^2$ or CN.

Ar is particularly preferably, for example, phenyl which is unsubstituted or monosubstituted or disubstituted by Hal, A, OA, phenoxy, $SO_2A$, $SO_2NH_2$, $COOR^2$ or CN, such as, for example, phenyl, 2-methylsulfonylphenyl, 2-aminosulfonylphenyl, phenoxyphenyl, 2-, 3- or 4-chlorophenyl, 3,4- dichlorophenyl, 4-methylphenyl, 4-bromophenyl, 3-fluoro-4-methoxyphenyl, 4-trifluoromethoxyphenyl, 4-ethoxyphenyl, 2-methoxyphenyl, 3-cyanophenyl, 4-ethoxycarbonylphenyl, methoxycarbonylphenyl, carboxyphenyl or aminocarbonylphenyl.

Ar is very particularly preferably unsubstituted phenyl, 4-chlorophenyl or 2-methylsulfonylphenyl.

G is particularly preferably $(CH_2)_n$, —CH=CH— or —CH=CH—CH=CH—.

X is particularly preferably —CONH— or —CON($CH_2COOA$)-.

Y is preferably cycloalkylene, Het-diyl or Ar-diyl, particularly preferably 1,4-phenylene which is unsubstituted or monosubstituted or disubstituted by A, OA, Cl, F, $COOCH_3$, COOH, phenoxy or aminocarbonyl, furthermore also pyridinediyl, preferably pyridine-2,5-diyl, piperidinediyl or cyclohexylene.

Y is in particular pyridinediyl, piperidinediyl, cyclohexylene, or phenylene which is unsubstituted or monosubstituted or disubstituted by A, OA, Cl, F, $COOCH_3$, COOH, phenoxy or aminocarbonyl.

Het is, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxane-6-yl, 2,1,3-benzothiadiazol-4- or -5-yl or 2,1,3-benzoxadiazol-5-yl.

The heterocyclic radicals may also be partially or fully hydrogenated.

Het can thus also be, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2H-3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or hexahydro-1-, -3 or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or alternatively 3,4-dihydro-2H-1,5-benzodioxepin-6- or -7-yl, furthermore preferably 2,3-dihydrobenzofuranyl or 2,3-dihydro-2-oxofuranyl.

Het' is preferably, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 5-, 6- or 7-benzisoxazolyl, 2-, 4 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or. 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-,7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxane-6-yl, 2,1,3-benzothiadiazol-4- or -5-yl or 2,1,3-benzoxadiazol-5-yl.

The heterocyclic radicals may also be partially or fully hydrogenated.

Het' can thus also be, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or 5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or alternatively 3,4-dihydro-2H-1,5-benzodioxepin-6- or -7-yl, furthermore preferably 2,3-dihydrobenzofuranyl or 2,3-dihydro-2-oxofuranyl.

T is preferably a monocyclic or bicyclic, saturated or unsaturated heterocyclic ring having 1 to 2 N and/or O atoms which is monosubstituted or disubstituted by =O, =S, =NR$^2$, =N—CN, =N—NO$_2$, =NOR$^2$, =NCOR$^2$, =NCOOR$^2$ or =NOCOR$^2$ and may furthermore be monosubstituted or disubstituted by Hal, A or OA.

In a further embodiment, T is preferably, for example, 2-iminopiperidin-1-yl, 2-iminopyrrolidin-1-yl, 2-imino-1H-pyridin-1-yl, 3-iminomorpholin-4-yl, 2,6-diiminopiperidin-1-yl, 2-iminopiperazin-1-yl, 2,6-diiminopiperazin-1-yl, 2,5-diiminopyrrolidin-1-yl, 2-imino-1,3-oxazolidin-3-yl, 3-imino-2H-pyridazin-2 yl, 2-iminoazepan-1-yl, 2-hydroxy-6-iminopiperazin-1-yl or 2-methoxy-6-iminopiperazin-1-yl.

T is, in particular, a monocyclic, saturated or unsaturated heterocyclic ring having 1 to 2 N and/or O atoms which is monosubstituted or disubstituted by =O, =S or =NH and may furthermore be monosubstituted or disubstituted by Hal, A and/or OA.

T is particularly preferably piperidin-1-yl, pyrrolidin-1-yl, pyridin-1-yl, morpholin-4-yl, piperazin-1-yl, 1,3-oxazolidin-3-yl, pyridazin-2-yl, pyrazin-1-yl, azepan-1-yl, 2-azabicyclo[2.2.2]octan-2-yl, imidazolidinyl, thiazolyl or 1,4-oxazepanyl, each of which is monosubstituted or disubstituted by =O or =NH and where the radicals may also be monosubstituted or disubstituted by Hal, A and/or OA;

very particular preference is given to 3-oxomorpholin-4-yl.

T is furthermore preferably also 2-oxo-3-methoxy-1H-pyridin-1-yl.

D is preferably phenyl, thienyl, pyridyl, furyl, thiazolyl, pyrrolyl or imidazolyl, each of which is monosubstituted or disubstituted by Hal, particularly preferably phenyl, pyridyl, thienyl, furyl or imidazolyl, each of which is monosubstituted or disubstituted by Hal.

The radical

is preferably pyrrolidine-1,2-diyl, piperidine-1,2-diyl, piperidine-1,3-diyl, oxazolidine-3,4- or -3,5-diyl, thiazolidine-3,4-diyl, 2,5-dihydro-1H-pyrrole-1,5-diyl, 1,3-oxazinane-3,4-diyl, tetrahydrofuran-3,4-diyl or azetidine-1,2-diyl.

The compounds of the formula I can have one or more centres of chirality and can therefore occur in various stereoisomeric forms. The formula I covers all these forms.

Accordingly, the invention relates, in particular, to compounds of the formula I in which at least one of the said radicals has one of the preferred meanings indicated above. Some preferred groups of compounds can be expressed by the following sub-formulae Ia to Iw, which conform to the formula I and in which the radicals not designated in greater detail are as defined under the formula I, but in which in Ia D is a monocyclic or bicyclic, aromatic carbocyclic or heterocyclic ring having from 0 to 4 N, O and/or S atoms which is unsubstituted or monosubstituted or disubstituted by Hal;

in Ib is phenyl, pyridyl, thienyl, furyl or imidazolyl, each of which is monosubstituted or disubstituted by Hal;

in Ic $R^1$, $R^2$ are each, independently of one another, H, =O, $COOR^3$, OH, OA, $NH_2$, alkyl having 1, 2, 3, 4, 5 or 6 carbon atoms, $N_3$, ethynyl, vinyl, allyloxy, NHCOA, $OCH_2COOA$ or $OCH_2COOH$;

in Id G is $(CH_2)_n$, $(CH_2)_nNH$—, —CH=CH— or —CH=CH—CH=CH—;

in Ie X is —$[C(R^4)_2]_nCONR^3[C(R^4)_2]_n$—;

in If X is —CONH— or —CON($CH_2COOA$)-;

in Ig Y is cycloalkylene, Het-diyl or Ar-diyl;

in Ih Y is pyridinediyl, piperidinediyl, cyclohexylene, or 1,4-phenylene which is unsubstituted or monosubstituted or disubstituted by A, OA, Cl, F, $COOCH_3$, COON, phenoxy or aminocarbonyl;

in Ii T is a monocyclic, saturated or unsaturated heterocyclic ring having 1 to 2 N and/or O atoms which is monosubstituted or disubstituted by =O, =S or =NH and may be monosubstituted or disubstituted by Hal, A and/or OA;

in Ij T is piperidin-1-yl, pyrrolidin-1-yl, morpholin-4-yl, piperazin-1-yl, 1,3-oxazolidin-3-yl, pyridazin-2-yl, pyrazin-1-yl, azepan-1-yl, 2-azabicyclo[2.2.2]octan-2-yl, imidazolidinyl, thiazolyl or 1,4-oxazepanyl, each of which is monosubstituted or disubstituted by =O or =NH and where the radicals may also be monosubstituted or disubstituted by Hal, A and/or OA;

in Ik Ar is phenyl which is unsubstituted or monosubstituted or disubstituted by Hal, A, OA, $SO_2A$, $COOR^2$, $SO_2NH_2$, CN, COOA, COOH or phenoxy;

in Il D is a monocyclic or bicyclic, aromatic carbocyclic or heterocyclic ring having from 0 to 4 N, O and/or S atoms which is unsubstituted or monosubstituted or disubstituted by Hal, $R^1$, $R^2$ are each, independently of one another, H, =O, $COOR^3$, OH, OA, $NH_2$, alkyl having 1, 2, 3, 4, 5 or 6 carbon atoms, $N_3$, ethynyl, vinyl, allyloxy, NHCOA, $NHSO_2A$, $OCH_2COOA$ or $OCH_2COOH$, $R^1$ and $R^2$ together are alternatively a spirocyclidally bonded 3- to 6-membered carbocyclic ring, $R^3$ is H, A, phenyl, benzyl or $[C(R^4)_2]_nCOOA$, $R^4$ is H or A, W is N, $CR^3$ or an $sp^2$-hybridised carbon atom, E together with W is a 3- to 7-membered saturated carbocyclic or heterocyclic ring having from 0 to 3 N, from 0 to 2 O and/or from 0 to 2 S atoms, which may contain a double bond, G is $(CH_2)_n$, $(CH_2)_nNH$—, —CH=CH— or —CH=CH—CH=CH—, X is —$[C(R^4)_2]_nCONR^3[C(R^4)_2]_n$—, Y is cycloalkylene, Het-diyl or Ar-diyl, Ar is phenyl which is unsubstituted or monosubstituted or disubstituted by Hal, A, OA, $SO_2A$, $COOR^2$, $SO_2NH_2$, CN, COOA, COON or phenoxy, T is a monocyclic, saturated or unsaturated heterocyclic ring having 1 to 2 N and/or O atoms which is monosubstituted or disubstituted by =O, =S or =NH and may be monosubstituted or disubstituted by Hal, A and/or OA, A is unbranched or branched alkyl having 1-10 carbon atoms and in which 1-7H atoms may be replaced by F, Hal is F, Cl, Br or I, n is 0, 1 or 2;

in Im D is phenyl, pyridyl, thienyl, furyl or imidazolyl, each of which is monosubstituted or disubstituted by Hal, $R^1$, $R^2$ are each, independently of one another, H, =O, $COOR^3$, OH, OA, $NH_2$, alkyl having 1, 2, 3, 4, 5 or 6 carbon atoms, $N_3$, ethynyl, vinyl, allyloxy, NHCOA, $NHSO_2A$, $OCH_2COOA$ or $OCH_2COOH$, $R^1$ and $R^2$ together are alternatively a spirocyclically bonded 3- to 6-membered carbocyclic ring, $R^3$ is H, A or $CH_2COOA$, $R^4$ is H or A, W is N, $CR^3$ or an $sp^2$-hybridised carbon atom, E together with W is a 3- to 7-membered saturated carbocyclic or heterocyclic ring having from 0 to 3 N, from 0 to 2 O and/or from 0 to 2 S atoms, which may contain a double bond, G is $(CH_2)_n$, $(CH_2)_nNH$—, —CH=CH— or —CH=CH—CH=CH—, X is —CONH— or —CON($CH_2COOA$)-, Y is pyridinediyl, piperidinediyl, cyclohexylene, or phenylene which is unsubstituted or monosubstituted or disubstituted by A, OA, Cl, F, $COOCH_3$, COOH, phenoxy or aminocarbonyl, T is piperidin-1-yl, pyridin-1-yl, morpholin-4-yl, piperazin-1-yl, 1,3-oxazolidin-3-yl, pyridazin-2-yl, pyrazin-1-yl, azepan-1-yl, 2-azabicyclo[2.2.2]octan-2-yl, imidazolidinyl, thiazolyl or 1,4-oxazepanyl, each of which is monosubstituted or disubstituted by =O or =NH and where the radicals may also be monosubstituted or disubstituted by Hal, A and/or OA A is unbranched or branched alkyl having 1-10 carbon atoms and in which 1-7H atoms may be replaced by F, Hal is F, Cl, Br or I, n is 0, 1 or 2;

in In D is phenyl, pyridyl or thienyl, each of which is monosubstituted or disubstituted by Hal, $R^1$ is H, =O, $COOR^3$, OH, OA, $NH_2$, alkyl having 1, 2, 3, 4, 5 or 6 carbon atoms, $N_3$, ethynyl, vinyl, allyloxy, —$OCOR^3$, NHCOA or $NHSO_2A$, R² is H, =O, OH, OA or alkyl having 1, 2, 3, 4, 5 or 6 carbon atoms,
R¹ and R² together are alternatively a spirocyclically bonded 3- to 6-membered carbocyclic ring,
R³ is H or A,
R⁴ is H or A,

is pyrrolidine-1,2-diyl, oxazolidine-3,4- or 3,5-diyl, thiazolidine-3,4-diyl, 2,5-dihydro-1H-pyrrole-1,5-diyl, 1,3-dioxolane-4,5-diyl, 1,3-oxazinane-3,4-diyl, piperazine-1,4-diyl, tetrahydrofuran-3,4-diyl or azetidine-1,2-diyl,
G is $(CH_2)_n$ or $(CH_2)_n NH—$,
X is CONH,
Y is 1,3- or 1,4-phenylene which is unsubstituted or monosubstituted or disubstituted by methyl, trifluoromethyl, ethyl, propyl, Cl or F,
T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, pyrazin-1-yl, azepan-1-yl or 2-azabicyclo[2.2.2]octan-2-yl, each of which is monosubstituted or disubstituted by carbonyl oxygen,
A is unbranched or branched alkyl having 1-10 carbon atoms and in which 1-7H atoms may be replaced by F,
Hal is F, Cl, Br or I,
n is 0, 1 or 2,
in Io D is phenyl, pyridyl or thienyl, each of which is monosubstituted or disubstituted by Hal,
R¹ is H, =O, $COOR^3$, OH, OA, $NH_2$, alkyl having 1, 2, 3, 4, 5 or 6 carbon atoms, $N_3$, ethynyl, vinyl, allyloxy, $—OCOR^3$, NHCOA or $NHSO_2A$,
R² is H, =O, OH, OA or alkyl having 1, 2, 3, 4, 5 or 6 carbon atoms,
R¹ and R² together are alternatively a spirocyclically bonded 3- to 6-membered carbocyclic ring,
R³ is H or A,
R⁴ is H or A,

is pyrrolidine-1,2-diyl, piperidine-1,2-diyl, oxazolidine-3,4- or 3,5-diyl, thiazolidine-3,4-diyl, 2,5-dihydro-1H-pyrrole-1,5-diyl, 1,3-dioxolane-4,5-diyl, 1,3-oxazinane-3,4-diyl, piperazine-1,4-diyl, tetrahydrofuran-3,4-diyl or azetidine-1,2-diyl,
G is $(CH_2)_n$ or $(CH_2)_n NH—$,
X is CONH,
Y is 1,3- or 1,4-phenylene which is unsubstituted or monosubstituted or disubstituted by methyl, trifluoromethyl, ethyl, propyl, Cl or F,
T is morpholin-4-yl which is monosubstituted or disubstituted by carbonyl oxygen,
A is unbranched or branched alkyl having 1-10 carbon atoms and in which 1-7H atoms may be replaced by F,
Hal is F, Cl, Br or I,
n is 0, 1 or 2, in Ip X is $—[C(R^4)_2]_n CONR^3[C(R^4)_2]_n—$ or $—[C(R^4)_2]_n CO[C(R^4)_2]_n—$;
in Iq X is CONH or $COCH_2$,
in Ir D is phenyl, pyridyl or thienyl, each of which is monosubstituted or disubstituted by Hal,
R¹ is H, =O, $COOR^3$, OH, OA, $NH_2$, alkyl having 1, 2, 3, 4, 5 or 6 carbon atoms, $N_3$, ethynyl, vinyl, allyloxy, $—OCOR^3$, NHCOA or $NHSO_2A$,
R² is H, =O, OH, OA or alkyl having 1, 2, 3, 4, 5 or 6 carbon atoms,
R¹ and R² together are alternatively a spirocyclically bonded 3- to 6-membered carbocyclic ring,
R³ is H or A,
R⁴ is H or A,

is pyrrolidine-1,2-diyl, piperidine-1,2-diyl, oxazolidine-3,4- or 3,5-diyl, thiazolidine-3,4-diyl, 2,5-dihydro-1H-pyrrole-1,5-diyl, 1,3-oxazinane-3,4-diyl, piperazine-1,4-diyl, tetrahydrofuran-3,4-diyl or azetidine-1,2-diyl,
G is $(CH_2)_n$ or $(CH_2)_n NH—$,
X is CONH or $COCH_2$,
Y is 1,3- or 1,4-phenylene which is unsubstituted or monosubstituted or disubstituted by methyl, trifluoromethyl, ethyl, propyl, Cl or F,
T is morpholin-4-yl which is monosubstituted or disubstituted by carbonyl oxygen,
A is unbranched or branched alkyl having 1-10 carbon atoms and in which 1-7H atoms may be replaced by F,
Hal is F, Cl, Br or I,
n is 0, 1 or 2,
in Is D is a monocyclic or bicyclic, aromatic carbocyclic or heterocyclic ring having from 0 to 4 N, O and/or S atoms which is unsubstituted or monosubstituted or disubstituted by Hal,
R¹, R² are each, independently of one another, H, =O, $COOR^3$, OH, OA, $NH_2$, alkyl having 1, 2, 3, 4, 5 or 6 carbon atoms, $N_3$, ethynyl, vinyl, allyloxy, $—OCOR^3$, NHCOA or $NHSO_2A$,
R¹ and R² together are alternatively a spirocyclically bonded 3- to 6-membered carbocyclic ring,
R³ is H or A,
R⁴ is H or A,
W is N, $CR^3$ or an $sp^2$-hybridised carbon atom,
E together with W is a 3- to 7-membered saturated carbocyclic or heterocyclic ring having from 0 to 3 N, from 0 to 2 O and/or from 0 to 2 S atoms,
which may contain a double bond,
G is $(CH_2)_n$ or $(CH_2)_n NH—$,
X is $—[C(R^4)_2]_n CONR^3[C(R^4)_2]_n—$ or $—[C(R^4)_2]_n CO[C(R^4)_2]_n—$,
Y is Ar-diyl,
Ar is phenyl which is unsubstituted or monosubstituted or disubstituted by Hal, A, OA, $SO_2A$, $COOR^2$, $SO_2NH_2$ or CN,
T is morpholin-4-yl which is monosubstituted or disubstituted by carbonyl oxygen,
A is unbranched or branched alkyl having 1-10 carbon atoms and in which 1-7H atoms may be replaced by F,
Hal is F, Cl, Br or I,
n is 0, 1 or 2, in It D is phenyl, pyridyl or thienyl, each of which is monosubstituted or disubstituted by Hal, $R^1$ is H, =O, COOR$^3$, OH, OA, NH$_2$, alkyl having 1, 2, 3, 4, 5 or 6 carbon atoms, N$_3$, ethynyl, vinyl, allyloxy, —OCOR$^3$, NHCOA, NHSO$_2$A, CH$_3$—C≡C—CH$_2$—O—, —O—CH$_2$—CH(OH)—CH$_2$OH, —O—CH$_2$—CH(OH)—CH$_2$NH$_2$ or —O—CH$_2$—CH(OH)—CH$_2$Het', $R^2$ is H, OH, OA or alkyl having 1, 2, 3, 4, 5 or 6 carbon atoms, $R^1$ and $R^2$ together are alternatively a spirocyclically bonded 3- to 6-membered carbocyclic ring, $R^3$ is H or A, $R^4$ is H or A,

is pyrrolidine-1,2-diyl, piperidine-1,2-diyl, oxazolidine-3,4- or 3,5-diyl, thiazolidine-3,4-diyl, 2,5-dihydro-1H-pyrrole-1,5-diyl, 1,3-dioxolane-4,5-diyl, 1,3-oxazinane-3,4-diyl, piperazine-1,4-diyl, tetrahydrofuran-3,4-diyl or azetidine-1,2-diyl, G is (CH$_2$)$_n$ or (CH$_2$)$_n$NH—, X is CONH or COCH$_2$, Y is 1,3- or 1,4-phenylene which is unsubstituted or monosubstituted or disubstituted by methyl, trifluoromethyl, ethyl, propyl, Cl or F, T is morpholin-4-yl which is monosubstituted or disubstituted by carbonyl oxygen, Het' is a saturated 3-6-membered heterocyclic ring having from 1 to 3 N and/or O atoms, which may be unsubstituted or monosubstituted or disubstituted by carbonyl oxygen, Hal, A, OH, NH$_2$, NO$_2$, CN, COOA or CONH$_2$, A is unbranched or branched alkyl having 1-10 carbon atoms and in which 1-7H atoms may be replaced by F, Hal is F, Cl, Br or I, n is 0, 1 or 2;

in Iu D is phenyl, pyridyl or thienyl, each of which is monosubstituted or disubstituted by Hal, $R^1$ is H, =O, COOR$^3$, OH, OA, NH$_2$, alkyl having 1, 2, 3, 4, 5 or 6 carbon atoms, N$_3$, ethynyl, vinyl, allyloxy, —OCOR$^3$, NHCOA, NHSO$_2$A, H—C≡C—CH$_2$—, CH$_3$—C≡C—CH$_2$—O—, —O—CH$_2$—CH(OH)—CH$_2$OH, —O—CH$_2$—CH(OH)—CH$_2$NH$_2$ or —O—CH$_2$—CH(OH)—CH$_2$Het', $R^2$ is H, =O, OH, OA or alkyl having 1, 2, 3, 4, 5 or 6 carbon atoms, $R^1$ and $R^2$ together are alternatively a spirocyclically bonded 3- to 6-membered carbocyclic ring, $R^3$ is H or A, $R^4$ is H or A,

is pyrrolidine-1,2-diyl, piperidine-1,2-diyl, oxazolidine-3,4- or 3,5-diyl, thiazolidine-3,4-diyl, 2,5-dihydro-1H-pyrrole-1,5-diyl, 1,3-dioxolane-4,5-diyl, 1,3-oxazinane-3,4-diyl, piperazine-1,4-diyl, tetrahydrofuran-3,4-diyl or azetidine-1,2-diyl, G is (CH$_2$)$_n$ or (CH$_2$)$_n$NH—, X is CONH, COCH$_2$, CO or COO, Y is 1,3- or 1,4-phenylene which is unsubstituted or monosubstituted or disubstituted by methyl, trifluoromethyl, ethyl, propyl, Cl or F, T is morpholin-4-yl which is monosubstituted or disubstituted by carbonyl oxygen, Het' is a saturated 3-6-membered heterocyclic ring having from 1 to 3 N and/or O atoms, which may be unsubstituted or monosubstituted or disubstituted by carbonyl oxygen, Hal, A, OH, NH$_2$, NO$_2$, CN, COOA or CONH$_2$, A is unbranched or branched alkyl having 1-10 carbon atoms and in which 1-7H atoms may be replaced by F, Hal is F, Cl, Br or I, n is 0, 1 or 2;

in Iv D is phenyl, pyridyl or thienyl, each of which is monosubstituted or disubstituted by Hal, $R^1$ is ethynyl, vinyl, allyloxy, CH$_3$—C≡C—CH$_2$—O—, —O—CH$_2$—CH(OH)—CH$_2$OH, —O—CH$_2$—CH(OH)—CH$_2$NH$_2$ or —O—CH$_2$—CH(OH)—CH$_2$Het', $R^2$ is H or OH, $R^1$ and $R^2$ together are alternatively a spirocyclically bonded 3- to 6-membered carbocyclic ring, $R^3$ is H or A, $R^4$ is H or A,

is pyrrolidine-1,2-diyl, piperidine-1,2-diyl, oxazolidine-3,4- or 3,5-diyl, thiazolidine-3,4-diyl, 2,5-dihydro-1H-pyrrole-1,5-diyl, 1,3-dioxolane-4,5-diyl, 1,3-oxazinane-3,4-diyl, piperazine-1,4-diyl, tetrahydrofuran-3,4-diyl or azetidine-1,2-diyl, G is (CH$_2$)$_n$ or (CH$_2$)$_n$NH—, X is CONH, CO, COO or COCH$_2$, Y is 1,3- or 1,4-phenylene which is unsubstituted or monosubstituted or disubstituted by methyl, trifluoromethyl, ethyl, propyl, Cl or F, T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, pyrazin-1-yl, azepan-1-yl or 2-azabicyclo-[2.2.2]octan-2-yl, each of which is monosubstituted or disubstituted by carbonyl oxygen or OA, Het' is a saturated 3-6-membered heterocyclic ring having from 1 to 3 N and/or O atoms, which may be unsubstituted or monosubstituted or disubstituted by carbonyl oxygen, Hal, A, OH, NH$_2$, NO$_2$, CN, COOA or CONH$_2$, A is unbranched or branched alkyl having 1-10 carbon atoms and in which 1-7H atoms may be replaced by F, Hal is F, Cl, Br or I, n is 0, 1 or 2;

in Iw D is phenyl, pyridyl, thienyl, furyl or imidazolyl, each of which is monosubstituted or disubstituted by Hal, $R^1$ is H, =O, COOR$^3$, OH, OA, NH$_2$, alkyl having 1, 2, 3, 4, 5 or 6 carbon atoms, N$_3$, ethynyl, vinyl, allyloxy, NHCOA, NHSO$_2$A, OCH$_2$COOA or OCH$_2$COOH, $R^2$ is H, =O, OH, OA or alkyl having 1, 2, 3, 4, 5 or 6 carbon atoms, $R^1$ and $R^2$ together are alternatively a spirocyclically bonded 3- to 6-membered carbocyclic ring, R³ is H or A,
R⁴ is H or A,

is pyrrolidine-1,2-diyl, piperidine-1,2-diyl, oxazolidine-3,4- or 3,5-diyl, thiazolidine-3,4-diyl, 2,5-dihydro-1H-pyrrole-1,5-diyl, 1,3-dioxolane-4,5-diyl, 1,3-oxazinane-3,4-diyl, piperazine-1,4-diyl, tetrahydrofuran-3,4-diyl or azetidine-1,2-diyl, G is $(CH_2)_n$, $(CH_2)_n NH-$, $-CH=CH-$ or $-CH=CH-CH=CH-$, X is $CONH$, $COCH_2$ or $-CON(CH_2COOA)-$, Y is pyridinediyl, piperidinediyl, cyclohexylene, or phenylene which is unsubstituted or monosubstituted or disubstituted by A, OA, Cl, F, $COOCH_3$, COOH, phenoxy or aminocarbonyl, T is morpholin-4-yl which is monosubstituted or disubstituted by carbonyl oxygen, A is unbranched or branched alkyl having 1-10 carbon atoms and in which 1-7H atoms may be replaced by F, Hal is F, Cl, Br or I, n is 0, 1 or 2;

and pharmaceutically usable derivatives, solvates, salts and stereoisomers thereat including mixtures thereof in all ratios.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ so that they are not isolated from the reaction mixture, but instead are immediately converted further into the compounds of the formula I.

The starting compounds of the formulae II, III, IV, V and VI are generally known. If they are novel, they can, however, be prepared by methods known per se.

Compounds of the formula I can preferably be obtained by reacting compounds of the formula II with compounds of the formula III.

The reaction is generally carried out in an inert solvent, in the presence of an acid-binding agent, preferably an alkali or alkaline earth metal hydroxide, carbonate or bicarbonate or another salt of a weak acid of the alkali or alkaline earth metals, preferably of potassium, sodium, calcium or caesium. It may also be favourable to add an organic base, such as triethylamine, dimethylaniline, pyridine or quinoline, or of an excess of the phenol component of the formula II or of the alkylation derivative of the formula III. Depending on the conditions used, the reaction time is between a few minutes and 14 days, and the reaction temperature is between about 0° and 150°, normally between 20° and 130°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxanee; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Compounds of the formula I can furthermore preferably be obtained by, reacting compounds of the formula IV with compounds of the formula V. The reaction is generally carried out in art inert solvent and under conditions as indicated above.

In the compounds of the formula V, L is preferably Cl, Br, I or a free or reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N-hydroxysuccinimide.

The reaction is generally carried out in an inert solvent, in the presence of an acid-binding agent, preferably an organic base, such as DIPEA, triethylamine, dimethylaniline, pyridine or quinoline, or an excess of the carboxyl component of the formula V.

It may also be favourable to add an alkali or alkaline earth metal hydroxide, carbonate or bicarbonate or another salt of a weak acid of the alkali or alkaline earth metals, preferably of potassium, sodium, calcium or caesium.

Depending on the conditions used, the reaction time is between a few minutes and 14 days, and the reaction temperature is between about −30° and 140°, normally between −10° and 90°, in particular between about 0° and about 70°.

Suitable inert solvents are those mentioned above.

Compounds of the formula I can furthermore preferably be obtained by reacting compounds of the formula II with compounds of the formula VI. The reaction is generally carried out in an inert solvent and under conditions as indicated above.

In the compounds of the formula VI, L is preferably Cl, Br, I or a free or reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy).

Compounds of the formula I can furthermore preferably be obtained by reacting a compound of the formula D-NH₂, in which D is as defined in Claim 1, with a chloroformate derivative, for example 4-nitrophenyl chloroformate, to give a carbamate intermediate, and subsequently reacting this with a compound of the formula II.

This is carried out under conditions as described above.

Compounds of the formula I can furthermore be obtained by liberating compounds of the formula I from one of their functional derivatives by treatment with a solvolysing or hydrogenolysing agent.

Preferred starting materials for the solvolysis or hydrogenolysis are those which conform to the formula I, but contain corresponding protected amino and/or hydroxyl groups instead of one, or more free amino and/or hydroxyl groups, preferably those which carry an amino-protecting group instead of an H atom bonded to an N atom, in particular those which carry an R'—N group, in which R' is an amino-protecting group, instead of an HN group, and/or those which carry a hydroxyl-protecting group instead of the H atom of a hydroxyl group, for example those which conform to the formula I, but carry a —COOR" group, in which R" is a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC (tort-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tent-butyl and acetyl, where benzyl and tert-butyl are particularly preferred.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong Organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxanee, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut and Mtr groups can, for example, preferably be cleaved off using TFA in dichloromethane or using approximately 3 to 5N HCl in dioxanee at 15-30°, and the FMOC group can be cleaved off using an approximately 5 to 50% solution of dimethylamine, diethylamine or piperidine in DMF at 15-30°.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suit able solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxanee; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethylformamide (DMF); nitrites, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using NaOH or KOH in water, water/THF or water/dioxanee, at temperatures between 0 and 100°.

Free amino groups can furthermore be acylated in a conventional manner using an acid chloride or anhydride Or alkylated using an unsubstituted or substituted alkyl halide or reacted with $CH_3$—C(=NH)—OEt, advantageously in an inert solvent, such as dichloromethane or THF and/or in the presence of a base, such as triethylamine or pyridine, at temperatures between −60 and +30°.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (for example sodium hydroxide, potassium hydroxide, sodium carbonate or potassium carbonate). It is also possible to use physiologically acceptable organic bases, such as, for example, ethanolamine.

The invention also relates to the intermediate compounds of the formula I-1

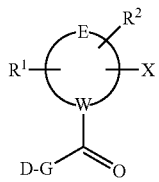

in which
D is phenyl, pyridyl, thienyl, furyl or imidazolyl, each of which is monosubstituted or disubstituted by Hal,
$R^1$ is H, OH, OA, alkyl having 1, 2, 3, 4, 5 or 6 carbon atoms or ethynyl,
$R^2$ is H, OH, OA or alkyl having 1, 2, 3, 4, 5 or 6 carbon atoms,

is pyrrolidine-1,2-diyl, piperidine-1,2-diyl, oxazolidine-3, 4- or 3,5-diyl,
G is $(CH_2)_n$, $(CH_2)_nNH$—, —CH=CH— or —CH=CH—CH=CH—;
X is COOH,
A is alkyl having 1, 2, 3, 4, 5 or 6 carbon atoms,
Hal is F, Br or I,
n is 0, 1 or 2,
and isomers and salts thereof.

Particular preference is given to compounds selected from the group consisting of
3-(4-chlorophenylcarbamoyl)oxazolidine-4-carboxylic acid,
3-(5-chlorothiophene-2-carbonyl)oxazolidine-5-carboxylic acid,
and isomers and salts thereof.

The compounds are described in Example 2.
The invention furthermore relates to the compounds.

(2R,4S)-BOC-4-ethynyl-4-hydroxypyrrolidine-2-carboxylic acid,
(2R,4R)-BOC-4-ethynyl-4-hydroxypyrrolidine-2-carboxylic acid,
alkyl(2R,4S)-BOC-4-ethynyl-4-hydroxypyrrolidine-2-carboxylate,
alkyl(2R,4R)-BOC-4-ethynyl-4-hydroxypyrrolidine-2-carboxylate,
where alkyl has 1, 2, 3, 4, 5 or 6 carbon atoms,
and isomers and salts thereof.

The preparation is described in Example 8a.
The invention also relates to the intermediate compounds of the formula I-2

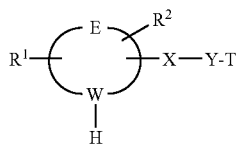

in which
$R^1$ is H, =O, $COOR^3$, OH, OA, $NH_2$, alkyl having 1, 2, 3, 4, 5 or 6 carbon atoms, $N_3$, ethynyl, vinyl, allyloxy, NHCOA, $NHSO_2A$, $OCH_2COOA$ or $OCH_2COOH$,
$R^2$ is H, OH, OA or alkyl having 1, 2, 3, 4, 5 or 6 carbon atoms,
$R^1$ and $R^2$ together are alternatively a spirocyclically bonded 3- to 6-membered carbocyclic ring,
$R^3$ is H or A,

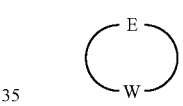

is pyrrolidine-1,2-diyl, piperidine-1,2-diyl, oxazolidine-3, 4- or 3,5-diyl,
X is CONH,
Y is 1,3- or 1,4-phenylene which is unsubstituted or monosubstituted or disubstituted by methyl, trifluoromethyl, ethyl, propyl, Cl or F,
T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, pyrazin-1-yl, azepan-1-yl or 2-azabicyclo[2.2.2]octan-2-yl, each of which is monosubstituted or disubstituted by carbonyl oxygen,
A is alkyl having 1, 2, 3, 4, 5 or 6 carbon atoms,
Hal is F, Cl, Br or I,
n is 0, 1 or 2,
and isomers and salts thereof.

The invention also relates, in particular, to the intermediate compounds of the formula I-2a

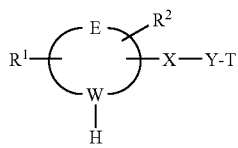

in which
$R^1$ is H, =O, $COOR^3$, OH, OA, $NH_2$, alkyl having 1, 2, 3, 4, 5 or 6 carbon atoms, $N_3$, ethynyl, vinyl, allyloxy, NHCOA, $NHSO_2A$, $OCH_2COOA$ or $OCH_2COOH$, $R^2$ is H, OH, OA or alkyl having 1, 2, 3, 4, 5 or 6 carbon atoms,
$R^3$ is H or A,

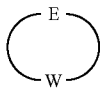

is pyrrolidine-1,2-diyl,
X is CONH,
Y is 1,3- or 1,4-phenylene which is unsubstituted or monosubstituted or disubstituted by methyl, trifluoromethyl, ethyl, propyl, Cl or F,
T is piperidin-1-yl, pyrrolidin-1-yl, 1H-pyridin-1-yl, morpholin-4-yl, 1,3-oxazolidin-3-yl, 2H-pyridazin-2-yl, pyrazin-1-yl, azepan-1-yl or 2-azabicyclo[2.2.2]octan-2-yl, each of which is monosubstituted or disubstituted by carbonyl oxygen,
A is alkyl having 1, 2, 3, 4, 5 or 6 carbon atoms,
Hal is F, Cl, Br or I,
n is 0, 1 or 2,
and isomers and salts thereof.

Particular preference is given to the compounds selected from the group consisting of
N-[4-(3-oxomorpholin-4-yl)phenyl]-(S)-pyrrolidine-2-carboxamide,
N-[4-(3-oxomorpholin-4-yl)phenyl]-(R)-pyrrolidine-2-carboxamide,
N-[4-(3-oxomorpholin-4-yl)phenyl]-(2R,4R)-4-hydroxypyrrolidine-2-carboxamide,
N-[4-(3-oxomorpholin-4-yl)phenyl]-4-hydroxypyrrolidine-2-carboxamide,
N-[4-(3-oxomorpholin-4-yl)phenyl]-(R)-4,4-dimethoxypyrrolidine-2-carboxamide,
N-[4-(3-oxomorpholin-4-yl)phenyl]-(2R,4R)-4-methoxypyrrolidine-2-carboxamide,
and isomers and salts thereof.

The preparation is described, for example, in Example 1 and 7.

Compounds of the formula I according to the invention and the compounds of Claims 24 and 25 may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds of the formula I and the compounds of Claims 24 and 25 and/or physiologically acceptable salts thereof for the preparation of a medicament (pharmaceutical preparation), in particular by non-chemical methods. They can be converted here into a suitable dosage form together with at least one solid, liquid and/or semi-liquid excipient or adjuvant and, if desired, in combination with one or more further active ingredients.

The invention furthermore relates to medicaments comprising at least one compound of the formula I or a compound of Claims 24 and 25 and/or pharmaceutically usable derivatives, solvates, salts and stereoisomers thereof, including mixtures thereof in all ratios, and, if desired, excipients and/or adjuvants.

These preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or Vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders or also as nasal sprays. The novel compounds may also be lyophilised and the resultant lyophilisates used, for example, to prepare injection preparations. The preparations indicated may be sterilised and/or comprise adjuvants, such as lubricants, preservatives, stabilisers and/or wetting agents, emulsifying agents, salts for modifying the osmotic pressure, buffer substances, colorants and flavours and/or a plurality of further active ingredients, for example one or more vitamins.

The compounds of the formula I as well as the compounds of Claims 24 and 25 and physiologically acceptable salts thereof can be used for combating and preventing thromboembolic diseases, such as thromboses, myocardial infarction, arteriosclerosis, inflammation, apoplexy, angina pectoris, restenosis after angioplasty, claudicatio intermittens, migraine, tumours, tumour diseases and/or tumour metastases.

In general, the substances according to the invention are preferably administered in doses between about 1 and 500 mg, in particular between 5 and 100,mg, per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

The invention furthermore relates to medicaments comprising at least one compound of the formula I or a compound of Claims 24 and 25 and/or pharmaceutically usable derivatives, solvates, salts and stereoisomers thereof, including mixtures thereof in all ratios, and at least one further medicament active ingredient.

The invention also relates to a set (kit) consisting of separate packs of
(a) an effective amount of a compound of the formula I or a compound of Claims 24 and 25 and/or pharmaceutically usable derivatives, solvates, salts and stereoisomers thereof, including mixtures thereof in all ratios,
and
(b) an effective amount of a further medicament active ingredient.

The set comprises suitable containers, such as boxes, individual bottles, bags or ampoules. The set may, for example, comprise separate ampoules each containing an effective amount of a compound of the formula I or one of the compounds of Claims 24 and 25 and/or pharmaceutically usable derivatives, solvates and stereoisomers thereof, including mixtures thereof in all ratios,
and an effective amount of a further medicament active ingredient in dissolved or lyophilised form.

The invention furthermore relates to the use of compounds of the formula I and the compounds of Claims 24 and 25 and/or pharmaceutically usable derivatives, solvates, salts and stereoisomers thereof, including mixtures thereof in all ratios, for the preparation of a medicament for the treatment of thromboses, myocardial infarction, arteriosclerosis, inflammation, apoplexy, angina pectoris, restenosis after angioplasty, claudicatio intermittens, migraine, tumours, tumour diseases and/or tumour metastases,
in combination with at least one further medicament active ingredient.

The invention furthermore relates to a medicament comprising 1-N-[(4-chlorophenyl)]-2-N-{[4-(3-oxomorpholin-4-yl))phenyl]}-(2R,4R)-4-hydroxy-pyrrolidine-1,2-dicarboxamide and/or pharmaceutically usable derivatives, solvates, salts and stereoisomers thereof, including mixtures thereof in all ratios, and aspirin.

The invention furthermore relates to the use of 1-N-[(4-chlorophenyl)]-2-N-{[4-(3-oxomorpholin-4-yl)phenyl]}-(2R,4R)-4-hydroxypyrrolidine-1,2-dicarboxamide and/or pharmaceutically usable derivatives, solvates, salts and stereoisomers thereof, including mixtures thereof in all ratios, for the preparation of a medicament for the treatment of thromboses, myocardial infarction, arteriosclerosis, inflammation, apoplexy, angina pectoris, restenosis after angioplasty, claudicatio intermittens, migraine, tumours, tumour diseases and/or tumour metastases, in combination with aspirin.

Above and below, all temperatures are given in ° C. In the following examples, 'conventional work-up' means that water is added if necessary, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent:ethyl acetate/methanol 9:1.
Mass spectrometry (MS): EI (electron impact ionisation) M$^+$
FAB (fast atom bombardment) (M+H)$^+$
ESI (electrospray ionisation) (M+H)$^+$ (unless stated otherwise)

EXAMPLE 1

1-N-[(4-chlorophenyl)]-2-N-{[4-(3-oxomorpholin-4-yl)phenyl]}-(R)-pyrrolidine-1,2-dicarboxamide ("A1") is prepared analogously to the following scheme

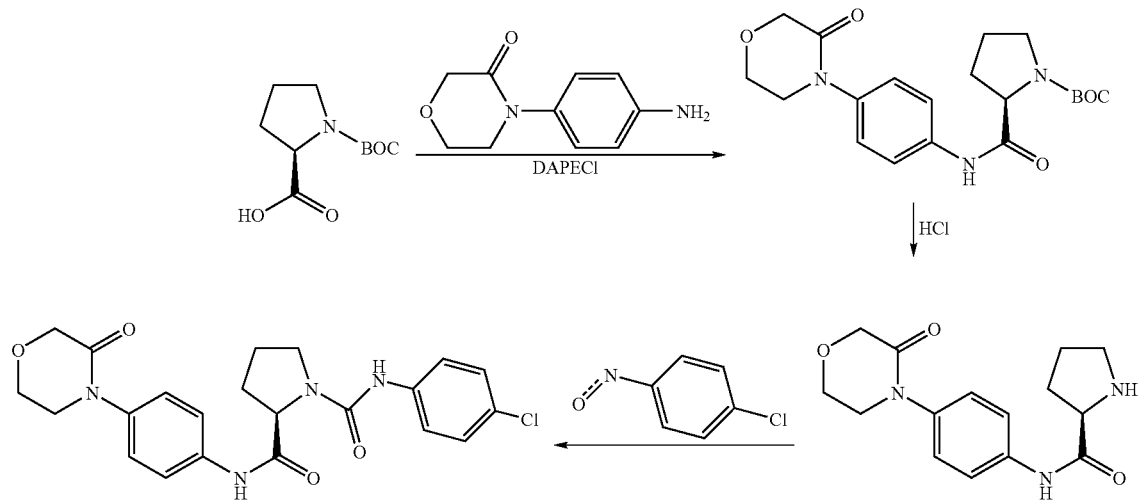

1.1 0.8 g (5.2 mmol) of 1-hydroxybenzotriazole hydrate, 1.12 g (5.2 mmol) of D-Boc-proline, 2 g (10.4 mmol) of N-(3-dimethylamino-propyl)-N'-ethylcarbodiimide hydrochloride (DAPECI) and 1.26 ml of N-methylmorpholine are added successively to a solution of 1.0 g (5.2 mmol) of 4-(4-aminophenyl)morpholin-3-one in 25 ml of dimethylformamide, and the resultant solution is stirred at room temperature for 12 hours. The reaction solution is subsequently evaporated to dryness under reduced pressure, the residue is taken up in 10 ml of 5% sodium hydrogencarbonate solution, and the sodium hydrogencarbonate solution is extracted twice with 10 ml of ethyl acetate each time. After the combined organic phases have been dried over sodium sulfate and the solvent has been stripped off, the solid residue is triturated with 20 ml of diethyl ether, giving 1.4 g of tert-butyl 2-[4-(3-oxomorpholin-4-yl)phenylcarbamoyl]pyrrolidine-1-carboxylate as a white powder; ESI 390.
1.2 40 ml of 4N hydrochloric acid in dioxane are added to a solution of 1.4 g (3.60 mmol) of tert-butyl 2-[4-(3-oxomorpholin-4-yl)phenylcarbamoyl]pyrrolidine-1-carboxylate in 20 ml of dioxane, and the mixture is stirred at room temperature for 12 hours. The precipitate is subsequently filtered off with suction and washed successively with 10 ml of dioxane and 10 ml of diethyl ether and dried under reduced pressure, giving 1.1 g of N-[4-(3-oxomorpholin-4-yl)phenyl]pyrrolidine-2-carboxamide hydrochloride as a white powder; ESI 290.

1.3 95 mg (0.61 mmol) of 4-chlorophenyl isocyanate are added to a solution of 200 mg (0.61 mmol) of N-(4-(3-oxomorpholin-4-yl)phenyl]pyrrolidine-2-carboxamide hydrochloride and 1 ml of triethylamine in 5 ml of methylene chloride, and the reaction solution is stirred at room temperature for two hours. The reaction solution is subsequently washed with 5 ml of 1N hydrochloric acid and 5 ml of water, and the methylene chloride solution is dried over sodium sulfate. After the solvent has been stripped off under reduced pressure, the crude product is recrystallised from ethanol/diethyl ether, giving 120 mg of the title compound ("A1") as a white powder; ESI 443; m.p. 227.6°.

The following compounds are obtained analogously
1-N-[(4-chlorophenyl)]-2-N-{[3-methyl-4-(3-oxomorpholin-4-yl)-phenyl]}-(R)-pyrrolidine-1,2-dicarboxamide, ESI 457, m.p. 147° (decomposition);
1-N-[(4-chlorophenyl)]-2-N-{[3-fluoro-4-(3-oxomorpholin-4-yl)phenyl]}-(R)-pyrrolidine-1,2-dicarboxamide, ESI 461, m.p. 155°;
1-N-[(4-chlorophenyl)]-2-N-{[2-fluoro-4-(3-oxomorpholin-4-yl)phenyl]}-(R)-pyrrolidine-1,2-dicarboxamide, ESI 461;
1-N-[(4-chlorophenyl)]-2-N-{[3-trifluoromethyl-4-(3-oxomorpholin-4-yl)-phenyl]}-(R)-pyrrolidine-1,2-dicarboxamide; ESI 511, m.p. 147°;
1-N-[(4-chlorophenyl)]-2-N-{[3-methyl-4-(3-oxomorpholin-4-yl)-phenyl]}-(R)-piperidine-1,2-dicarboxamide, ESI 471, m.p. 140°;
1-N-[(4-chlorophenyl)]-2-N-{[4-(2-oxo-2H-pyridin-1-yl) phenyl]}-(R)-pyrrolidine-1,2-dicarboxamide, m.p. 221°;
1-N-[(4-chlorophenyl)]-2-N-{[4-(2-oxo-2H-pyrazin-1-yl) phenyl]}-(R)-pyrrolidine-1,2-dicarboxamide, ESI 438, m.p. 227°;
1-N-[(4-chlorophenyl)]-2-N-{[3-methyl-4-(3-oxomorpholin-4-yl)-phenyl]}-(S)-pyrrolidine-1,2-dicarboxamide, ESI 457; m.p. 174°;
1-N-[(4-chlorophenyl)]-2-N-{[4-(2-oxo-2H-pyridin-1-yl) phenyl]}-4,4-difluoro-(R)-pyrrolidine-1,2-dicarboxamide, ESI 473;
1-N-[(4-chlorophenyl)]-2-N-{[2-fluoro-4-(2-oxo-2H-pyridin-1-yl)-phenyl]}-(R)-pyrrolidine-1,2-dicarboxamide, ESI 455;
1-N-[(4-chlorophenyl)]-2-N-{[4-(2-oxo-3-methoxy-2H-pyridin-1-yl)-phenyl]}-(R)-pyrrolidine-1,2-dicarboxamide, ESI 467.

EXAMPLE 1a

N-[4-(3-oxomorpholin-4-yl)phenyl]-(R)-1-(5-chlorothiophene-2-carbonyl)-pyrrolidine-2-carboxamide ("AB1")

0.71 g (4.66 mmol) of 1-hydroxybenzotriazole hydrate, 0.76 g (4.66 mmol) of 5-chlorothiophenecarboxylic acid, 1.79 g (9.33 mmol) of N-(3-dimethylaminopropyl)-N'-ethylcarbodiimide hydrochloride (DAPECI) and 1.13 ml of N-methylmorpholine are added successively to a solution of 1.35 g (4.66 mmol) of N-[4-(3-oxomorpholin-4-yl)phenyl]pyrrolidine-2-carboxamide in 30 ml of dimethylformamide, and the resultant solution is stirred at room temperature for 12 hours. The solution is subsequently evaporated to dryness under reduced pressure, the residue is taken up in 10 ml of 5% sodium hydrogencarbonate solution, and the sodium hydrogencarbonate solution is extracted twice with 10 ml of ethyl acetate each time. After the combined organic phases have been dried over sodium sulfate and the solvent has been stripped off, the solid residue is triturated with 20 ml of diethyl ether, giving 1.2 g (59.4%) of "AB1", ESI 434; m.p. 195°.

The Compound
N-[3-methyl-4-(3-oxomorpholin-4-yl)phenyl]-(R)-1-(5-chlorothiophene-2-carbonyl)pyrrolidine-2-carboxamide, ESI 448; m.p. 113° (decomposition)
is obtained analogously.

EXAMPLE 1b

1-N-[(4-chlorophenyl)]-2-N-{[4-(3-oxomorpholin-4-yl) phenyl]}-(R)-2,5-dihydropyrrole-1,2-dicarboxamide is prepared as follows:

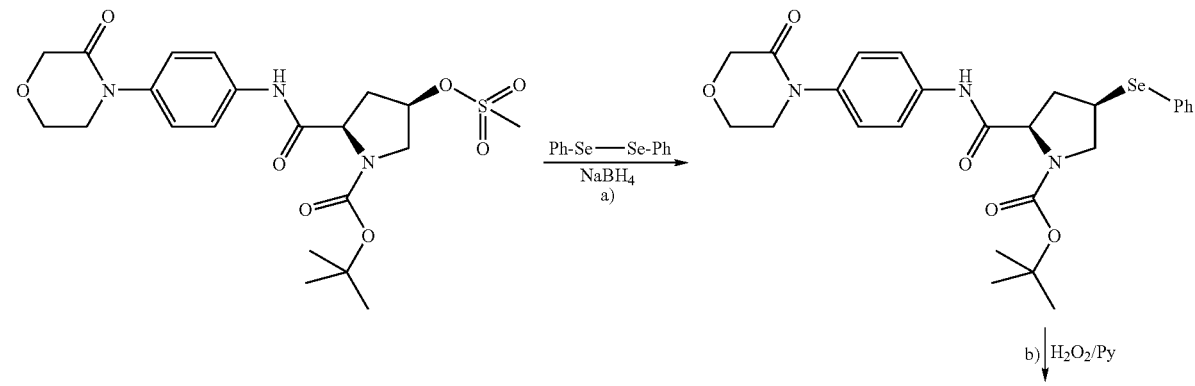

-continued

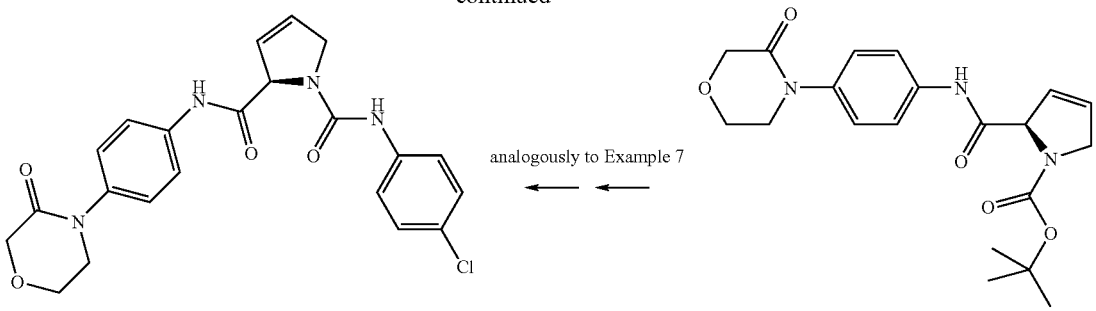

analogously to Example 7 a) 0.19 g (5.1 mmol) of sodium borohydride (NaBH$_4$) is added under nitrogen to the suspension of 0.82 g (2.63 mmol) of diphenyl diselenide in 12 ml of tert-butanol, and the reaction mixture is refluxed for about one hour until the yellow reaction solution becomes colourless. The solution of 1.99 g (4.11 mmol) of tert-butyl (2R,4R)-4-methanesulfonyloxy-2-[4-(3-oxomorpholin-4-yl)phenylcarbamoyl]pyrrolidine-1-carboxylate (see Example 9.1) in 12 ml of tert-butanol is subsequently added dropwise at this temperature, and the reaction mixture is then left to reflux for 12 hours with stirring. After the reaction mixture has been cooled, the solvent is stripped off under reduced pressure, the residue is taken up in 20 ml of ethyl acetate, and the resultant solution is washed with 20 ml of water. Drying of the ethyl acetate phase over sodium sulfate and stripping off of the solvent gives 1.82 g (81.3%) of tert-butyl (1R,4R)-2-[4-(3-oxomorpholin-4-yl)-phenylcarbamoyl]-4-phenylselanylpyrrolidine-1-carboxylate, ESI 545.

b) 1 ml of 30% hydrogen peroxide (H$_2$O$_2$) is added dropwise at 0° C. to the solution of 1.72 g (3.16 mmol) of the selenium compound prepared under a) and 0.4 ml of pyridine in 25 ml of methylene chloride. The reaction mixture is subsequently allowed to come to room temperature over the course of two hours, 10 ml of 5% potassium hydrogensulfate solution are then added, the phases are separated, and the organic phase is washed with 10 ml of saturated sodium hydrogencarbonate solution. After the organic phase has been dried over sodium sulfate and the solvent has been stripped off, the residue is chromatographed on silica gel, giving 0.73 g (59.7%) of tert-butyl (R)-2-[4-(3-oxomorpholin-4-yl)phenylcarbamoyl]-2,5-dihydropyrrole-1-carboxylate, ESI 388.

The further reaction is carried out analogously to Example 7, giving 1-N-[(4-chlorophenyl)]-2-N-{[4-(3-oxomorpholin-4-yl)phenyl]}-(R)-2,5-dihydropyrrole-1,2-dicarboxamide, ESI 441, m.p. 245°.

The following compounds are obtained analogously
1-N-[(4-chlorophenyl)]-2-N-{[4-(2-oxo-1H-pyrazin-1-yl) phenyl]}-(R)-2,5-dihydropyrrole-1,2-dicarboxamide,
1-N-[(4-chlorophenyl)]-2-N-{[4-(2-oxo-1H-pyridin-1-yl) phenyl]}-(R)-2,5-dihydropyrrole-1,2-dicarboxamide,
1-N-[(4-chlorophenyl)]-2-N-{[3-fluoro-4-(3-oxomorpholin-4-yl)phenyl]}-(R)-2,5-dihydropyrrole-1,2-dicarboxamide,
1-N-[(4-chlorophenyl)]-2-N-{[2-fluoro-4-(3-oxomorpholin-4-yl)phenyl]}-(R)-2,5-dihydropyrrole-1,2-dicarboxamide.

EXAMPLE 2

3-N-[(4-chlorophenyl)]-4-N-{[4-(3-oxomorpholin-4-yl) phenyl]}-(R)-oxazolidine-3,4-dicarboxamide ("A2") is prepared analogously to the following scheme:

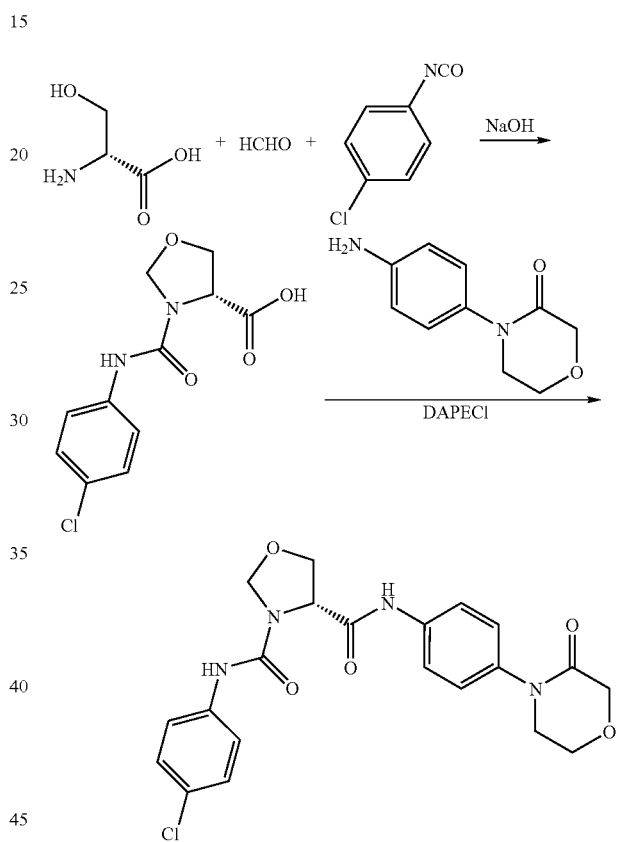

2.1 1.49 ml (20.0 mmol) of 37% aqueous formaldehyde solution are added to a solution of 2.10 g (20.0 mmol) of D-serine in 10 ml of 1N aqueous sodium hydroxide solution. The resultant solution is left at 5° C. for 18 hours. The solution is heated to 80° C., 6.14 g (40 mmol) of 4-chlorophenyl isocyanate are added, and the mixture is stirred at this temperature for one hour. The mixture is allowed to cool, and the precipitate formed is filtered off. The filtrate is acidified using 1N HCl, and the precipitate formed is filtered off and dried, giving (R)-3-(4-chlorophenylcarbamoyl)oxazolidine-4-carboxylic acid as a colourless solid; ESI 271.

2.2 498 mg (2.60 mmol) of N-(3-dimethylaminopropyl)-N'-ethylcarbodiimide hydrochloride (DAPECI) are added to a solution of 541 mg (2.00 mmol) of (R)-3-(4-chlorophenylcarbamoyl)oxazolidine-4-carboxylic acid and 384 mg (2.00 mmol) of 4-(4-aminophenyl)morpholin-3-one in 4 ml of dimethylformamide (DMF), and the mixture is stirred at room temperature for 18 hours. The reaction mixture is added to saturated sodium hydrogencarbonate solution, and the precipitate formed is filtered off, giving 3-N-[(4-chlorophenyl)]-4-N-{[4-(3-oxomorpholin-4-yl)phenyl]}-(R)-oxazolidine-3, 4-dicarboxamide ("A2") as a colourless solid; ESI 461.

The following compounds are obtained analogously
3-N-[(4-chlorophenyl)]-4-N-}[3-methyl-4-(3-oxomorpholin-4-yl)-phenyl]}-(R)-oxazolidine-3,4-dicarboxamide, ESI 459;
3-N-[(4-chlorophenyl)]-4-N-{[4-(3-oxomorpholin-4-yl)phenyl]}-(4R,5S)-5-methyloxazolidine-3,4-dicarboxamide, ESI 459;
3-N-[(4-chlorophenyl)-4-N-{[3-methyl-4-(3-oxomorpholin-4-yl)phenyl]}-(4R,5S)-5-methyloxazolidine-3,4-dicarboxamide, ESI 473;
3-N-[(4-chlorophenyl)]-4-N-{[4-(2-oxo-2H-pyridin-1-yl)phenyl]}-(R)-oxazolidine-3,4-dicarboxamide, ESI 439;
3-N-[(4-chlorophenyl)]-4-N-{[4-(2-oxo-2H-pyridin-1-yl)phenyl]}-(4R,5S)-5-methyloxazolidine-3,4-dicarboxamide, ESI 453;
3-N-[4-chlorophenyl)]-4-N-{[3-fluoro-4-(3-oxomorpholin-4-yl)phenyl]}-(4R,5S)-5-methyloxazolidine-3,4-dicarboxamide, ESI 477;
3-N-[(4-chlorophenyl)]-4-N-{[3-chloro-4-(3-oxomorpholin-4-yl)phenyl]}-(4R,5S)-5-methyloxazolidine-3,4-dicarboxamide, ESI 477;
3-N-[(4-chlorophenyl)]-4-N-{[3-methyl-4-(3-oxomorpholin-4-yl)-phenyl]}-(4R,5R)-5-methyloxazolidine-3,4-dicarboxamide, ESI 473;
3-N-[(4-chlorophenyl)]-4-N-{[4-(2-oxo-2H-pyrazin-1-yl)phenyl]}-(4R,5S)-5-methyloxazolidine-3,4-dicarboxamide, ESI 454;
3-N-[(4-chlorophenyl)]-4-N-{[4-(2-oxo-2H-pyrazin-1-yl)phenyl]}-(R)-oxazolidine-3,4-dicarboxamide, ESI 440;
3-N-[(4-chlorophenyl)]-4-N-{[3-chloro-4-(2-oxo-2H-pyridin-1-yl)-phenyl]}-(R)-oxazolidine-3,4-dicarboxamide, ESI 473.

EXAMPLE 2a

An analogous procedure to Example 2 starting from (R)-cleonine

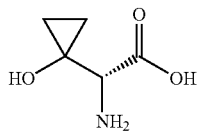

gives the following compound
6-N-[(4-chlorophenyl)]-7-N-{[4-(3-oxomorpholin-4-yl)phenyl]}-4-oxa-6-azaspiro[2.4]heptane-6,7-dicarboxamide

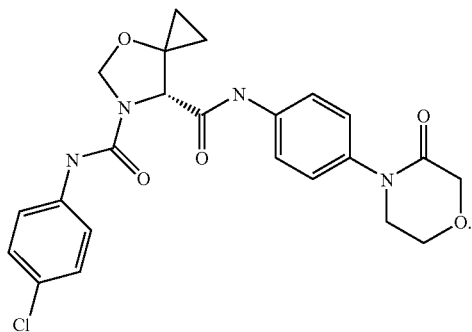

EXAMPLE 3

3-N-[(4-chlorophenyl)]-4-N-{[4-(3-oxomorpholin-4-yl)phenyl]}-(S)-thiazolidine-3,4-dicarboxamide ("A3") and
3-N-[(4-chlorophenyl)]-4-N-{[4-(3-oxomorpholin-4-yl)phenyl]}-(S)-1,1-dioxo-1$\lambda^6$-thiazolidine-3,4-dicarboxamide ("A4") are prepared analogously to the following scheme:

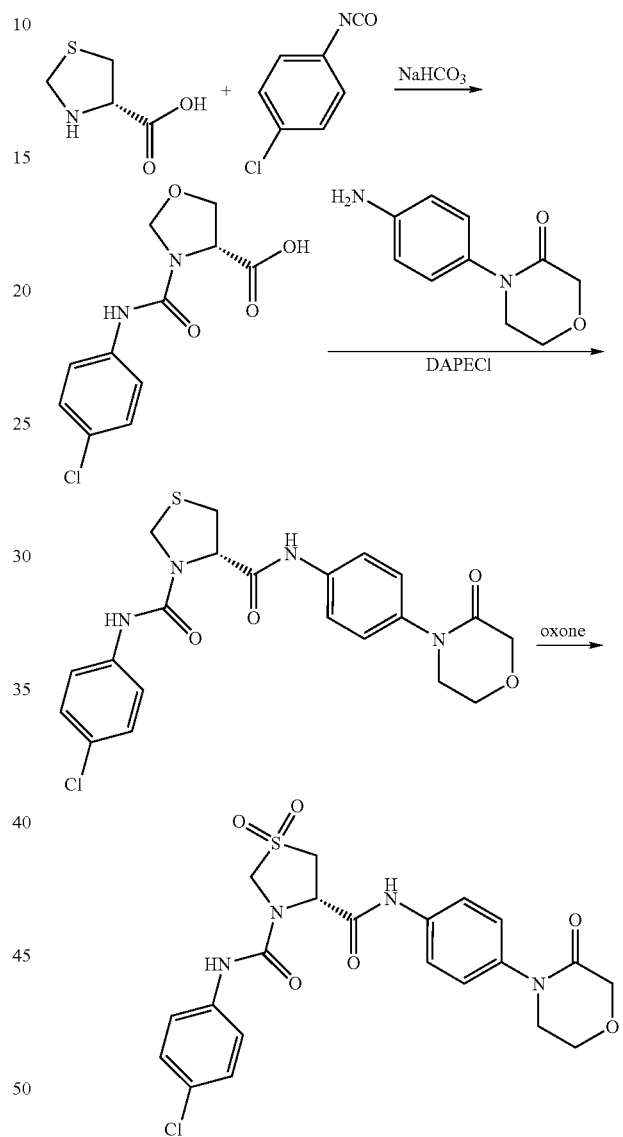

3.1 A solution of 4.54 g (54.0 mmol) of sodium hydrogencarbonate and 3.60 g (27.0 mmol) of 2-(S)-thiazolidine-4-carboxylic acid in 50 ml of water is heated to 80° C., and 8.46 g (54.0 mmol) of 4-chlorophenyl isocyanate are added. The reaction mixture is stirred at this temperature for 1 hour. The mixture is allowed to cool, and the precipitate formed is filtered off. The filtrate is acidified using 1N HCl, and the precipitate formed is filtered off and dried, giving (S)-3-(4-chlorophenylcarbamoyl)thiazolidine-4-carboxylic acid as a colourless solid; ESI 287.

3.2 498 mg (2.60 mmol) of N-(3-dimethylaminopropyl)-N'-ethylcarbodiimide hydrochloride (DAPECI) are added to a solution of 573 mg (2.00 mmol) of (S)-3-(4-chlorophenylcarbamoyl)thiazolidine-4-carboxylic acid and 384 mg (2.00 mmol) of 4-(4-aminophenyl)morpholin-3-one in 4 ml of dimethylformamide (DMF), and the mixture is stirred at room temperature for 18 hours. The reaction mixture is added to saturated sodium hydrogencarbonate solution, and the precipitate formed is filtered off, giving 3-N-[(4-chlorophenyl)]-4-N-{[4-(3-oxomorpholin-4-yl)phenyl]}-(S)-thiazolidine-3,4-dicarboxamide ("A3") as a colourless solid; ESI 461.

3.3 A solution of 1.9 g of oxone in 30 ml of water is added to a suspension of 450 mg (0.976 mmol) of "A3" in 50 ml of methanol, and the reaction mixture is stirred at room temperature for 24 hours. The reaction mixture is added to water, and the precipitate formed is filtered off and dried, giving 3-N-[(4-chlorophenyl)]-4-N-{[4-(3-oxomorpholin-4-yl)phenyl]}-(S)-1,1-dioxo-1$\lambda^6$-thiazolidine-3,4-dicarboxamide ("A4") as a colourless solid; ESI 493.

The following compounds are obtained analogously
3-N-[(4-chlorophenyl)]-4-N-{[3-methyl-4-(3-oxomorpholin-4-yl)-phenyl]}-(S)-thiazolidine-3,4-dicarboxamide, ESI 475;
3-N-[(4-chlorophenyl)]-4-N-{[3-methyl-4-(3-oxomorpholin-4-yl)-phenyl]}-(S)-1,1-dioxo-1$\lambda^6$-thiazolidine-3,4-dicarboxamide, ESI 507;
3-N-[(4-chlorophenyl)]-4-N-{[4-(2-oxo-2H-pyridin-1-yl)phenyl]}-(R)-thiazolidine-3,4-dicarboxamide, ESI 455.

EXAMPLE 4

N-[4-(3-oxomorpholin-4-yl)phenyl]-3-(5-chlorothiophene-2-carbonyl)-oxazolidine-5-carboxamide ("A5") is prepared analogously to the following scheme:

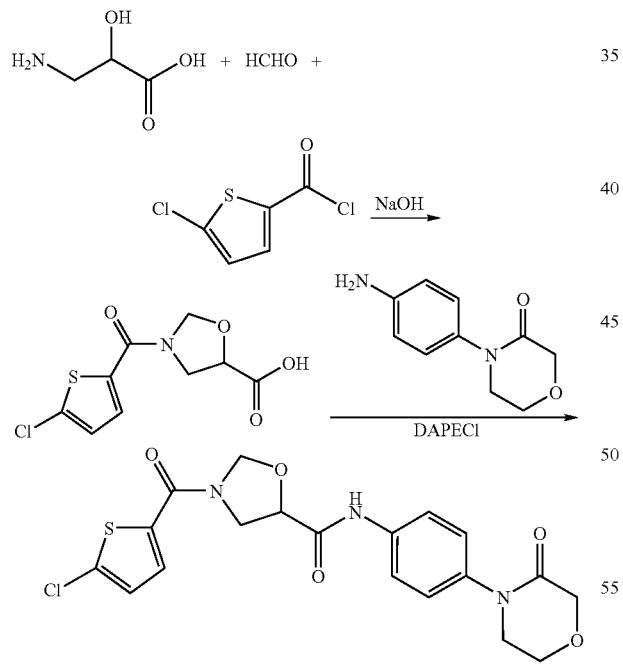

4.1 1.48 ml (19.9 mmol) of 37% aqueous formaldehyde solution are added to a solution of 2.00 g (19.0 mmol) of DL-isoserine in 10 ml of 1N aqueous sodium hydroxide solution. The resultant solution is left at 5° C. for 18 hours. A solution of 3.46 g (19.1 mmol) of 5-chlorothiophenecarbonyl chloride in 10 ml of acetone is added dropwise to this solution at an internal temperature of 0-5° C. During the dropwise addition, the pH is held at a value above 7 by addition of solid sodium hydrogencarbonate. When the addition is complete, the mixture is allowed to warm to room temperature, water is added, and the mixture is extracted with tert-butyl methyl ether. The aqueous phase is acidified using 1N HCl and extracted with tert-butyl methyl ether. This organic phase is dried over sodium sulfate and evaporated, giving 3-(5-chlorothiophene-2-carbonyl)oxazolidine-5-carboxylic acid as a colourless solid; ESI 262.

4.2 479 mg (2.50 mmol) of N-(3-dimethylaminopropyl)-N'-ethyl-carbodiimide hydrochloride (DAPECI) are added to a solution of 500 mg (1.91 mmol) of 3-(5-chlorothiophene-2-carbonyl)oxazolidine-5-carboxylic acid and 367 mg (1.91 mmol) of 4-(4-aminophenyl)morpholin-3-one in 5 ml of dimethylformamide (DMF), and the mixture is stirred at room temperature for 18 hours. The reaction mixture is added to saturated sodium hydrogencarbonate solution, and the precipitate formed is filtered off, giving N-[4-(3-oxomorpholin-4-yl)phenyl]-3-(5-chlorothiophene-2-carbonyl)oxazolidine-5-carboxamide ("A5") as a colourless solid; ESI 436.

The following compounds are obtained analogously
N-[3-methyl-4-(3-oxomorpholin-4-yl)phenyl]-3-(5-chlorothiophene-2-carbonyl)oxazolidine-5-carboxamide, ESI 450;
N-[4-(2-oxo-2H-pyridin-1-yl)phenyl]-3-(5-chlorothiophene-2-carbonyl)oxazolidine-5-carboxamide, ESI 430.

EXAMPLE 5

1-N-[(5-chloropyridin-2-yl)]-2-N-{[4-(2-oxo-2H-pyridin-1-yl)phenyl]}-(2R,4R)-4-hydroxypyrrolidine-1,2-dicarboxamide ("A6") is prepared analogously to the following scheme:

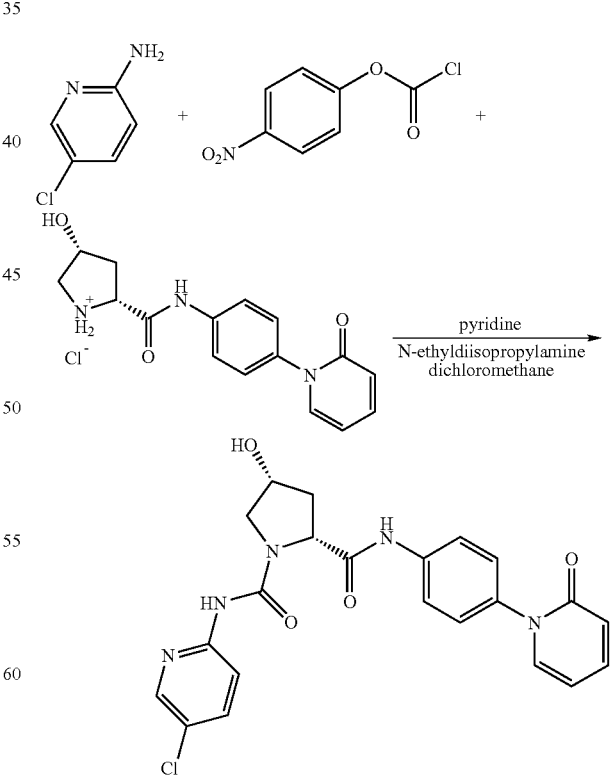

894 mg (4.43 mmol) of 4-nitrophenyl chloroformate are added to a solution of 570 mg (4.43 mmol) of 2-amino-5- chloropyridine and 0.73 ml (9.0 mmol) of pyridine in 50 ml of dichloromethane, and the mixture is stirred at room temperature for 1 hour. 1.49 g (4.43 mmol) of (2R,4R)-4-hydroxy-2-[4-(2-oxo-2H-pyridin-1-yl)phenylcarbamoyl]pyrrolidinium chloride and 1.5 ml (9.0 mmol) of N-ethyldiisopropylamine are added to the resultant suspension, and the reaction mixture is stirred at room temperature for 18 hours. The reaction mixture is evaporated, and the residue is chromatographed on a silica-gel column with dichloromethane/methanol 95:5 as eluent, giving 1-N-[(5-chloropyridin-2-yl)]-2-N-{[4-(2-oxo-2H-pyridin-1-yl)phenyl]}-(2R,4R)-4-hydroxypyrrolidine-1,2-dicarboxamide ("A6") as a colourless solid, ESI 454.

The following compounds are obtained analogously

1-N-[(5-chloropyridin-2-yl)]-2-N-{[4-(3-oxomorpholin-4-yl)phenyl]}-(2R,4R)-4-hydroxypyrrolidine-1,2-dicarboxamide, ESI 460;

1-N-[(5-chloropyridin-2-yl)]-2-N-{[4-(2-oxo-2H-pyrazin-1-yl)phenyl]}-(2R,4R)-4-hydroxypyrrolidine-1,2-dicarboxamide, ESI 455;

1-N-[(5-chloropyridin-2-yl)]-2-N-{[3-fluoro-4-(2-oxo-2H-pyridin-1-yl)-phenyl]}-(2R,4R)-4-hydroxypyrrolidine-1,2-dicarboxamide, ESI 472;

1-N-[(5-chloropyridin-2-yl)]-2-N-{[4-(2-oxo-2H-pyridin-1-yl)phenyl]}-(R)-4,4-dimethoxypyrrolidine-1,2-dicarboxamide, ESI 498;

1-N-[(5-chloropyridin-2-yl)]-2-N-{[4-(3-oxomorpholin-4-yl)phenyl]}-(R)-4,4-dimethoxypyrrolidine-1,2-dicarboxamide, ESI 504;

1-N-[(6-chloropyridin-3-yl)]-2-N-{[4-(2-oxo-2H-pyridin-1-yl)phenyl]}-(2R,4R)-4-hydroxypyrrolidine-1,2-dicarboxamide, ESI 454;

1-N-[(6-chloropyridin-3-yl)]-2-N-{[4-(2-oxo-2H-pyrazin-1-yl)phenyl]}-(2R,4R)-4-hydroxypyrrolidine-1,2-dicarboxamide, ESI 455.

EXAMPLE 6

1-N-[(4-chlorophenyl)]-2-N-{[4-(2-oxo-2H-pyridin-1-yl)phenyl]}-(R)-4,4-dimethoxypyrrolidine-1,2-dicarboxamide ("A7") is prepared analogously to the following scheme:

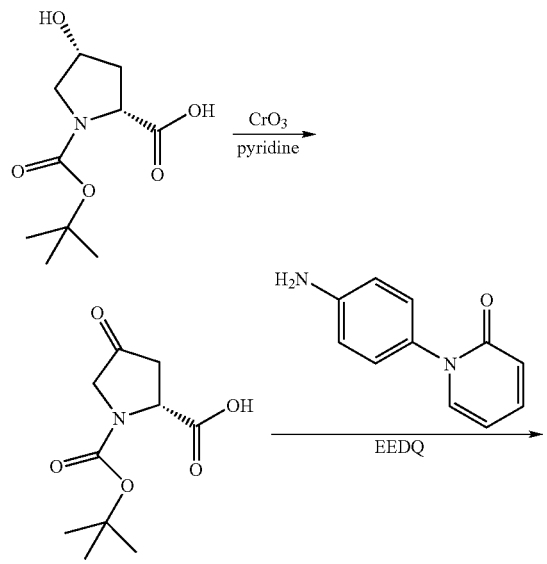

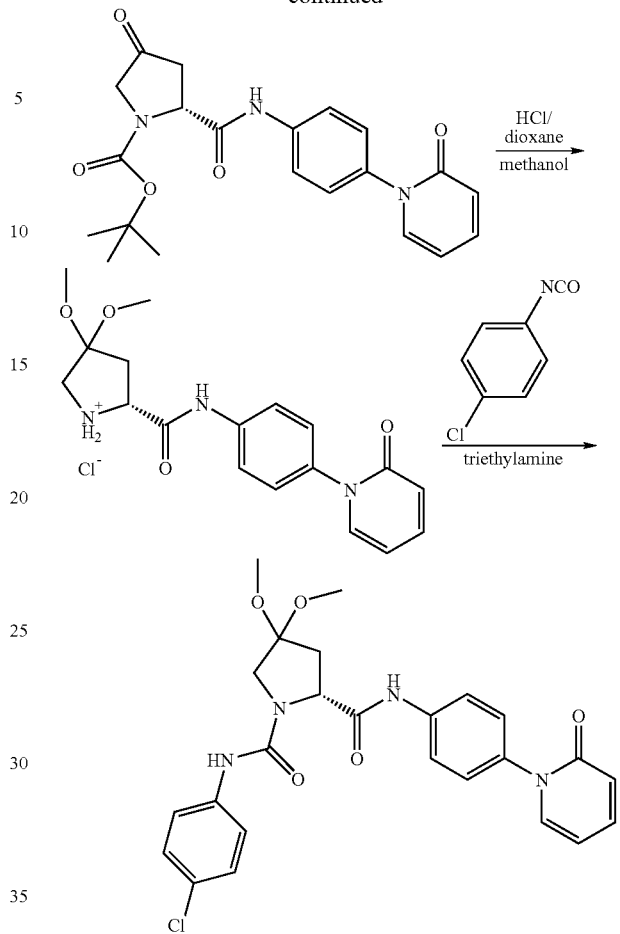

6.1 12.2 g (122 mmol) of chromium(VI) oxide are added to a mixture, held at 0° C., of 22 ml of pyridine and 50 ml of dichloromethane, and the mixture is stirred at the same temperature for 30 minutes. The solution is allowed to warm to room temperature, and a solution of 5.00 g of cis-Boc-4-hydroxy-D-proline in 80 ml of dichloromethane is added dropwise over the course of 5 minutes. After stirring at room temperature for 1 hour, the solution is filtered, and the filtrate is evaporated. The residue is partitioned between 1N HCl and tert-butyl methyl ether. The organic phase is dried over sodium sulfate, evaporated and recrystallised from diethyl ether/petroleum ether, giving Boc-4-keto-D-proline as a colourless solid; ESI 130.

6.2 742 mg (3.00 mmol) of ethyl 2-ethoxy-1,2-dihydroquinoline-1-carboxylate (EEDQ) are added to a suspension of 459 mg (2.00 mmol) of Boc-4-keto-D-proline and 372 mg (2.00 mmol) of 1-(4-aminophenyl)-1H-pyridin-2-one in 25 ml of toluene, and the mixture is stirred at room temperature for 18 hours. 200 ml of tert-butyl methyl ether are added, and the precipitate formed is filtered off. 200 ml of petroleum ether are added to the filtrate, and the resultant precipitate is filtered off, giving tert-butyl (R)-4-oxo-2-[4-(2-oxo-2H-pyridin-1-yl)phenylcarbamoyl]pyrrolidine-1-carboxylate as a brownish solid; ESI 398.

6.3 10 ml of methanol are added to a suspension of 400 mg (1.01 mmol) of tert-butyl (R)-4-oxo-2-[4-(2-oxo-2H-pyridin-1-yl)phenyl-carbamoyl]pyrrolidine-1-carboxylate in 5 ml of 4N HCl in dioxane, and the mixture is stirred at room temperature for one hour. The reaction mixture is evaporated, giving (R)-4,4-dimethoxy-2-[4-(2-oxo-2H-pyridin-1-yl) phenyl-carbamoyl]pyrrolidinium chloride as a brownish solid; ESI 344.

6.4 0.12 ml of triethylamine and 127 mg (0.830 mmol) of 4-chloro-phenyl isocyanate are added to a solution of 250 mg (0.658 mmol) of (R)-4,4-dimethoxy-2-[4-(2-oxo-2H-pyridin-1-yl)phenylcarbamoyl]pyrrolidinium chloride in 10 ml of dichloromethane. After stirring at room temperature for one hour, the reaction mixture is evaporated, and the residue is chromatographed on a silica-gel column with dichloromethane/methanol 95:5 as eluent, giving 1-N-[(4-chlorophenyl)]-2-N-{[4-(2-oxo-2H-pyridin-1-yl)phenyl]}-(R)-4,4-dimethoxypyrrolidine-1,2-dicarboxamide ("A7") as a colourless solid; ESI 497.

EXAMPLE 7

1-N-[(4-chlorophenyl)]-2-N-{[4-(3-oxomorpholin-4-yl) phenyl]}-(2R,4R)-4-hydroxypyrrolidine-1,2-dicarboxamide ("A8") is prepared analogously to the following scheme:

and 5.4 ml of triethylamine are added with cooling in an ice bath. The solution of 5.96 g (38.83 mmol) of 4-chloro-phenyl isocyanate in 100 ml of dichloroethane is subsequently added dropwise to the mixture at 2° C. over the course of 1.5 hours, and the reaction solution is then left to stir for a further 30 minutes with ice cooling. The dichloromethane solution, is then washed successively with 100 ml of 1N hydrochloric acid and 100 ml of water and dried over sodium sulfate. After the drying agent has been filtered off and the methylene chloride solution has been evaporated to ⅓ of the original volume in a rotary evaporator, the precipitated product is filtered off, washed with 50 ml of petroleum ether and dried in a desiccator, giving 14.6 g (86%) of 1-N-[(4-chlorophenyl)]-2-N-{[4-(3-oxomorpholin-4-yl)phenyl]}-(2R,4R)-4-hydroxy-pyrrolidine-1,2-dicarboxamide ("A8") as a white powder, ESI 459; m.p. 216°.

The following compounds are obtained analogously
1-N-[(4-chlorophenyl)]-2-N-{[3-methyl-4-(3-oxomorpholin-4-yl)-phenyl]}-(2R,4R)-4-hydroxypyrrolidine-1,2-dicarboxamide, ESI 473; m.p. 250°;

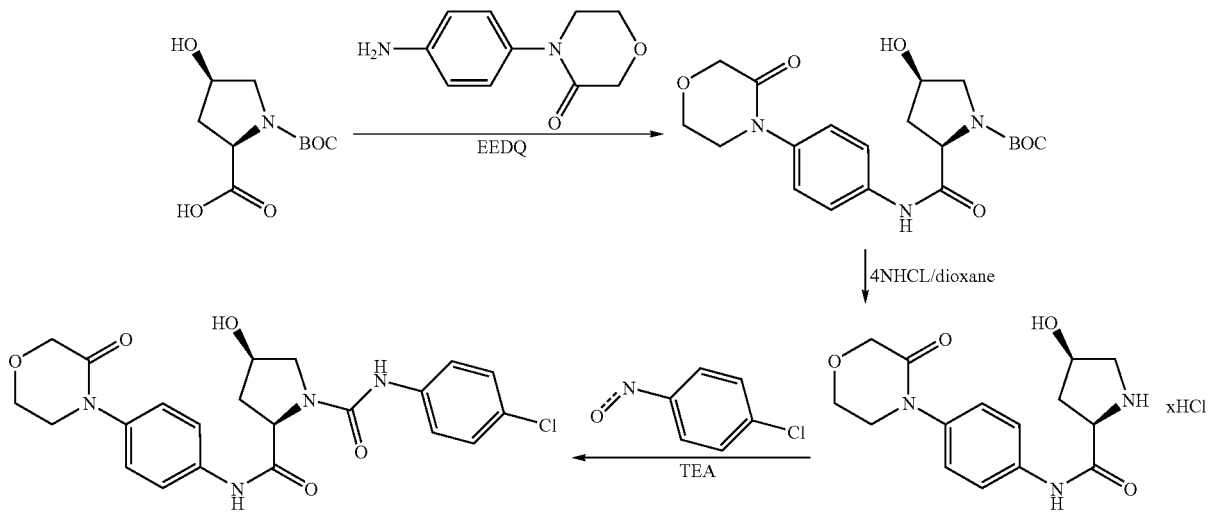

7.1 16 g (12.86 mmol) of ethyl 2-ethoxy-1,2-dihydroquinoline-1-carboxylate (EEDQ) are added to a suspension of 15 g (64.86 mmol) of cis-N'-BOC-4-hydroxy-D-proline and 12.47 g (64.86 mmol of 1-(4-amino-phenyl)-1H-pyridin-2-one in 250 ml of toluene, and the mixture is stirred at room temperature for 18 hours. The precipitated product is subsequently filtered off, washed successively with 50 ml of toluene and 50 ml of diethyl ether and dried in a desiccator, giving 24.5 g (93.2%) of tert-butyl (2R,4R)-4-hydroxy-2-[4-(3-oxomorpholin-4-yl)phenylcarbamoyl]pyrrolidine-1-carboxylate as a grey-white powder. ESI 406.

7.2 300 ml of 4N hydrochloric acid in dioxane are added to a solution of 15 g (37 mmol) of tert-butyl (2R,4R)-4-hydroxy-2-[4-(3-oxomorpholin-4-yl)phenylcarbamoyl]pyrrolidine-1-carboxylate in 200 ml of dioxane, and the mixture is stirred at room temperature for 12 hours. The precipitate is subsequently filtered off, washed with 50 ml of dioxane and 50 ml of diethyl ether and dried in a desiccator, giving 12.64 g (100%) of N-[4-(3-oxomorpholin-4-yl)phenyl]-(2R,4R)-4-hydroxypyrrolidine-2-carboxamide hydrochloride as a white powder. ESI 306.

7.3 12.64 g (36.98 mmol) of N-[4-(3-oxomorpholin-4-yl) phenyl]-(2R,4R)-4-hydroxypyrrolidine-2-carboxamide hydrochloride are suspended in 1200 ml of dichloromethane, 1-N-[(4-chlorophenyl)]-2-N-{[4-(2-oxo-2H-pyridin-1-yl) phenyl]}-(2R,4R)-4-hydroxypyrrolidine-1,2-dicarboxamide, ESI 453; m.p. 160°;
1-N-[(4-chlorophenyl)]-2-N-{[2-fluoro-4-(3-oxomorpholin-4-yl)-phenyl]}-(2R,4R)-4-hydroxypyrrolidine-1,2-dicarboxamide, ESI 477; m.p. 235°;
1-N-[(4-chlorophenyl)]-2-N-{[4-(2-oxopyrazin-1-yl)phenyl]}-(2R,4R)-4-hydroxypyrrolidine-1,2-dicarboxamide, ESI 454;
1-N-[(4-chlorophenyl)]-2-N-{[2-fluoro-4-(2-oxo-2H-pyridin-1-yl)-phenyl]}-(2R,4R)-4-hydroxypyrrolidine-1,2-dicarboxamide, ESI 471;
1-N-[(4-chlorophenyl)]-2-N-{[3-fluoro-4-(3-oxomorpholin-4-yl)-phenyl]}-(2R,3R)-3-hydroxypyrrolidine-1,2-dicarboxamide,
1-N-[(4-chlorophenyl)]-2-N-([3-fluoro-4-(3-oxomorpholin-4-yl)-phenyl]}-(2R,3S)-3-hydroxypyrrolidine-1,2-dicarboxamide,
1-N-[(4-chlorophenyl)]-2-N-{[3-fluoro-4-(3-oxomorpholin-4-yl)-phenyl]}-(2R,4R)-4-hydroxypyrrolidine-1,2-dicarboxamide,
1-N-[(4-chlorophenyl)]-2-N-{[4-(2-oxo-3-methoxy-2H-pyridin-1-yl)-phenyl]}-(2R,4R)-4-hydroxypyrrolidine-1,2-dicarboxamide, ESI 483.

1-N-[(4-chlorophenyl)]-2-N-{[4-(3-oxomorpholin-4-yl)
  phenyl]}-(2S,3S)-3-hydroxypyrrolidine-1,2-dicarboxam-
  ide, ESI 459;
1-N-[(4-chlorophenyl)]-2-N-{[4-(3-oxomorpholin-4-yl)
  phenyl]}-(2S,4S)-4-hydroxypyrrolidine-1,2-dicarboxam-
  ide, ESI 459

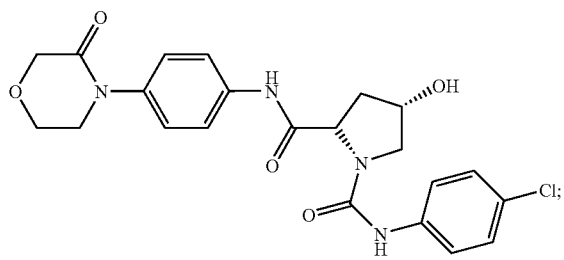

1-N-[(4-chlorophenyl)]-2-N-{[2-methoxycarbonyl-4-(3-
  oxomorpholin-4-yl)phenyl]}-(2R,4R)-3-hydroxypyrroli-
  dine-1,2-dicarboxamide, ESI 517, m.p. 119; and therefrom
  by hydrolysis
1-N-[(4-chlorophenyl)]-2-N-{[2-carboxy-4-(3-oxomorpho-
  lin-4-yl)-phenyl]}-(2R,4R)-3-hydroxypyrrolidine-1,2-di-
  carboxamide, ESI 503, m.p. 145°,
1-N-[(4-chlorophenyl)]-2-N-{[2-methoxycarbonyl-4-(3-
  oxomorpholin-4-yl)phenyl]}-(2R,4R)-4-hydroxypyrroli-
  dine-1,2-dicarboxamide, and therefrom by hydrolysis
1-N-[(4-chlorophenyl)]-2-N-{[2-carboxy-4-(3-oxomorpho-
  lin-4-yl)-phenyl]}-(2R,4R)-4-hydroxypyrrolidine-1,2-di-
  carboxamide.

EXAMPLE 8

1-N-[(4-chlorophenyl)]-2-N-{[4-(3-oxomorpholin-4-yl)
phenyl]}-(2R,4S)-4-hydroxypyrrolidine-1,2-dicarboxamide
is prepared analogously to the following scheme:

8.1 5.51 ml (35 mmol) of diethyl azodicarboxylate (DEAD)
are added dropwise at 0° C. under nitrogen to a solution of 7.0
g (7.26 mmol) of tert-butyl (2R,4R)-4-hydroxy-2-(4-(3-oxo-
morpholin-4-yl)phenylcarbamoyl]pyrrolidine-1-carboxy-
late, 5.77 g (34.5 mmol) of p-nitrobenzoic acid and 9.18 g (35
mmol) of triphenylphosphine in 350 ml of tetrahydrofuran.
The reaction mixture is subsequently left to stir at room
temperature for 12 hours and evaporated to dryness under
reduced pressure, 20 ml of methylene chloride are added to
the residue, and the methylene chloride solution is washed
successively with 10 ml of saturated sodium chloride solution
and 10 ml of water and dried over sodium sulfate. After the
drying agent has been filtered off and the solvent has been
stripped off in a rotary evaporator, the residue is triturated
with 30 ml of diethyl ether, giving 8.5 g (88.8%) of tert-butyl-
(2R,4S)-4-(4-nitrobenzoyloxy)-2-[4-(3-oxomorpholin-4-yl)
phenylcarbamoyl]pyrrolidine-1-carboxylate as slightly yel-
low crystals, ESI 555.
8.2 Analogously to Example 7, reaction of tert-butyl (2R,4S)-
4-(4-nitro-benzoyloxy)-2-[4-(3-oxomorpholin-4-yl)phenyl-
carbamoyl]pyrrolidine-1-carboxylate gives the compound
(3S,5R)-1-(4-chlorophenylcarbamoyl)-5-[4-(3-oxomorpho-
lin-4-yl)phenylcarbamoyl]pyrrolidin-3-yl 4-nitrobenzoate as
yellowish crystals, ESI 608.
8.3 0.075 ml of 1N sodium hydroxide solution is added with
ice cooling to the solution of 50 mg (0.082 mmol) of (3S,5R)-
1-(4-chlorophenyl-carbamoyl)-5-[4-(3-oxomorpholin-4-yl)
phenylcarbamoyl]pyrrolidin-3-yl 4-nitrobenzoate in 2 ml of
methanol, and the reaction mixture is stirred for 15 minutes.
The precipitate is filtered off and washed with 2 ml of metha-
nol and dried, giving 35 mg (93%) of 1-N-[(4-chlorophe-
nyl)]-2-N-{[4-(3-oxomorpholin-4-yl)phenyl]}-(2R,4S)-4-
hydroxypyrrolidine-1,2-dicarboxamide as colourless
crystals, ESI 459, m.p. 243° (decomposition).
  An analogous procedure gives
1-N-[(4-chlorophenyl)]-2-N-{[4-(3-oxomorpholin-4-yl)
  phenyl]}-(2R,3S,4R)-3,4-dihydroxypyrrolidine-1,2-di-
  carboxamide, ESI 475, m.p. 247;

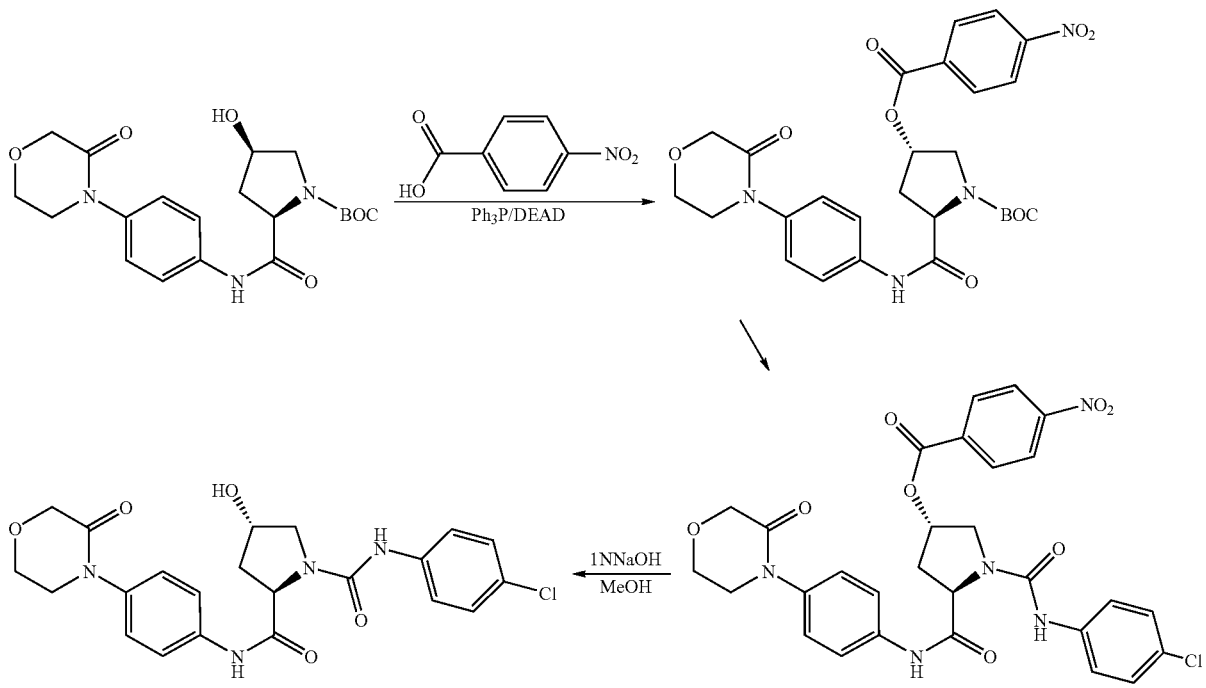

1-N-[(4-chlorophenyl)]-2-N-{[4-(3-oxomorpholin-4-yl)phenyl]}-(2S,4R)-4-hydroxypyrrolidine-1,2-dicarboxamide, ESI 459; m.p. 253°;

1-N-[(4-chlorophenyl)]-2-N-{[4-(3-oxomorpholin-4-yl)phenyl]}-3,4-dihydroxypyrrolidine-1,2-dicarboxamide.

EXAMPLE 8a

1-N-[(4-chlorophenyl)]-2-N-{[4-(3-oxomorpholin-4-yl)phenyl]}-(2R,4S)-4-ethynyl-4-hydroxypyrrolidine-1,2-dicarboxamide, ESI 483; is prepared analogously to the following scheme:

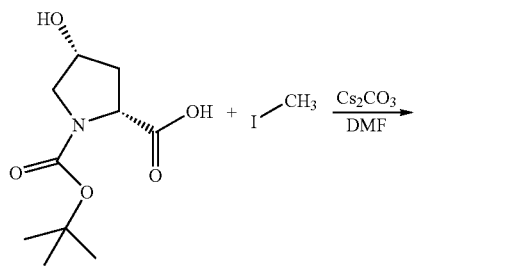

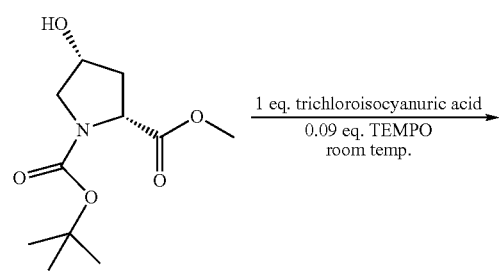

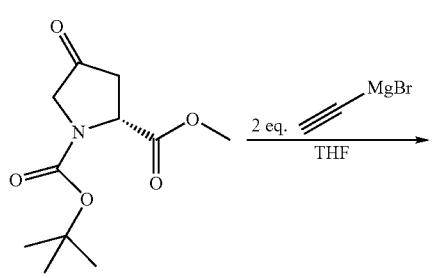

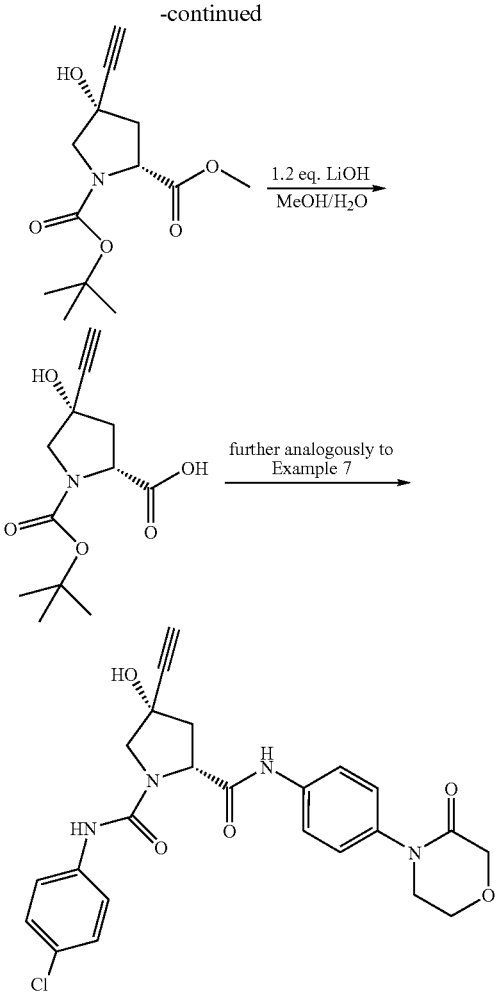

The following compounds are obtained analogously

1-N[(4-chlorophenyl)]-2-N-{[4-(2-oxo-1H-pyridin-1-yl)phenyl]}-(2R,4S)-4-ethynyl-4-hydroxypyrrolidine-1,2-dicarboxamide, ESI 477;

1-N-[(4-chlorophenyl)]-2-N-{[4-(2-oxo-2H-pyrazin-1-yl)phenyl]}-(2R,4S)-4-ethynyl-4-hydroxypyrrolidine-1,2-dicarboxamide, ESI 478.

EXAMPLE 9

1-N-[(4-chlorophenyl)]-2-N-{[4-(3-oxomorpholin-4-yl)phenyl]}-(2R,4S)-4-azidopyrrolidine-1,2-dicarboxamide ("A9") and 1-N-[(4-chlorophenyl)]-2-N-{[4-(3-oxomorpholin-4-yl)phenyl]}-(2R,4S)-4-aminopyrrolidine-1,2-dicarboxamide ("A10") are prepared analogously to the following scheme:

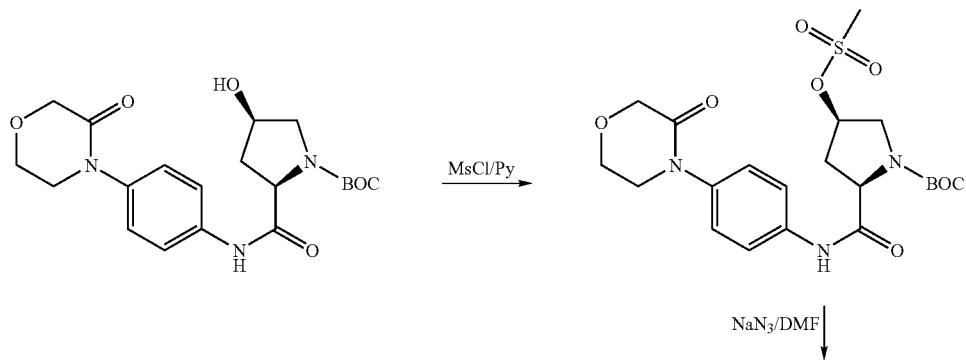

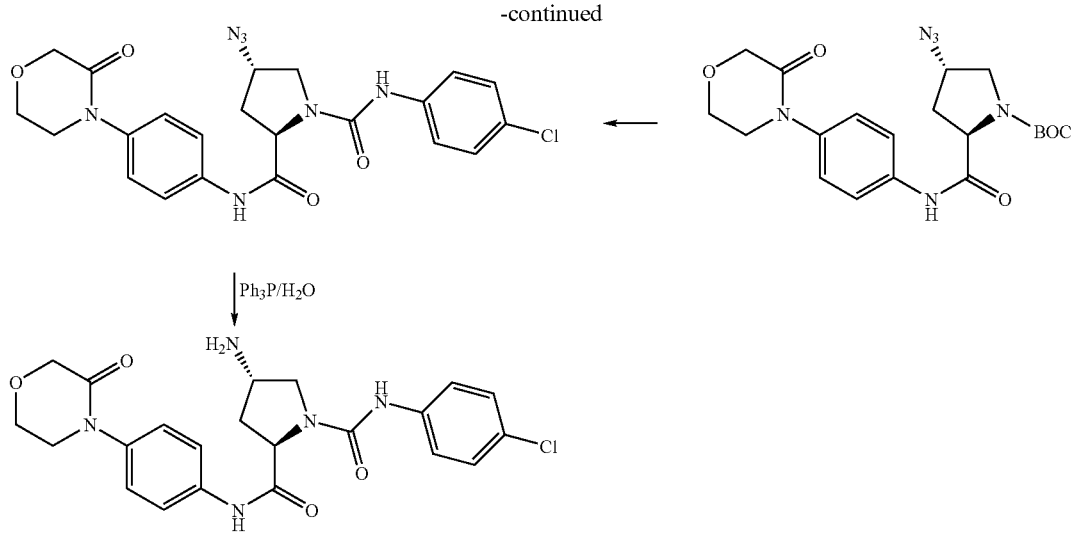

9.1 1.3 ml (16.65 mmol) of methanesulfonyl chloride are added dropwise with ice cooling to a solution of 4.5 g (11.1 mmol) of tert-butyl (2R,4R)-4-hydroxy-2-[4-(3-oxomorpholin-4-yl)phenylcarbamoyl]pyrrolidine-1-carboxylate in 20 ml of pyridine, and the reaction solution is stirred at room temperature for 12 hours. The pyridine is subsequently stripped off under reduced pressure, 10 ml of saturated citric acid solution are added to the residue, and the acidic solution is extracted twice with 10 ml of methylene chloride each time. The combined organic phases are then washed with 10 ml of saturated sodium chloride solution and dried over sodium sulfate. Removal of the drying agent by filtration and stripping-off of the solvent gives 5.4 g (100%) of tert-butyl (2R,4R)-4-methanesulfonyloxy-2-[4-(3-oxomorpholin-4-yl)phenylcarbamoyl]pyrrolidine-1-carboxylate as a yellow oil, ESI 484.

9.2 A mixture of 5.4 g (11.7 mmol) of tert-butyl (2R,4R)-4-methanesulfonyloxy-2-[4-(3-oxomorpholin-4-yl)phenylcarbamoyl]pyrrolidine-1-carboxylate and 3.69 g (56.8 mmol) of sodium azide in 50 ml of dimethylformamide (DMF) is stirred at 60° C. for 12 hours. The insoluble matter is subsequently filtered off, and the filtrate is evaporated to dryness under reduced pressure. The residue is then dissolved in 20 ml of water, and the aqueous solution is extracted twice with 10 ml of methylene chloride each time. The combined methylene chloride extracts are finally washed once with 10 ml of saturated sodium chloride solution and dried over sodium sulfate. Removal of the drying agent by filtration and stripping-off of the solvent gives 4.8 g (100%) of tert-butyl (2R,4S)-4-azido-2-[4-(3-oxomorpholin-4-yl)phenylcarbamoyl]pyrrolidine-1-carboxylate as slightly yellow crystals, ESI 431.

9.3 Analogously to Example 7, reaction of tert-butyl (2R,4S)-4-azido-2-[4-(3-oxomorpholin-4-yl)phenylcarbamoyl]pyrrolidine-1-carboxylate gives the compound 1-N-[(4-chlorophenyl)]-2-N-{[4-(8-oxomorpholin-4-yl)-phenyl]}-(2R,4S)-4-azidopyrrolidine-1,2-dicarboxamide ("A9") as a white powder, ESI 459, m.p. 145°.

9.4 A solution of 25 mg (0.052 mmol) of "A9" and 20.46 mg (0.08 mmol) of triphenylphosphine in a mixture of 0.5 ml of tetrahydrofuran and 0.5 ml of water is stirred at room temperature for 12 hours. After the precipitated triphenylphosphine oxide has been filtered off, the filtrate is evaporated to dryness, and the residue is purified by preparative HPLC (acetonitrile/water/0.1% trifluoroacetic acid), giving 12 mg (40%) of 1-N-[(4-chlorophenyl)]-2-N-{[4-(3-oxomorpholin-4-yl)phenyl]}-(2R,4S)-4-amino-pyrrolidine-1,2-dicarboxamide ("10") as colourless crystals, ESI 458.

An analogous procedure gives the compounds

1-N4-[(4-chlorophenyl)]-2-N-{[4-(3-oxomorpholin-4-yl)phenyl]}-(2R,4R)-4-azidopyrrolidine-1,2-dicarboxamide, ESI 484, m.p. 125°;

1-N-[(4-chlorophenyl)]-2-N-{[4-(3-oxomorpholin-4-yl)phenyl]}-(2R,4R)-4-aminopyrrolidine-1,2-dicarboxamide, ESI 458, m.p. 110°;

1-N-[(4-chlorophenyl)]-2-N-{[3-methyl-4-(3-oxomorpholin-4-yl)-phenyl]}-(2R,4S)-4-aminopyrrolidine-1,2-dicarboxamide, ESI 472, m.p. 218°.

Starting from the 4-amino compounds, a) reaction with acetyl chloride gives the compounds 1-N-[(4-chlorophenyl)]-2-N-{[4-(3-oxomorpholin-4-yl)phenyl]}-(2R,4S)-4-acetaminopyrrolidine-1,2-dicarboxamide, 1-N-[(4-chlorophenyl)]-2-N-{[4-(3-oxomorpholin-4-yl)phenyl]}-(2R,4R)-4-acetaminopyrrolidine-1,2-dicarboxamide, ESI 458; and analogously 1-N-[(4-chlorophenyl)]-2-N-}[3-methyl-4-(3-oxomorpholin-4-yl)-phenyl]}-(2R,4S)-4-acetaminopyrrolidine-1,2-dicarboxamide, ESI 514, m.p. 170°;

b) reaction with mesyl chloride gives the compounds

1-N-[(4-chlorophenyl)]-2-N{[4-(3-oxomorpholin-4-yl)phenyl]}-(2R,4S)-4-methylsulfonylaminopyrrolidine-1,2-dicarboxamide and 1-N-[(4-chlorophenyl)]-2-N-{[4-(3-oxomorpholin-4-yl)phenyl]}-(2R,4R)-4-methylsulfonylaminopyrrolidine-1,2-dicarboxamide;

c) reaction with butylsulfonyl chloride gives the compounds

1-N-[(4-chlorophenyl)]-2-N-{[4-(3-oxomorpholin-4-yl)phenyl]}-(2R,4R)-4-butylsulfonylaminopyrrolidine-1,2-dicarboxamide, 1-N-[(4-chlorophenyl)]-2-N-{[4-(3-oxomorpholin-4-yl)phenyl]}-(2R,4S)-4-butylsulfonylaminopyrrolidine-1,2-dicarboxamide, ESI 592;

d) reaction with isobutyryl chloride gives the compound

1-N-[(4-chlorophenyl)]-2-N-{[4-(3-oxomorpholin-4-yl)phenyl]}-(2R,4S)-4-(2-methylpropanoylamino)pyrrolidine-1,2-dicarboxamide, ESI 542; m.p. 169.

EXAMPLE 10

1-N-[(4-chlorophenyl)]-2-N-{[4-(3-oxomorpholin-4-yl)phenyl]}-(2R,4R)-4-methoxypyrrolidine-1,2-dicarboxamide ("A11") is prepared analogously to the following scheme:

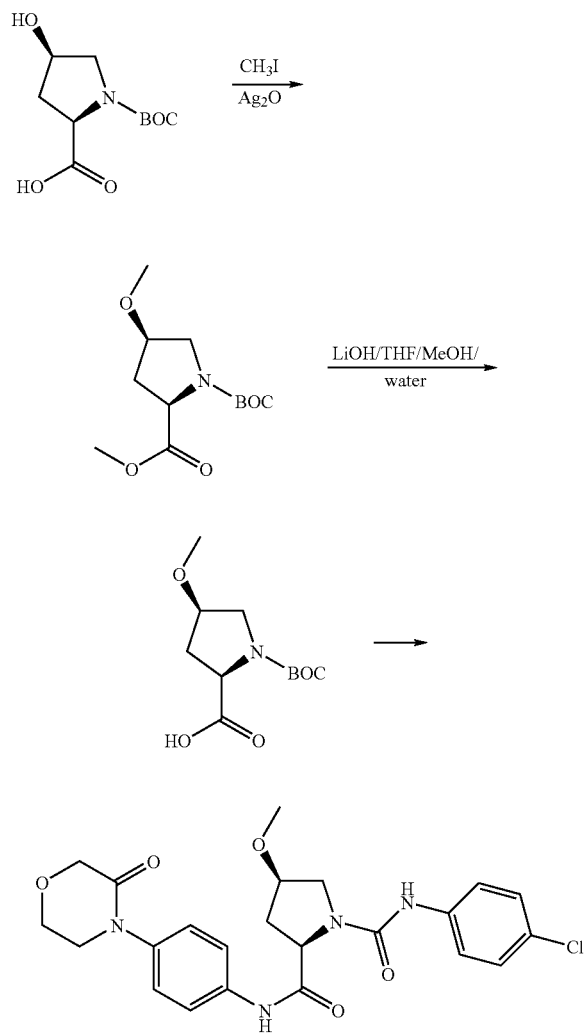

10.1 0.94 ml (15.1 mmol) of methyl iodide is added under nitrogen to a mixture of 1 g (4.32 mmol) of cis-N'-BOC-4-hydroxy-D-proline and 3.31 g (14.27 mmol) of silver oxide in 15 ml of acetone, and the reaction mixture is stirred at room temperature for 48 hours. The precipitate is subsequently filtered off, and the filtrate is evaporated to dryness under reduced pressure, giving 1 g (89.2%) of cis-N'-BOC-4-methoxy-D-proline methyl ester as a colourless oil, which is reacted further without further purification, ESI 260.

10.2 25 ml of methanol, 25 ml of water and 0.28 g (11.57 mmol) of lithium hydroxide are added to a solution of 1 g (3.85 mmol) of cis-N'-BOC-4-methoxy-D-proline methyl ester in 75 ml of tetrahydrofuran (THF), and the reaction solution is stirred at room temperature for 5 hours. The methanol and the THF are subsequently stripped off in a rotary evaporator, and the aqueous solution is extracted once by shaking with 10 ml of methylene chloride and acidified to pH 2 by means of saturated citric acid solution, and the acidic solution is extracted twice with 10 ml of methylene chloride each time. Drying of the combined organic phases over sodium sulfate and stripping-off of the solvent gives 0.5 g (53%) of cis-N'-BOC-4-methoxy-D-proline as a pale oil, which gradually crystallises, ESI 246.

10.3 Analogously to Example 7, reaction of cis-N'-BOC-4-methoxy-D-proline gives the compound 1-N-[(4-chlorophenyl)]-2-N-{[4-(3-oxomorpholin-4-yl)phenyl]}-(2R,4R)-4-methoxypyrrolidine-1,2-dicarboxamide ("A11") as a white powder, ESI 473, m.p. 133°.

The following compounds are obtained analogously

1-N-[(4-chlorophenyl)]-2-N-{[2-fluoro-4-(3-oxomorpholin-4-yl)-phenyl]}-(2R,4R)-4-allyloxypyrrolidine-1,2-dicarboxamide, ESI 517, m.p. 106°

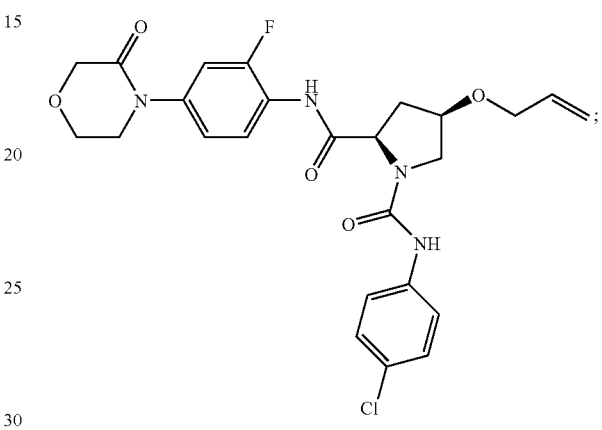

1-N-[(4-chlorophenyl)]-2-N-{[4-(3-oxomorpholin-4-yl)phenyl]}-(2R,4R)-4-ethoxypyrrolidine-1,2-dicarboxamide, ESI 487, m.p. 136°;

1-N-[(4-chlorophenyl)]-2-N-{[4-(3-oxomorpholin-4-yl)phenyl]}-(2R,4R)-4-propoxypyrrolidine-1,2-dicarboxamide, ESI 501, m.p. 106;

1-N-[(4-chlorophenyl)]-2-N-{[4-(3-oxomorpholin-4-yl)phenyl]}-(2R,4R)-4-allyloxypyrrolidine-1,2-dicarboxamide, ESI 499, m.p. 100° and as by-product 2-N-{allyl-[4-(3-oxomorpholin-4-yl)phenyl]}-1-N-[(4-chlorophenyl)]-4-hydroxypyrrolidine-1,2-dicarboxamide, ESI 499;

1-N-[(4-chlorophenyl)]-2-N-{[3-methyl-4-(3-oxomorpholin-4-yl)-phenyl]{-(2R,4R)-4-methoxypyrrolidine-1,2-dicarboxamide, ESI 487, m.p. 140°;

1-N-[(4-chlorophenyl)]-2-N-{[4-(2-oxo-2H-pyridin-1-yl)phenyl]}-(2R,4R)-4-methoxypyrrolidine-1,2-dicarboxamide, ESI 467, m.p. 133°;

1-N-[(4-chlorophenyl)]-2-N-{[2-fluoro-4-(3-oxomorpholin-4-yl)-phenyl]}-(2R,4R)-4-methoxypyrrolidine-1,2-dicarboxamide, ESI 491, m.p. 109°;

1-N-[(4-chlorophenyl)]-2-N-{[4-(2-oxo-2H-pyrazin-1-yl)phenyl]}-(2R,4R)-4-methoxypyrrolidine-1,2-dicarboxamide, ESI 468, m.p. 127°;

1-N-[(4-chlorophenyl)]-2-N-{[3-fluoro-4-(3-oxomorpholin-4-yl)-phenyl]}-(2R,4R)-4-methoxypyrrolidine-1,2-dicarboxamide, ESI 491, m.p. 99°;

1-N-[(4-chlorophenyl)]-2-N-{[2-fluoro-4-(2-oxo-2H-pyridin-1-yl)-phenyl]}-(2R,4R)-4-methoxypyrrolidine-1,2-dicarboxamide, ESI 485;

1-N-[(4-chlorophenyl)]-2-N-{[4-(2-oxo-2H-pyrazin-1-yl)phenyl]}-(2R,4R)-4-ethoxypyrrolidine-1,2-dicarboxamide, ESI 482, m.p. 132°;

1-N-[(4-chlorophenyl)]-2-N-{[3-fluoro-4-(3-oxomorpholin-4-yl)-phenyl]}-(2R,4R)-4-ethoxypyrrolidine-1,2-dicarboxamide, ESI 505, m.p. 131°;

1-N-[(4-chlorophenyl)]-2-N-{[4-(3-oxomorpholin-4-yl)
phenyl]}-(2R,4R)-4-(prop-2-ynyloxy)pyrrolidine-1,2-dicarboxamide, ESI 497, m.p. 120°;
1-N-[(4-chlorophenyl)]-2-N-{[4-(3-oxomorpholin-4-yl)
phenyl]}-(2R,4R)-4-(but-2-ynyloxy)pyrrolidine-1,2-dicarboxamide,
1-N-[(4-chlorophenyl)]-2-N-{[2-fluoro-4-(3-oxomorpholin-4-yl)-phenyl]}-(2R,4R)-4-(prop-2-ynyloxy)pyrrolidine-1,2-dicarboxamide, ESI 515, m.p. 108°;
1-N-[(4-chlorophenyl)]-2-N-{[2-fluoro-4-(3-oxomorpholin-4-yl)-phenyl]}-(2R,4S)-4-(prop-2-ynyloxy)pyrrolidine-1,2-dicarboxamide, ESI 515, m.p. 92°;
1-N-[(4-chlorophenyl)]-2-N-{[4-(3-oxomorpholin-4-yl)
phenyl]}-(2R,4R)-4-(methoxycarbonylmethoxy)pyrrolidine-1,2-dicarboxamide, ESI 531, m.p. 106°; and therefrom by hydrolysis
1-N-[(4-chlorophenyl)]-2-N-{[4-(3-oxomorpholin-4-yl)
phenyl]}-(2R,4R)-4-(carboxymethoxy)pyrrolidine-1,2-dicarboxamide, ESI 517, m.p. 134°;
1-N-[(4-bromophenyl)]-2-N-{[2-fluoro-4-(3-oxomorpholin-4-yl)-phenyl]}-(2R,4R)-4-methoxypyrrolidine-1,2-dicarboxamide, ESI 536, m.p. 103°.

EXAMPLE 11

(3R,5R)-1-(4-chlorophenylcarbamoyl)-5-[4-(3-oxomorpholin-4-yl)phenyl-carbamoyl]pyrrolidin-3-yl isobutyrate ("A12") is prepared analogously to the following scheme:

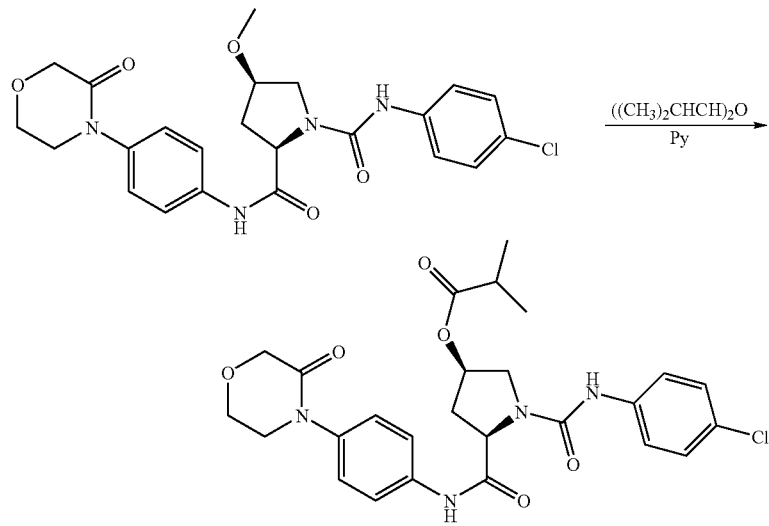

A solution of 0.2 g (0.44 mmol) of "A8" and 0.146 ml of isobutyric anhydride in 1 ml of pyridine is stirred at room temperature for 12 hours. 10 ml of ethyl acetate are subsequently added to the reaction mixture, and the ethyl acetate solution is washed successively with 5 ml of 1N hydrochloric acid and 5 ml of saturated sodium chloride solution and dried over sodium sulfate. Removal of the drying agent by filtration and stripping-off of the solvent gives 183 mg (79.3%) of (3R,5R)-1-(4-chloro-phenylcarbamoyl)-5-[4-(3-oxomorpholin-4-yl)phenylcarbamoyl]pyrrolidin-3-yl isobutyrate ("12") as white crystals, ESI 529, m.p. 129°.

The following compounds are obtained analogously
(3R,5R)-1-(4-chlorophenylcarbamoyl)-5-[4-(3-oxomorpholin-4-yl)phenylcarbamoyl]pyrrolidin-3-yl propionate, ESI 515;
(3R,5R)-1-(4-chlorophenylcarbamoyl)-5-[4-(3-oxomorpholin-4-yl)phenylcarbamoyl]pyrrolidin-3-yl acetate, ESI 501, m.p. 148°.

EXAMPLE 12

4-N-[(4-chlorophenyl)]-5-N-{[4-(3-oxomorpholin-4-yl)phenyl]}-1,3-dioxolane-4,5-dicarboxamide is prepared analogously to the following scheme:

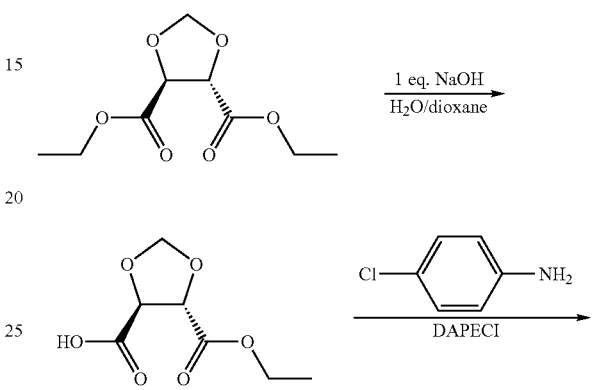

-continued

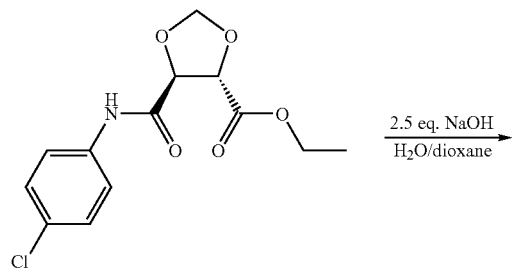

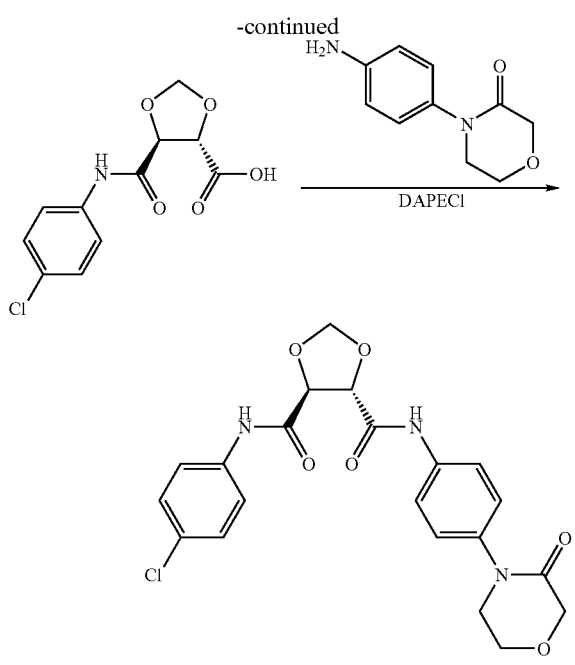

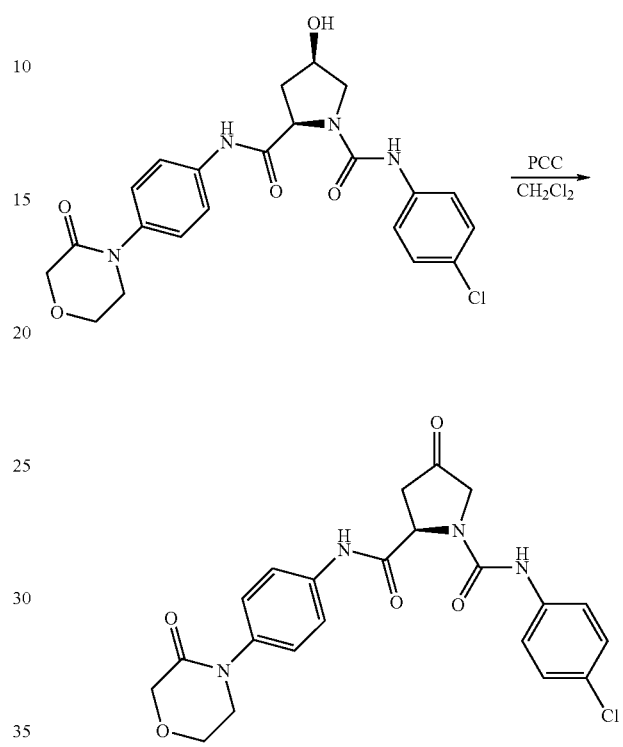

The following compounds are obtained analogously
4-N-[(4-chlorophenyl)]-5-N-{[3-methyl-4-(3-oxomorpholin-4-yl)-phenyl]}-1,3-dioxolane-4,5-dicarboxamide,
4-N-[(4-chlorophenyl)]-5-N-{[4-(2-oxo-2H-pyridin-1-yl)phenyl]}-1,3-dioxolane-4,5-dicarboxamide, ESI 440;
4-N-[(4-chlorophenyl)]-5-N-{[4-(3-oxomorpholin-4-yl)phenyl]}-1,3-dioxolane-2,2-dimethyl-4,5-dicarboxamide, ESI 474;
4-N-[(4-chlorophenyl)]-5-N-{[3-methyl-4-(3-oxomorpholin-4-yl)-phenyl]}-1,3-dioxolane-2,2-dimethyl-4,5-dicarboxamide, ESI 488;
4-N-[(4-chlorophenyl)]-5-N-{[4-(2-oxo-1H-pyridin-1-yl)phenyl]}-1,3-dioxolane-2,2-dimethyl-4,5-dicarboxamide, ESI 468.

EXAMPLE 13

Analogously to Example 7, reaction of N-[4-(3-oxomorpholin-4-yl)phenyl]-1-BOC-piperazine-2-carboxamide with 4-chlorophenyl isocyanate gives the compound
1-N-[4-chlorophenyl)]-2-N-{[4-(3-oxomorpholin-4-yl)phenyl]}-1-BOC-piperazine-1,2-dicarboxamide

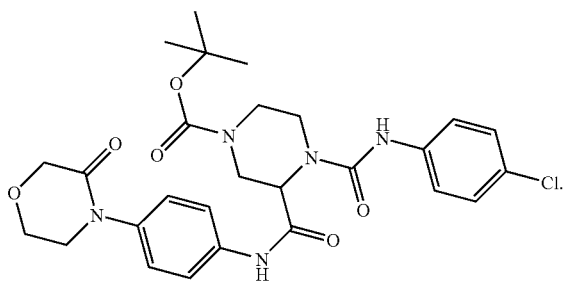

Removal of the BOC group gives 1-N-[4-chlorophenyl)]-2-N-{[4-(3-oxomorpholin-4-yl)phenyl]}-piperazine-1,2-dicarboxamide.
Analogous reaction of 4-chlorophenyl isocyanate with N-[4-(3-oxomorpholin-4-yl)phenyl]-1,3-oxazinane-4-carboxamide gives the compound
1-N-[4-chlorophenyl]-2-N-{[4-(3-oxomorpholin-4-yl)phenyl]}-1,3-oxazinane-3,4-dicarboxamide.

EXAMPLE 13-1

1-N-[(4-chlorophenyl)]-2-N-{[4-(3-oxomorpholin-4-yl)phenyl]}-(R)-4-oxo-pyrrolidine-1,2-dicarboxamide is prepared analogously to the following scheme:

0.21 g (0.98 mmol) of pyridinium chlorochromate (PCC) is added to the solution of 0.3 g (0.65 mmol) of 1-N-[(4-chlorophenyl)]-2-N-{[4-(3-oxomorpholin-4-yl)phenyl]}-(1R,4R)-4-hydroxypyrrolidine-1,2-dicarboxamide (Example 7) in 15 ml of methylene chloride, and the reaction mixture is stirred at room temperature for 48 hours. The precipitate is subsequently filtered off, and the filtrate is washed three times with 20 ml of water each time and dried over sodium sulfate. After the solvent has been stripped off, the residue is purified by preparative HPLC, giving 140 mg (47%) of 1-N-[(4-chlorophenyl)]-2-N-{[4-(3-oxomorpholin-4-yl)phenyl]}-(R)-4-oxo-pyrrolidine-1,2-dicarboxamide as a white powder, ESI 457, m.p. 154°.

EXAMPLE 13-2

N-[4-(3-oxomorpholin-4-yl)phenyl]-(2R,4R)-1-[2-(4-chlorophenyl)acetyl]-4-hydroxypyrrolidine-2-carboxamide is prepared analogously to the following scheme:

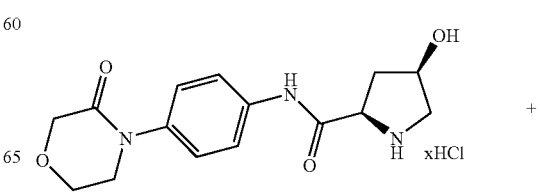

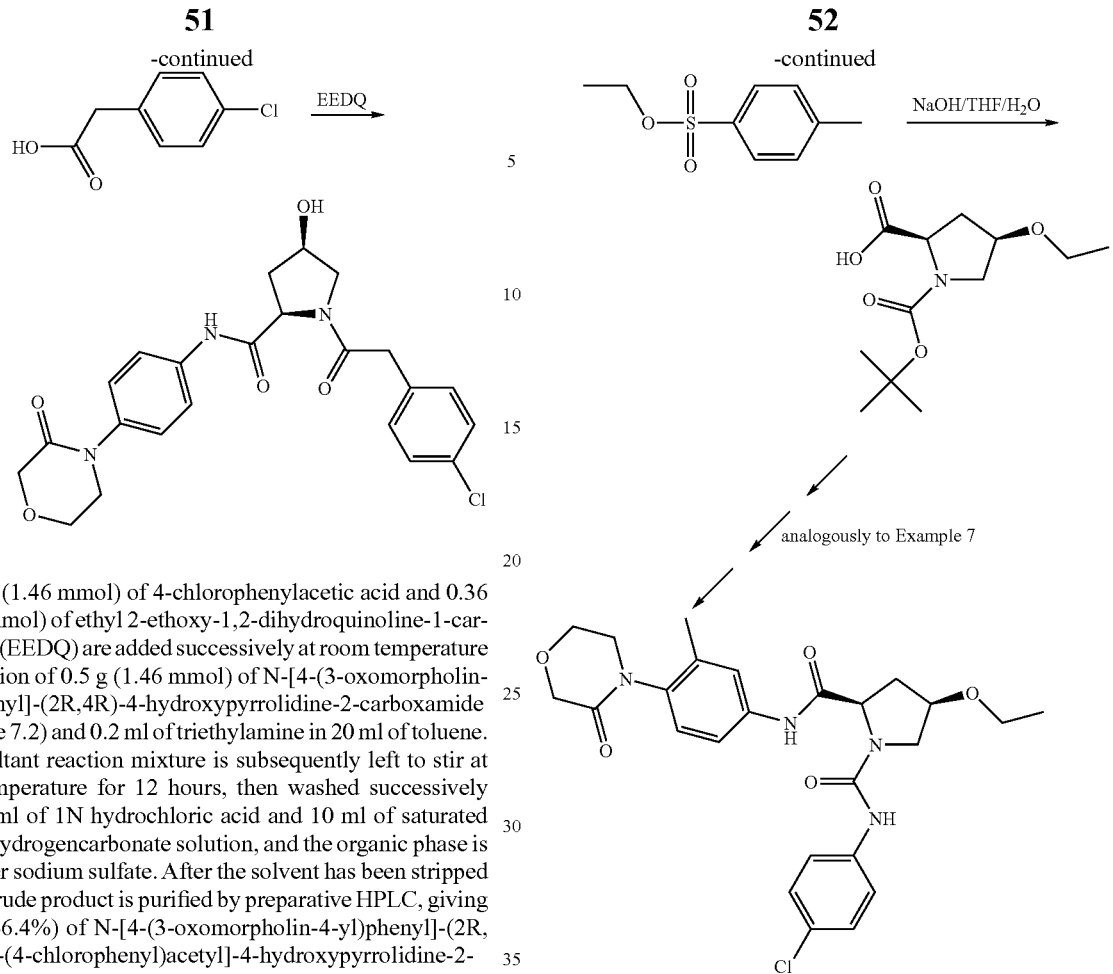

0.25 g (1.46 mmol) of 4-chlorophenylacetic acid and 0.36 g (1.46 mmol) of ethyl 2-ethoxy-1,2-dihydroquinoline-1-carboxylate (EEDQ) are added successively at room temperature to a solution of 0.5 g (1.46 mmol) of N-[4-(3-oxomorpholin-4-yl)phenyl]-(2R,4R)-4-hydroxypyrrolidine-2-carboxamide (Example 7.2) and 0.2 ml of triethylamine in 20 ml of toluene. The resultant reaction mixture is subsequently left to stir at room temperature for 12 hours, then washed successively with 10 ml of 1N hydrochloric acid and 10 ml of saturated sodium hydrogencarbonate solution, and the organic phase is dried over sodium sulfate. After the solvent has been stripped off, the crude product is purified by preparative HPLC, giving 0.31 g (46.4%) of N-[4-(3-oxomorpholin-4-yl)phenyl]-(2R,4R)-1-[2-(4-chlorophenyl)acetyl]-4-hydroxypyrrolidine-2-carboxamide as a white powder, ESI 458, m.p. 141°.

The following compounds are obtained analogously

N-[4-(3-oxomorpholin-4-yl)phenyl]-(2R,4R)-1-(4-chlorobenzoyl)-4-hydroxypyrrolidine-2-carboxamide, ESI 444, m.p. 216°;

N-[4-(3-oxomorpholin-4-yl)phenyl]-(2R,4R)-1-(1-1H-indol-3-yl-methanoyl)-4-hydroxypyrrolidine-2-carboxamide, ESI 449, m.p. 283°;

N-[4-(3-oxomorpholin-4-yl)phenyl]-(2R,4R)-1-(1-1H-indol-6-yl-methanoyl)-4-hydroxypyrrolidine-2-carboxamide, ESI 449, m.p. 148°.

EXAMPLE 13-3

1-N-[(4-chlorophenyl)]-2-N-{[3-methyl-4-(3-oxomorpholin-4-yl)phenyl]}-(2R,4R)-4-ethoxypyrrolidine-1,2-dicarboxamide is prepared analogously to the following scheme:

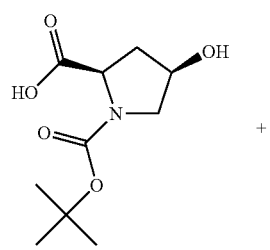

A suspension of 5 g (21.62 mmol) of cis-N'-Boc-4-hydroxy-D-proline and 8.66 g (43.24 mmol) of ethyl 4-toluenesulfonate in 5 ml of tetrahydrofuran (THF) is added with a solution of 2.94 g (73.5 mmol) of sodium hydroxide in 5 ml of, water. The reaction mixture is then stirred at 40° C. for 12 hours and subsequently evaporated in a rotary evaporator, and the residue is taken up in 10 ml of water. The aqueous solution is then washed twice with 10 ml of methylene chloride each time and acidified using 2N hydrochloric acid. The resultant acidic solution is extracted three times with 20 ml of methylene chloride each time. Drying of the combined methylene chloride extracts over sodium sulfate and stripping-off of the solvent gives 4.87 g (86.9%) of cis-N'-Boc-4-ethoxy-D-proline as a colourless oil. ESI: 232. Analogously to Example 7, reaction of cis-N'-Boc-4-ethoxy-D-proline gives the compound 1-N-[(4-chlorophenyl)]-2-N-{[3-methyl-4-(3-oxomorpholin-4-yl)phenyl]}-(2R,4R)-4-ethoxypyrrolidine-1,2-dicarboxamide, ESI 501, m.p. 117°.

The compounds

1-N-[(4-chlorophenyl)]-2-N-{[4-(2-oxo-1H-pyridin-1-yl) phenyl]}-(2R,4R)-4-ethoxypyrrolidine-1,2-dicarboxamide, ESI 481, m.p. 209°;

1-N-[(4-chlorophenyl)]-2-N-{[2-fluoro-4-(3-oxomorpholin-4-yl)phenyl]}-(2R,4R)-4-ethoxypyrrolidine-1,2-dicarboxamide, ESI 505, m.p. 187°;

are obtained analogously.

EXAMPLE 13-4

2-N-[(4-chlorophenyl)]-1-N-{[4-(3-oxomorpholin-4-yl)phenyl]}-(R)-pyrrolidine-1,2-dicarboxamide is prepared analogously to the following scheme:

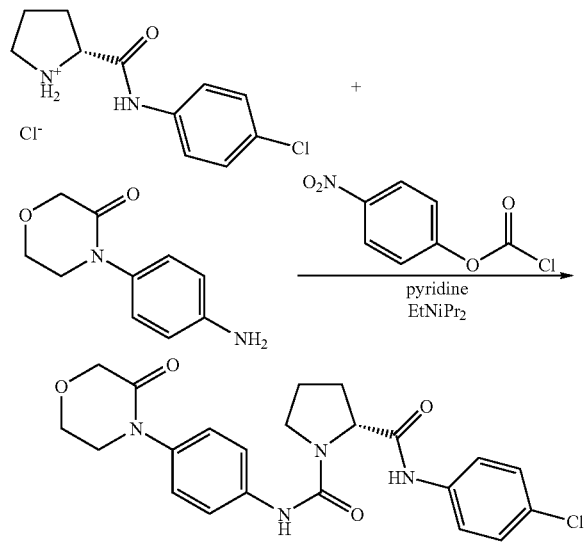

1.01 g (5.00 mmol) of 4-nitrophenyl chloroformate and 0.404 ml (5.00 mmol) of pyridine are added to a solution of 961 mg (5.00 mmol) of 4-(4-aminophenyl)morpholin-3-one in 10 ml of dichloromethane, and the mixture is stirred at room temperature for 1 hour. 1.31 g (5.00 mmol) of (R)-2-(4-chlorophenylcarbamoyl)pyrrolidinium chloride and 2.55 ml (15.0 mmol) of N-ethyldiisopropylamine are added to the suspension. The reaction mixture is stirred at room temperature for 12 hours and then evaporated, and the residue is chromatographed on a silica-gel column, giving 2-N-[(4-chlorophenyl)]-1-N-{[4-(3-oxomorpholin-4-yl)phenyl]}-(R)-pyrrolidine-1,2-dicarboxamide as a yellowish solid, ESI 443.

2-N-[(4-chlorophenyl)]-1-N-{[4-(3-oxomorpholin-4-yl)phenyl]}-(S)-pyrrolidine-1,2-dicarboxamide, ESI 443, is obtained analogously.

EXAMPLE 13-5

N-(4-chlorophenyl)-(R)-1-{2-[4-(3-oxomorpholin-4-yl)phenyl]acetyl}pyrrolidine-2-carboxamide is prepared analogously to the following scheme:

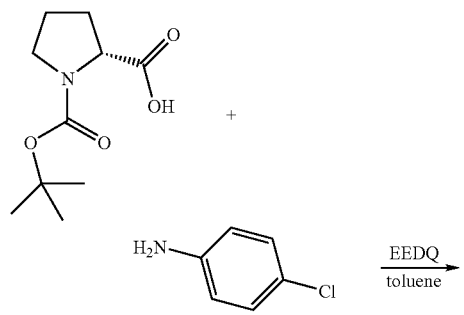

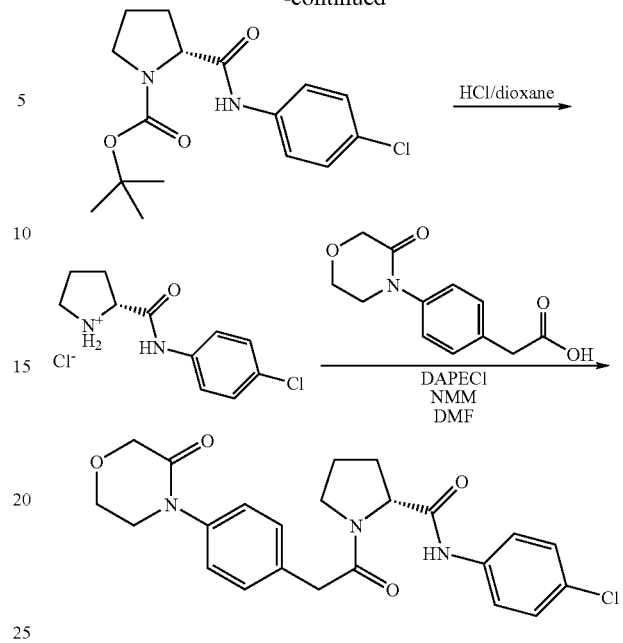

4.82 g (19.5 mmol) of ethyl 2-ethoxy-1,2-dihydroquinoline-1-carboxylate (EEDQ) are added to a suspension of 2.80 g (13.0 mmol) of N-Boc-D-proline and 1.66 g (13.0 mmol) of 4-chloroaniline in 50 ml of toluene, and the mixture is stirred at room temperature for 3 hours. The reaction mixture is filtered, and petroleum ether is added to the filtrate. The precipitate formed is filtered off and dried, giving tert-butyl (R)-2-(4-chlorophenyl-carbamoyl)pyrrolidine-1-carboxylate as colourless crystals; ESI 325.

4.00 g (12.3 mmol) of tert-butyl (R)-2-(4-chlorophenylcarbamoyl)pyrrolidine-1-carboxylate are dissolved in 20 ml of 4N HCl in dioxane and left at room temperature for 2 hours. The reaction mixture is evaporated and dried, giving (R)-2-(4-chlorophenylcarbamoyl)pyrrolidinium chloride as a slightly brownish solid; ESI 225.

0.26 ml (2.4 mmol) of 4-methylmorpholine and 230 mg (1.2 mmol) of N-(3-dimethylaminopropyl)-N'-ethylcarbodiimide hydrochloride (DAPECI) are added to a solution of 261 mg (1.00 mmol) of (R)-2-(4-chlorophenyl-carbamoyl)pyrrolidinium chloride and 235 mg (1.00 mmol) of 4-(3-oxomorpholin-4-yl)phenylacetic acid in 2 ml of DMF, and the mixture is stirred at room temperature for 18 hours. The reaction mixture is introduced into water, and the precipitate formed is filtered off, giving N-(4-chlorophenyl)-(R)-1-{2-[4-(3-oxomorpholin-4-yl)phenyl]acetyl}pyrrolidine-2-carboxamide as a slightly brownish solid; ESI 442.

N-(4-chlorophenyl)-(S)-1-{2-[4-(3-oxomorpholin-4-yl)phenyl]acetyl}pyrrolidine-2-carboxamide, ESI 442, is obtained analogously.

Preparation of the Carboxylic Acid Unit

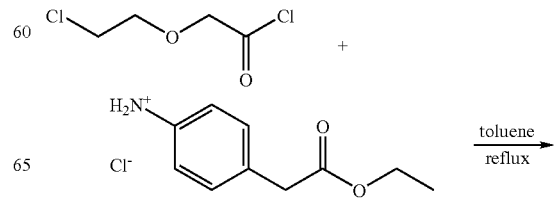

-continued

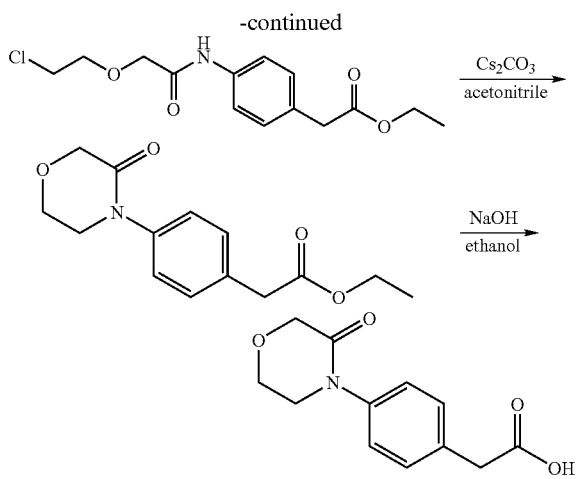

14.6 g (92.7 mmol) of (2-chloroethoxy)acetyl chloride are added to a suspension of 20.0 g (92.7 mmol) of ethyl 4-aminophenylacetate hydrochloride in 25 ml of toluene, and the mixture is heated at the boil for 24 hours. The reaction mixture is evaporated and dried, giving ethyl {4-[2-(2-chloroethoxy)acetylamino]phenyl}acetate as a yellowish solid; ESI 300.

43.4 g (133 mmol) of caesium carbonate are added to a solution of 26.6 g (88.8 mmol) of ethyl {4-[2-(2-chloroethoxy)acetylamino]phenyl}acetate in 100 ml of acetonitrile, and the mixture is stirred at room temperature for 18 hours. The reaction mixture is tittered, and the filtrate is evaporated, giving ethyl [4-(3-oxomorpholin-4-yl)phenyl]acetate as a yellowish oil; ESI 264.

20.2 g (76.8 mmol) of ethyl [4-(3-oxomorpholin-4-yl)phenyl]acetate are dissolved in a solution of 3.37 g of sodium hydroxide in 40 ml of ethanol, and the reaction solution is stirred at room temperature for 18 hours. The reaction mixture is evaporated, and the residue is dissolved in water and acidified to a pH of 3 using 1N hydrochloric acid. The mixture is extracted with ethyl acetate, and the organic phase is dried over sodium sulfate and evaporated, giving 4-(3-oxomorpholin-4-yl)phenylacetic acid as a yellowish solid; ESI 236.

The following compounds are obtained analogously to Example 13-5:

N-(4-chlorophenyl)-(2R,4R)-1-{2-[4-(3-oxomorpholin-4-yl)phenyl]-acetyl}-4-methoxypyrrolidine-2-carboxamide, N-(4-chlorophenyl)-(2R,4S)-1-{2-[4-(3-oxomorpholin-4-yl)phenyl]-acetyl}-4-methoxypyrrolidine-2-carboxamide, N-(4-chlorophenyl)-(2S,4R)-1-{2-[4-(3-oxomorpholin-4-yl)phenyl]-acetyl}-4-methoxypyrrolidine-2-carboxamide, N-(4-chlorophenyl)-(S)-1-{2-[4-(2-oxo-1H-pyridin-1-yl)phenyl]acetyl}-pyrrolidine-2-carboxamide, N-(4-chlorophenyl)-(S)-1-{2-[4-(2-oxopyrrolidin-1-yl)phenyl]acetyl}-pyrrolidine-2-carboxamide, N-(4-chlorophenyl)-(R)-1-{2-[4-(2-oxopyrrolidin-1-yl)phenyl]acetyl}-pyrrolidine-2-carboxamide, N-(4-chlorophenyl)-(R)-1-[4-(2-oxopiperidin-1-yl)benzoyl]pyrrolidine-2-carboxamide, N-(4-chlorophenyl)-(R)-1-[4-(2-oxopiperidin-1-yl)phenyloxycarbonyl]-pyrrolidine-2-carboxamide.

EXAMPLE 13-6

1-N-[(4-chlorophenyl)]-2-N-([4-(3-oxomorpholin-4-yl)phenyl]}-(2R,4R)-4-(2,3-dihydroxypropoxy)pyrrolidine-1,2-dicarboxamide is prepared analogously to the following scheme:

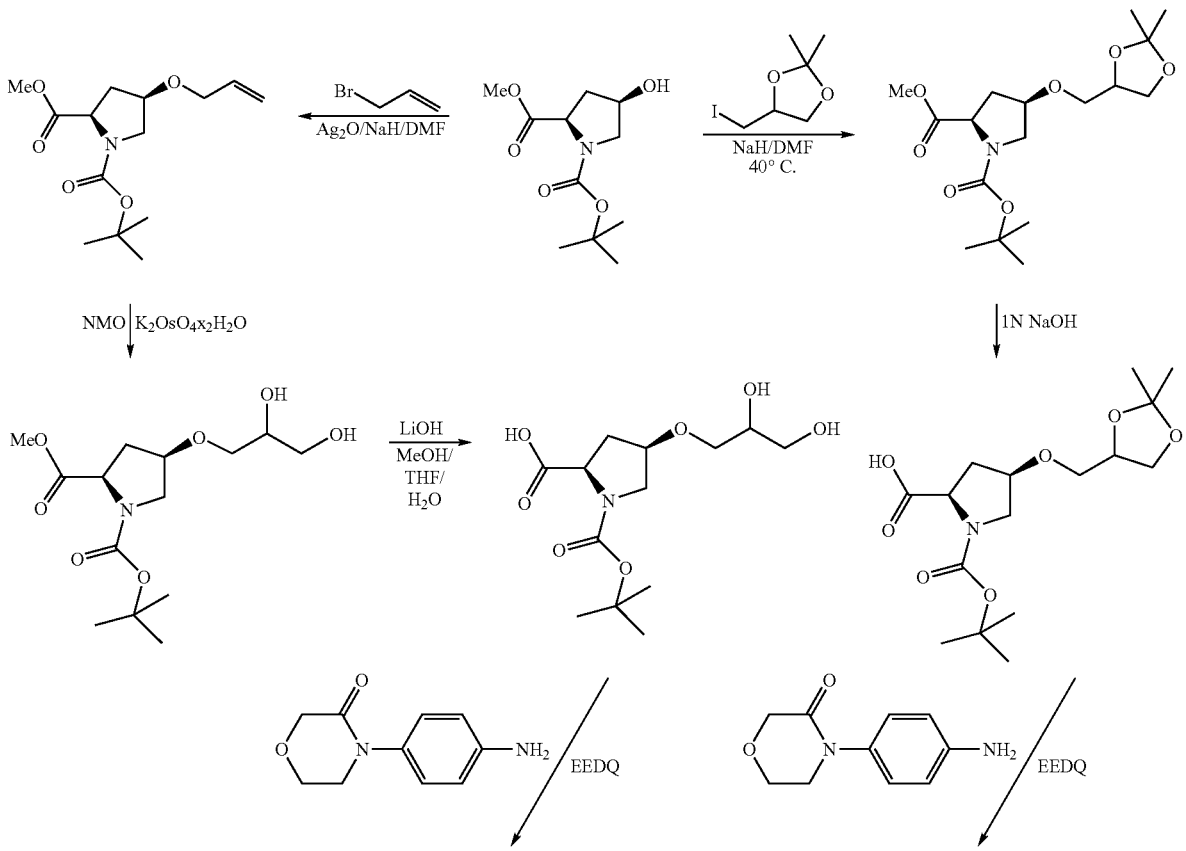

-continued

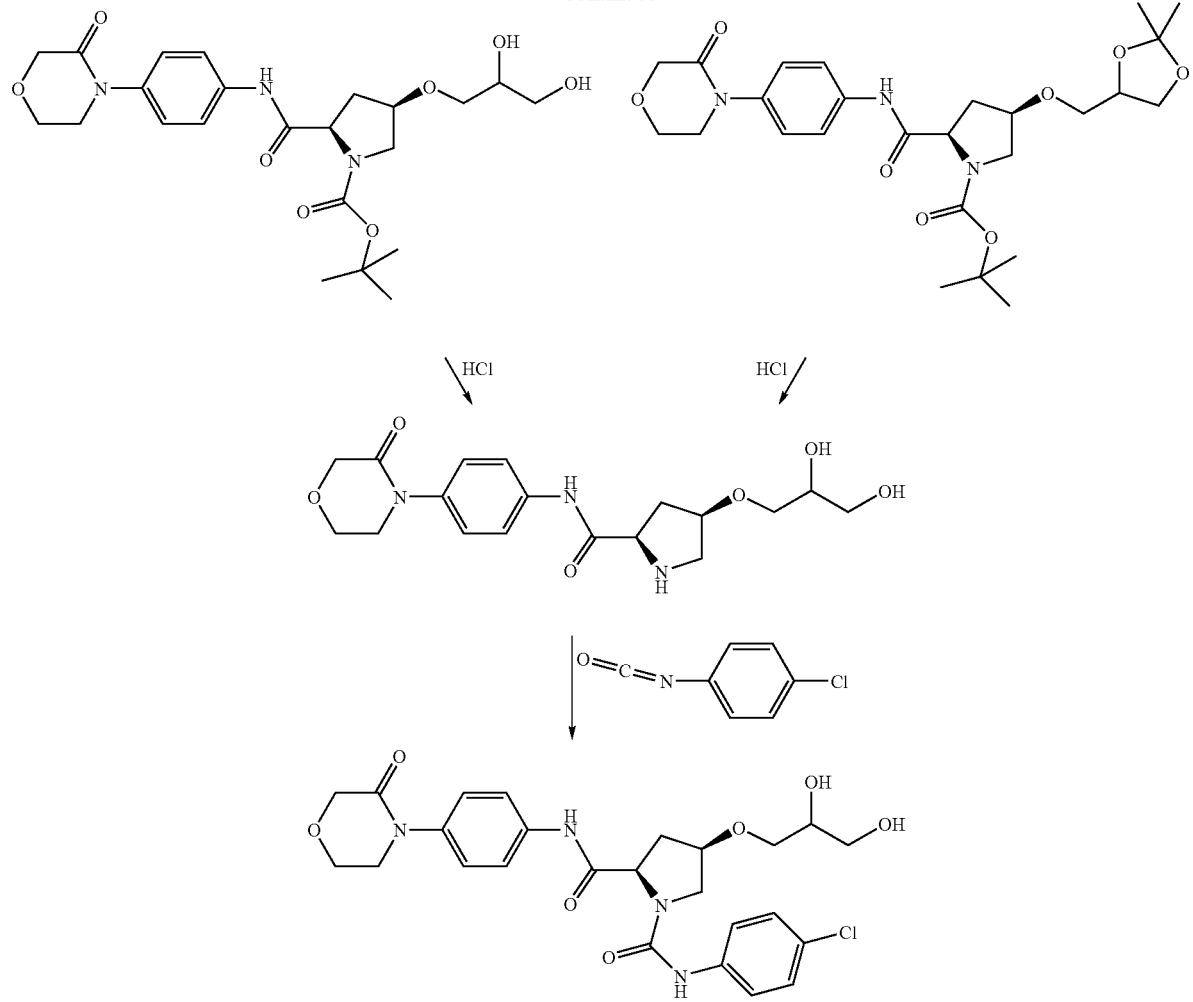

NMO: N-Methyl-morpholin-N-oxid 1.55 g (38.6 mmol) of sodium hydride are added in portions under nitrogen to the solution of 10.3 g (42 mmol) of 1-tert-butyl 2-methyl (2R,4R)-4-hydroxypyrrolidine-1,2-dicarboxylate and 36.34 ml (420 mmol) of 3-bromo-1-propene in 100 ml of dimethylformamide (DMF), and the mixture is subsequently stirred at room temperature for 15 minutes. 9.73 g (42 mmol) of silver oxide are then added in portions to the reaction mixture, and the reaction mixture is left to stir at room temperature for a further 12 hours: The reaction mixture is then filtered, the filtrate is evaporated to dryness under reduced pressure, and the residue is taken up in 20 ml of saturated citric acid solution. After the precipitate has been filtered off, the filtrate is extracted twice with 20 ml of ethyl acetate each time. Drying of the combined organic phases over sodium sulfate and stripping-off of the solvent gives 11.6 g of 1-tert-butyl 2-methyl (2R,4R)-4-allyloxypyrrolidine-1,2-dicarboxylate as a red-brown oil; ESI 286.

6.16 g (52.6 mmol) of N-methylmorpholine N-oxide (NMO) and 193.7 mg of potassium osmate dihydrate are added successively at room temperature to the solution of 5 g (17.52 mmol) of 1-tert-butyl 2-methyl (2R,4R)-4-allyloxy-pyrrolidine-1,2-dicarboxylate in 60 ml of water, 25 ml of acetone and 10 ml of tert-butanol, and the mixture is stirred for 48 hours. 6.6 g (52.6 mmol) of sodium sulfite are subsequently added to the reaction mixture, which is stirred at room temperature for a further hour. The reaction mixture is then evaporated under reduced pressure, the residue is taken up in 50 ml of water, and the aqueous solution is extracted twice with 20 ml of ethyl acetate each time. Drying of the combined organic phases over sodium sulfate and stripping-off of the solvent gives 4.7 g of 1-tert-butyl 2-methyl (2R,4R)-4-(2,3-dihydroxypropoxy)pyrrolidine-1,2-dicarboxylate as a yellowish oil; ESI 320. 1.06 g of lithium hydroxide are added to the solution of 4.6 g of this methyl ester in 40 ml of tetrahydrofuran, 10 ml of methanol and 10 ml of water, and the reaction mixture is stirred at room temperature for 12 hours. The reaction mixture is subsequently evaporated under reduced pressure, 10 ml of saturated citric acid solution are added to the aqueous solution which remains, and the mixture is extracted three times with 20 ml of ethyl acetate each time. Drying of the combined organic phases over sodium sulfate and stripping-off of the solvent gives 4.3 g of tert-butyl (2R,4R)-4-(2,3-dihydroxypropoxy)pyrrolidine-1,2-dicarboxylate as a yellow powder; ESI 306. Analogously to Example 7, this acid gives the compound 1-N-[(4-chlorophenyl)]-2-N-{[4-(3-oxomorpholin-4-yl)phenyl])-(2R,4R)-4-(2,3-dihydroxypropoxy)pyrrolidine-1,2-dicarboxamide; ESI 533.

1-N-[(4-chlorophenyl)]-2-N-{[2-fluoro-4-(3-oxomorpholin-4-yl)phenyl]}-(2R,4R)-4-(2,3-dihydroxypropoxy)pyrrolidine-1,2-dicarboxamide; ESI 551, is obtained analogously.

EXAMPLE 13-7

1-N-[(4-chlorophenyl)]-2-N-{[4-(3-oxomorpholin-4-yl)phenyl]}-(2R,4R)-4-(2-hydroxy-3-pyrrolidin-1-ylpropoxy)pyrrolidine-1,2-dicarboxamide, 1-N-[(4-chlorophenyl)]-2-N-{[4-(3-oxomorpholin-4-yl)phenyl]}-(2R,4R)-4-(2-oxooxazolidin-5-ylmethoxy)pyrrolidine-1,2-dicarboxamide and 1-N-[(4-chlorophenyl)]-2-N-{[4-(3-oxomorpholin-4-yl)phenyl]}-(2R,4R)-4-(3-amino-2-hydroxypropoxy)pyrrolidine-1,2-dicarboxamide, ESI 532, m.p. 115;

are prepared analogously to the following scheme:

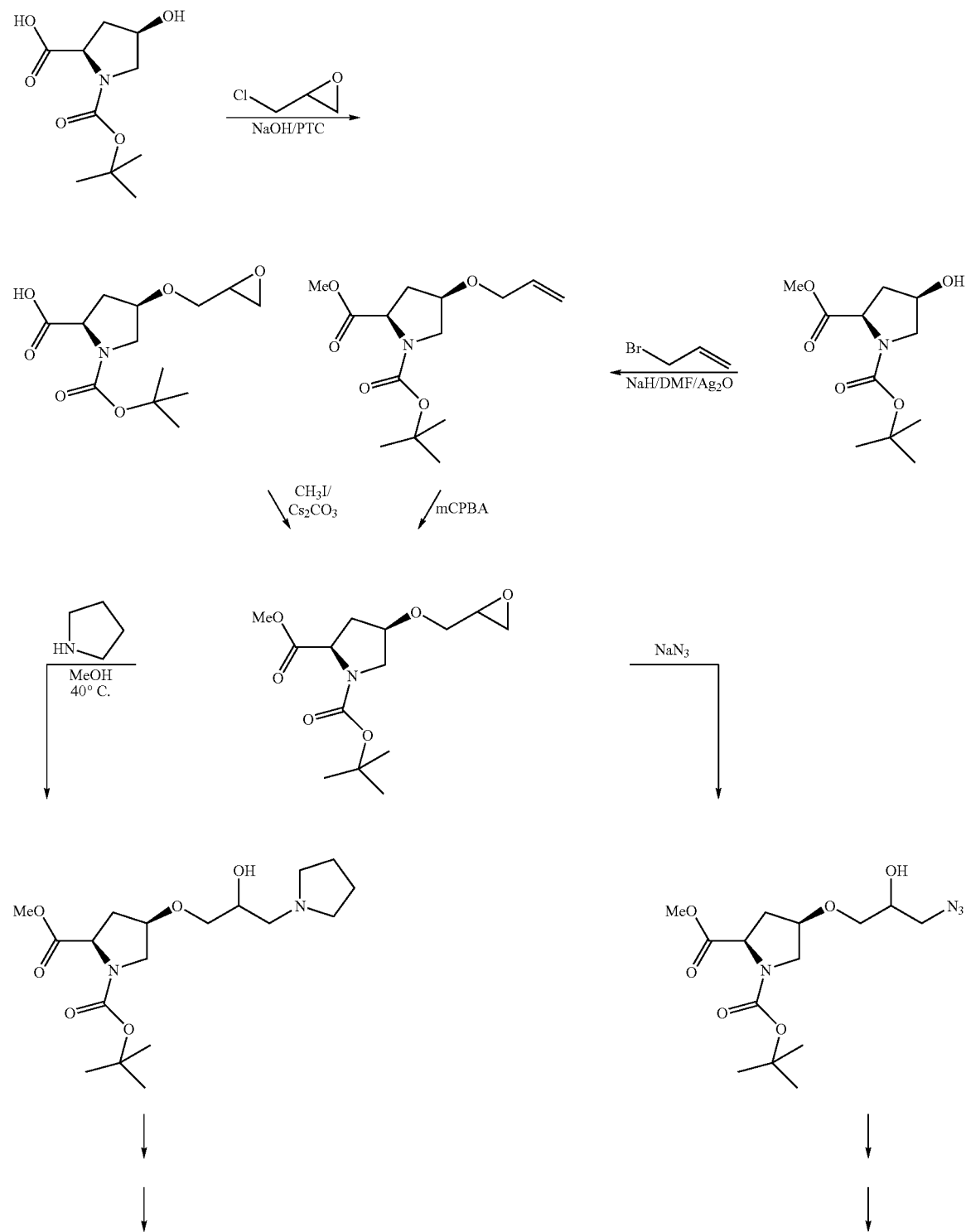

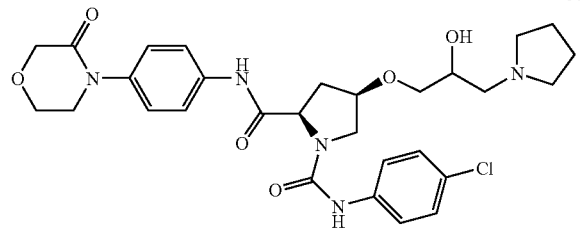
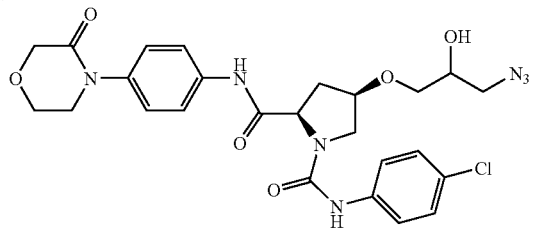

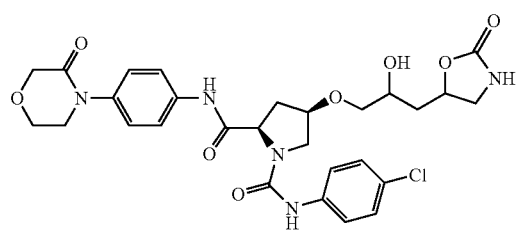
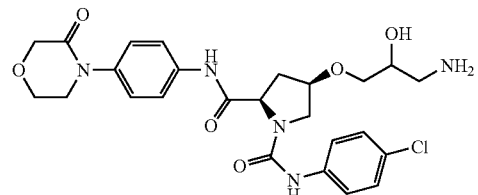

EXAMPLE 13-8

1-N-[(4-chlorophenyl)]-2-N-{N-methoxycarbonylmethyl-N'-[4-(3-oxomorpholin-4-yl)phenyl]}-(2R,4R)-4-methoxypyrrolidine-1,2-dicarboxamide is prepared analogously to the following scheme:

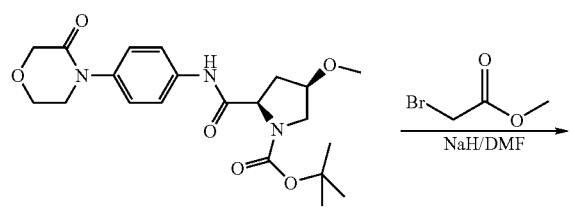

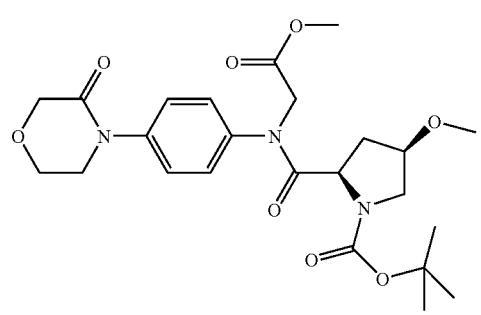

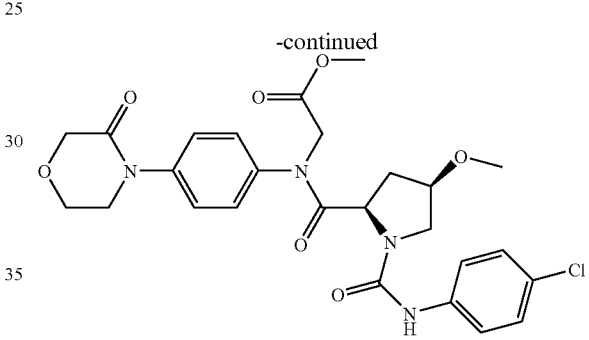

61 mg (2.54 mmol) of sodium hydride are added to the solution of 1 g (2.31 mmol) of tert-butyl (2R,4R)-4-methoxy-2-[4-(3-oxomorpholin-4-yl)-phenylcarbamoyl]pyrrolidine-1-carboxylate (prepared analogously to Example 7.1) in 20 ml of dimethylformamide, and the mixture is stirred at room temperature for 30 minutes. 022 mg (2.31 mmol) of methyl bromoacetate is subsequently added to the reaction mixture, which is then left to stir at room temperature for 12 hours. The reaction mixture is then evaporated under reduced pressure, the residue is taken up in 20 ml of water, and the aqueous solution is extracted three times with 20 ml of methylene chloride each time. Drying of the combined organic phases over sodium sulfate and stripping-off of the solvent gives 1.1 g of tert-butyl (2R,4R)-4-methoxy-2-{methoxycarbonylmethyl-[4-(3-oxomorpholin-4-yl)phenyl]-carbamoyl}pyrrolidine-1-carboxylate as a yellow oil; ESI (M-BOC) 392.

Removal of the BOC group gives 1-N-[(4-chlorophenyl)]-2-N-{N-methoxy-carbonylmethyl-N'-[4-(3-oxomorpholin-4-yl)phenyl]}-(2 R,4R)-4-methoxy-pyrrolidine-1,2-dicarboxamide, ESI 545, m.p. 106°.

The compound 1-N-[(4-chlorophenyl)]-2-N-{N-methoxycarbonylmethyl-N'-[2-fluoro-4-(3-oxomorpholin-4-yl)phenyl]}-(2 R,4R)-4-methoxypyrrolidine-1,2-dicarboxamide, ESI 563, m.p. 100°, is obtained analogously.

EXAMPLE 13-9

1-N-[(4-chlorophenyl)]-2-N-{[4-(3-oxomorpholin-4-yl)cyclohexan-1-yl]}-(2R,4R)-4-hydroxypyrrolidine-1,2-dicarboxamide is prepared analogously to the following scheme

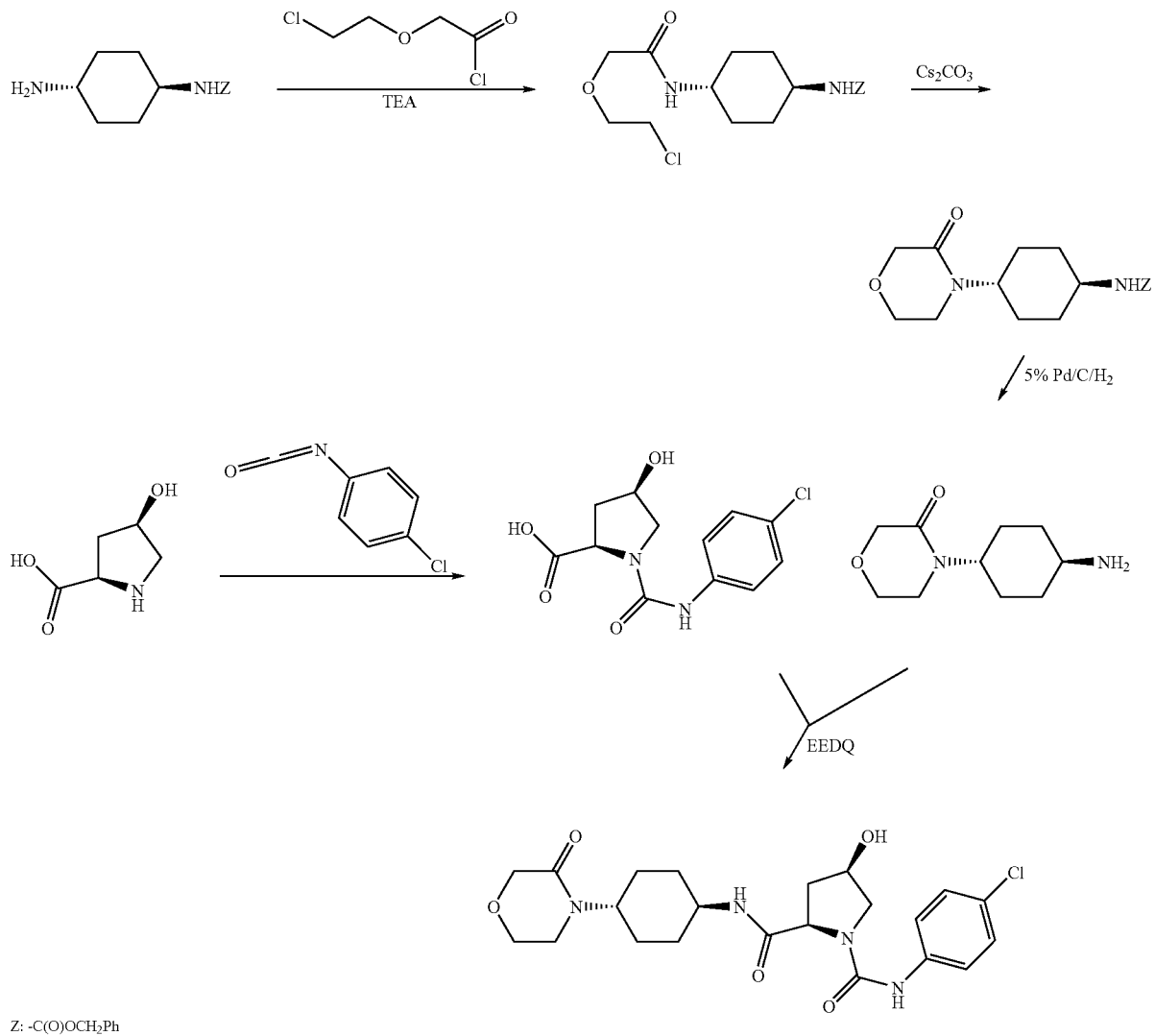

Z: -C(O)OCH$_2$Ph 13-9.1 6.32 g (40.3 mmol) of (2-chloroethoxy)acetyl chloride are added to the solution of 10 g (40.3 mmol) of benzyl (4-aminocyclohexyl)carbamate and 6.2 ml of triethylamine (TEA) in 300 ml of tetrahydrofuran, and the mixture is subsequently stirred at room temperature for 20 hours. The reaction mixture is then evaporated under reduced pressure, the residue is taken up in 20 ml of water, and the aqueous solution is extracted three times with 20 ml of ethyl acetate each time. After the combined organic phases have been dried over sodium sulfate and the solvent has been stripped off, the residue is taken up in 20 ml of acetonitrile, and 2.3 g of caesium carbonate are added to the resultant solution. The reaction mixture is then left to stir at room temperature for 48 hours and then evaporated under reduced pressure, the residue is taken up in 20 ml of water, and the aqueous solution is extracted four times with 20 ml of ethyl acetate each time. After the combined organic phases have been dried over sodium sulfate and the solvent has been stripped off, the residue is taken up in 50 ml of tetrahydrofuran, 0.3 g of 5% palladium/carbon is added to the resultant solution, and the mixture is hydrogenated until the take-up of hydrogen ceases. The catalyst is subsequently filtered off, and the filtrate is evaporated to dryness under reduced pressure, giving 1.5 g of 4-(4-aminocyclohexyl)morpholin-3-one as a colourless oil; ESI 199.

13-9.2 Analogously to Example 7.3, reaction of cis-N'-BOC-4-hydroxy-D-proline and 4-chlorophenyl isocyanate gives the compound (2R,4R)-1-(4-chlorophenylcarbamoyl)-4-hydroxypyrrolidine-2-carboxylic acid; ESI 285; m.p. 132°.

13-9.3 Analogously to Example 7.1, reaction of the amine 13-9.1 and the acid 13-9.2 gives the compound 1-N-[(4-chlorophenyl)]-2-N-{[4-(3-oxomorpholin-4-yl)cyclohexan-1-yl]}-(2R,4R)-4-hydroxypyrrolidine-1,2-dicarboxamide, ESI 465; m.p. 245°.

EXAMPLE 13-10

The following compounds are obtained analogously to Example 7

1-N-[(4-chlorophenyl)]-2-N-[(1'-methyl-[1,4']bipiperidinyl-4-yl)]-(2R,4R)-4-hydroxypyrrolidine-1,2-dicarboxamide, ESI 464; m.p. 78°

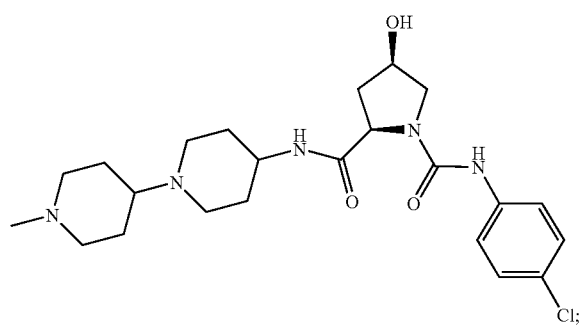

1-N-[(4-chlorophenyl)]-2-N-[(3,4,5,6-tetrahydro-2H-[1,4']bipyridinyl-4-yl)]-(2R,4R)-4-hydroxypyrrolidine-1,2-dicarboxamide, ESI 444

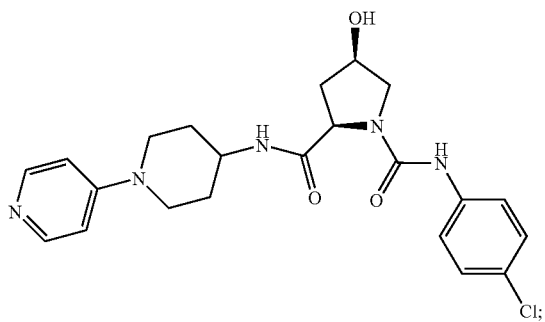

1-N-[(4-chlorophenyl)]-2-N-[(3,4,5,6-tetrahydro-2H-1,4'-bipyridinyl-4-yl)-(2R,4R)-4-ethoxypyrrolidine-1,2-dicarboxamide, ESI 472;

N-(4-chlorophenyl)-(2R,4R)-4-hydroxy-2-(4-pyridin-4-ylpiperazine-1-carbonyl)pyrrolidine-1-carboxamide, ESI 430

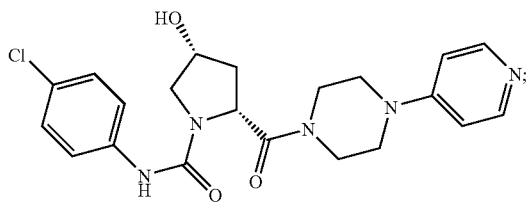

N-(4-chlorophenyl)-(2R,4R)-4-hydroxy-2-[4-(2-methoxyphenyl)-piperazine-1-carbonyl]pyrrolidine-1-carboxamide, ESI 459

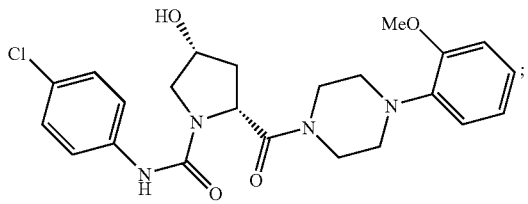

N-(4-chlorophenyl)-(2R,4R)-2-[4-(4-fluorophenyl)piperazine-1-carbonyl]-4-hydroxypyrrolidine-1-carboxamide, ESI 447;

N-(4-chlorophenyl)-(2R,4R)-4-hydroxy-2-[4-hydroxy-4-(4-methoxy-phenyl)piperidine-1-carbonyl]pyrrolidine-1-carboxamide, ESI 456;

N-(4-chlorophenyl)-(2R,4R)-4-hydroxy-2-(4-pyridin-2-ylpiperazine-1-carbonyl)pyrrolidine-1-carboxamide, ESI 430;

N-(4-chlorophenyl)-(2R,4R)-2-[4-(4-ethylpiperazin-1-yl)piperidine-1-carbonyl]-4-hydroxypyrrolidine-1-carboxamide, ESI 465;

N-(4-chlorophenyl)-(2R,4R)-2-[4-(4,6-dimethylpyrimidin-2-yl)-piperazine-1-carbonyl]-4-hydroxypyrrolidine-1-carboxamide, ESI 459;

N-(4-chlorophenyl)-(2R,4R)-4-hydroxy-2-[4-(1-methylpiperidin-4-yl)-piperazine-1-carbonyl]pyrrolidine-1-carboxamide; ESI 450;

1-N-[(4-chlorophenyl)]-2-N-{[2-(2-dimethylaminoethoxy)-4-morpholin-4-ylphenyl]}-(2R,4R)-4-hydroxypyrrolidine-1,2-dicarboxamide, ESI 532;

1-N-[(4-chlorophenyl)]-2-N-[(2-ethoxy-4-morpholin-4-ylphenyl)]-(2R,4R)-4-hydroxypyrrolidine-1,2-dicarboxamide, ESI 489;

1-N-[(4-chlorophenyl)]-2-N-[(4-morpholin-4-yl-2-propoxyphenyl)]-(2R,4R)-4-hydroxypyrrolidine-1,2-dicarboxamide, ESI 504;

EXAMPLE 13-11

The following compounds are obtained analogously to Example 7

1-N-[(4-chlorophenyl)]-2-N-{[4-(2-iminopyrrolidin-1-yl)phenyl]}-(2R,4R)-4-hydroxypyrrolidine-1,2-dicarboxamide, ESI 442;

1-N-[(4-chlorophenyl)]-2-N-{[3-methyl-4-(2-iminopyrrolidin-1-yl)-phenyl]}-(2R,4R)-4-hydroxypyrrolidine-1,2-dicarboxamide, ESI 456;

1-N-[(4-chlorophenyl)]-2-N-[4-{2-[(E)-cyanimino]imidazolidin-1-yl)-phenyl]}-(2R,4R)-4-hydroxypyrrolidine-1,2-dicarboxamide, ESI 468;

1-N-[(4-chlorophenyl)]-2-N-{[4-(2-imino-5-methylthiazol-3-yl)phenyl]}-(2R,4R)-4-hydroxypyrrolidine-1,2-dicarboxamide, ESI 473;

1-N-[(4-chlorophenyl)]-2-N-{[2-aminocarbonyl-4-(3-oxomorpholin-4-yl)phenyl]}-(2R,4R)-4-hydroxypyrrolidine-1,2-dicarboxamide, ESI 502;

1-N-[(4-chlorophenyl)]-2-N-{[4-(3-oxomorpholin-4-yl)phenyl]}-(2R,4R)-4-hydroxy-2-methylpyrrolidine-1,2-dicarboxamide, ESI 457.

EXAMPLE 13-12

N-[4-(3-oxomorpholin-4-yl)phenyl]-(2R,4R)-1-[(E)-3-(5-chlorothiophen-2-yl)-acryloyl]-4-hydroxypyrrolidine-2-carboxamide is prepared analogously to the following scheme:

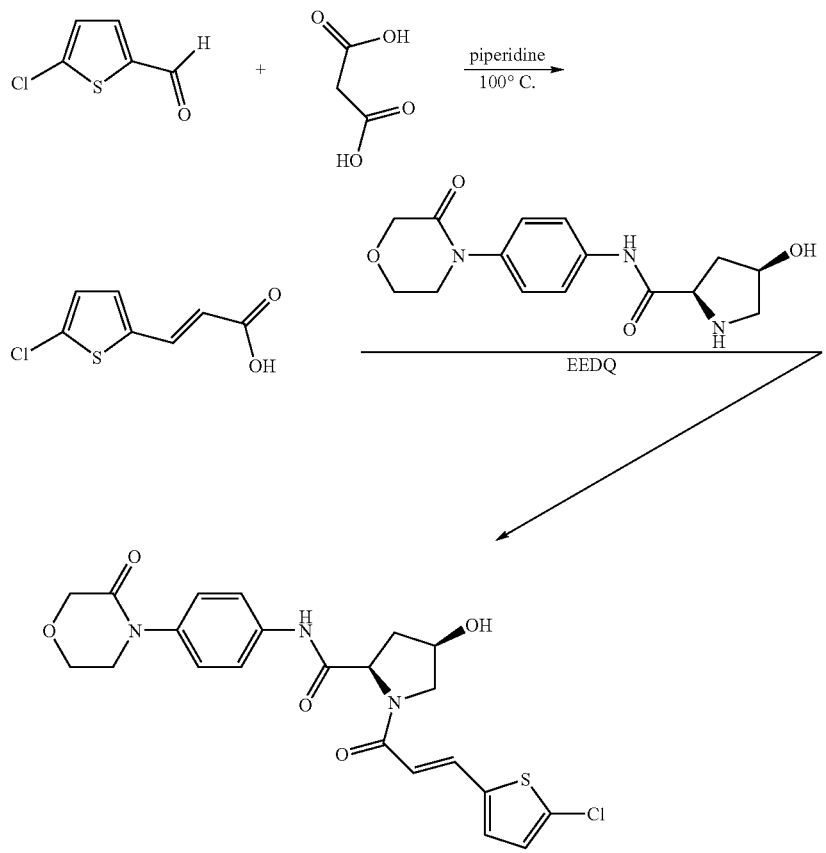

The solution of 1 g (6.62 mmol) of 5-chloro-2-thiophenecarboxaldehyde and 1.38 g (13.23 mmol) of malonic acid in 0.07 ml of piperidine and 5 ml of pyridine is refluxed for 2 hours. The reaction solution is subsequently allowed to cool, then poured into 20 ml of water and acidified to pH 1 using 2N hydrochloric acid. The product which precipitates in the process is filtered off with suction and dried in a drying cabinet at 80° C., giving 1.02 g of (E)-3-(5-chlorothiophen-2-yl)acrylic acid as brown crystals, ESI 189. Analogously to Example 7.1, reaction between the compound of Example 7.2 and (E)-3-(5-chlorothiophen-2-yl)acrylic acid gives the compound N-[4-(3-oxomorpholin-4-yl)phenyl]-(2R,4R)-1-[(E)-3-(5-chlorothiophen-2-yl)acryloyl]-4-hydroxypyrrolidine-2-carboxamide as colourless crystals, ESI 476, m.p. 151°.

The following compounds are obtained analogously
N-[4-(3-oxomorpholin-4-yl)phenyl]-(2R,4R)-1-[(E)-3-thiophen-3-ylacryloyl]-4-hydroxypyrrolidine-2-carboxamide, ESI 442, m.p. 137°;
N-[4-(3-oxomorpholin-4-yl)phenyl]-(2R,4R)-1-[(2E,4E)-5-phenylpenta-2,4-dienyloyl]-4-hydroxypyrrolidine-2-carboxamide, ESI 462, m.p. 127°;
N-[4-(3-oxomorpholin-4-yl)phenyl]-(2R,4R)-1-[(E)-3-(5-methylfuran-2-yl)acryloyl]-4-hydroxypyrrolidine-2-carboxamide, ESI 440, m.p. 133°;
N-[4-(3-oxomorpholin-4-yl)phenyl]-(2R,4R)-1-[(E)-3-thiophen-2-yl-acryloyl]-4-hydroxypyrrolidine-2-carboxamide, ESI 442;
N-[2-fluoro-4-(3-oxomorpholin-4-yl)phenyl]-(2R,4R)-1-[(E)-3-(5-chlorothiophen-2-yl)acryloyl]-4-methoxypyrrolidine-2-carboxamide, ESI 508;
N-[2-fluoro-4-(3-oxomorpholin-4-yl)phenyl]-(2R,4R)-1-[(E)-3-(5-chlorothiophen-2-yl)acryloyl]-4-hydroxypyrrolidine-2-carboxamide, ESI 494, m.p. 111°;
N-[4-(3-oxomorpholin-4-yl)phenyl]-(2R,4R)-1-[(E)-3-(4-chlorophenyl)-acryloyl]-4-hydroxypyrrolidine-2-carboxamide, ESI 470;
N-[4-(3-oxomorpholin-4-yl)phenyl]-(2R,4R)-1-[(E)-3-(3,4-dichloro-phenyl)acryloyl]-4-hydroxypyrrolidine-2-carboxamide, ESI 504;
N-[4-(3-oxomorpholin-4-yl)phenyl]-(2R,4R)-1-[(E)-3-(4-chlorophenyl)-acryloyl]-4-methoxypyrrolidine-2-carboxamide, ESI 484;
N-[4-(3-oxomorpholin-4-yl)phenyl]-(2R,4R)-1-[(E)-3-(3,4-dichloro-phenyl)acryloyl]-4-methoxypyrrolidine-2-carboxamide, ESI 518;
N-[4-(3-oxomorpholin-4-yl)phenyl]-(2R,4R)-1-[(E)-3-1H-imidazol-4-ylacryloyl]-4-hydroxypyrrolidine-2-carboxamide, ESI 426;
N-[4-(3-oxomorpholin-4-yl)phenyl]-(2R,4R)-1-[(E)-3-(5-chlorothiophen-2-yl)acryloyl]-4-methoxypyrrolidine-2-carboxamide, ESI 490;
N-[4-(3-oxamorpholin-4-yl)phenyl]-(2R,4R)-1-[(E)-3-(5-chlorofuran-2-yl)acryloyl]-4-hydroxypyrrolidine-2-carboxamide, ESI 460;
N-[4-(3-oxamorpholin-4-yl)phenyl]-(2R,4R)-1-[(E)-3-(5-chlorofuran-2-yl)acryloyl]-4-methoxypyrrolidine-2-carboxamide, ESI 474;
N-[4-(3-oxomorpholin-4-yl)phenyl]-(2R,4R)-1-[(E)-3-(4-chlorophenyl)-acryloyl]-4-ethoxypyrrolidine-2-carboxamide; ESI 498;
N-[4-(3-oxomorpholin-4-yl)phenyl]-(2R,4R)-1-[(E)-3-(3,4-dichloro-phenyl)acryloyl]-4-ethoxypyrrolidine-2-carboxamide, ESI 532;
N-[4-(3-oxomorpholin-4-yl)phenyl]-(2R,4R)-1-[(E)-3-(5-chlorofuran-2-yl)acryloyl]-4-ethoxypyrrolidine-2-carboxamide, ESI 488;

N-[4-(3-oxomorpholin-4-yl)phenyl]-(2R,4R)-1-[(E)-3-(5-chlorothiophen-2-yl)acryloyl]-4-ethoxypyrrolidine-2-carboxamide, ESI 504;

N-[2-fluoro-4-(3-oxomorpholin-4-yl)phenyl]-(2R,4R)-1-[(E)-3-(4-chloro-phenyl)acryloyl]-4-hydroxypyrrolidine-2-carboxamide, ESI 488;

N-[2-fluoro-4-(3-oxomorpholin-4-yl)phenyl]-(2R,4R)-1-[(E)-3-(3,4-dichlorophenyl)acryloyl]-4-hydroxypyrrolidine-2-carboxamide, ESI 522;

N-[2-fluoro-4-(3-oxomorpholin-4-yl)phenyl]-(2R,4R)-1-[(E)-3-(5-chlorofuran-2-yl)acryloyl]-4-hydroxypyrrolidine-2-carboxamide, ESI 478;

N-[2-fluoro-4-(3-oxomorpholin-4-yl)phenyl]-(2R,4R)-1-[(E)-3-(5-chlorofuran-2-yl)acryloyl]-4-methoxypyrrolidine-2-carboxamide, ESI 492;

N-[2-fluoro-4-(3-oxomorpholin-4-yl)phenyl]-(2R,4R)-1-[(E)-3-(4-chloro-phenyl)acryloyl]-4-methoxypyrrolidine-2-carboxamide, ESI 502;

N-[2-fluoro-4-(3-oxomorpholin-4-yl)phenyl]-(2R,4R)-1-[(E)-3-(3,4-dichlorophenyl)acryloyl]-4-methoxypyrrolidine-2-carboxamide, ESI 536;

N-[2-fluoro-4-(3-oxomorpholin-4-yl)phenyl]-(2R,4R)-1-[(E)-3-(4-chloro-phenyl)acryloyl]-4-ethoxypyrrolidine-2-carboxamide, ESI 516;

N-[2-fluoro-4-(3-oxamorpholin-4-yl)phenyl]-(2R,4R)-1-[(E)-3-(3,4-dichlorophenyl)acryloyl]-4-ethoxypyrrolidine-2-carboxamide, ESI 550;

N-[2-fluoro-4-(3-oxomorpholin-4-yl)phenyl]-(2R,4R)-1-[(E)-3-(5-chlorofuran-2-yl)acryloyl]-4-ethoxypyrrolidine-2-carboxamide, ESI 506;

N-[2-fluoro-4-(3-oxomorpholin-4-yl)phenyl]-(2R,4R)-1-[(E)-3-(5-chlorothiophen-2-yl)acryloyl]-4-ethoxypyrrolidine-2-carboxamide, ESI 522;

N-[4-(3-oxomorpholin-4-yl)phenyl]-(2R,4R)-1-[(E)-3-1H-imidazol-4-yl-acryloyl]-4-ethoxypyrrolidine-2-carboxamide, ESI 454;

N-[2-fluoro-4-(3-oxomorpholin-4-yl)phenyl]-(2R,4R)-1-[(E)-3-1H-imidazol-4-ylacryloyl]-4-hydroxypyrrolidine-2-carboxamide ESI 444;

N-[2-fluoro-4-(3-oxomorpholin-4-yl)phenyl]-(2R,4R)-1-[(E)-3-1H-imidazol-4-ylacryloyl]-4-methoxypyrrolidine-2-carboxamide, ESI 458;

N-[2-fluoro-4-(3-oxomorpholin-4-yl)phenyl]-(2R,4R)-1-[(E)-3-1H-imidazol-4-ylacryloyl]-4-ethoxypyrrolidine-2-carboxamide ESI 472;

N-[2-fluoro-4-(3-oxomorpholin-4-yl)phenyl]-(2R,4R)-1-[(E)-3-pyridin-3-ylacryloyl]-4-hydroxypyrrolidine-2-carboxamide, ESI 455;

N-[4-(3-oxomorpholin-4-yl)phenyl]-(2R,4R)-1-[(E)-3-pyridin-3-ylacryloyl]-4-ethoxypyrrolidine-2-carboxamide, ESI 465;

N-[2-fluoro-4-(3-oxomorpholin-4-yl)phenyl]-(2R,4R)-1-[(E)-3-pyridin-3-ylacryloyl]-4-methoxypyrrolidine-2-carboxamide, ESI 469;

N-[2-fluoro-4-(3-oxomorpholin-4-yl)phenyl]-(2R,4R)-1-[(E)-3-pyridin-3-ylacryloyl]-4-ethoxypyrrolidine-2-carboxamide, ESI 483;

N-[4-(3-oxomorpholin-4-yl)phenyl]-(2R,4R)-1-[(E)-3-pyridin-3-ylacryloyl]-4-hydroxypyrrolidine-2-carboxamide, ESI 437;

N-[4-(3-oxomorpholin-4-yl)phenyl]-(2R,4R)-1-[(E)-3-pyridin-3-ylacryloyl]-4-methoxypyrrolidine-2-carboxamide, ESI 451;

N-[4-(3-oxomorpholin-4-yl)phenyl]-(2R,4R)-1-[(E)-3-pyridin-4-ylacryloyl]-4-hydroxypyrrolidine-2-carboxamide, ESI 437;

N-[4-(3-oxomorpholin-4-yl)phenyl]-(2R,4R)-1-[(E)-3-pyridin-4-ylacryloyl]-4-ethoxypyrrolidine-2-carboxamide, ESI 465;

N-[4-(3-oxomorpholin-4-yl)phenyl]-(2R,4R)-1-[(E)-3-1H-imidazol-4-yl-acryloyl]-4-methoxypyrrolidine-2-carboxamide, ESI 440;

N-[4-(3-oxomorpholin-4-yl)phenyl]-(2R,4R)-1-[(E)-3-(4-bromothiophen-2-yl)acryloyl]-4-hydroxypyrrolidine-2-carboxamide, ESI 521;

N-[4-(3-oxomorpholin-4-yl)phenyl]-(2R,4R)-1-[(E)-3-(4-bromothiophen-2-yl)acryloyl]-4-ethoxypyrrolidine-2-carboxamide, ESI 549;

N-[4-(3-oxomorpholin-4-yl)phenyl]-(2R,4R)-1-[(E)-3-(5-bromothiophen-2-yl)acryloyl]-4-hydroxypyrrolidine-2-carboxamide, ESI 521;

N-[4-(3-oxomorpholin-4-yl)phenyl]-(2R,4R)-1-[(E)-3-(5-bromothiophen-2-yl)acryloyl]-4-ethoxypyrrolidine-2-carboxamide, ESI 549.

EXAMPLE 13-1a

The following compounds are obtained analogously to Example 7

N-(4-chlorophenyl)-(R)-1-[4-(2-oxopiperidin-1-yl)benzoyl]pyrrolidine-2-carboxamide, ESI 426;

N-(4-chlorophenyl)-(S)-1-[4-(2-oxopiperidin-1-yl)benzoyl]pyrrolidine-2-carboxamide, ESI 426;

1-N-[(4-chlorophenyl)]-2-N-{[4-(5-oxo-1,4-oxazepan-4-yl)phenyl]}-(R)-pyrrolidine-1,2-dicarboxamide, ESI 457;

1-N-[(4-chlorophenyl)]-2-N-{[4-(5-oxo-1,4-oxazepan-4-yl)phenyl]}-(2R,4R)-4-hydroxypyrrolidine-1,2-dicarboxamide, ESI 473;

1-N-[(4-chlorophenyl)]-2-N-{[4-((S)-2-methyl-3-oxomorpholin-4-yl)-phenyl]}-(2R,4R)-4-hydroxypyrrolidine-1,2-dicarboxamide, ESI 473;

1-N-[(4-chlorophenyl)]-2-N-{[4-((S)-2-methyl-3-oxomorpholin-4-yl)-phenyl]}-(2R)-pyrrolidine-1,2-dicarboxamide, ESI 457;

1-N-[(4-chlorophenyl)]-2-N-{[4-((R)-2-methyl-3-oxomorpholin-4-yl)-phenyl]}-(2R,4R)-4-hydroxypyrrolidine-1,2-dicarboxamide, ESI 473;

1-N-[(4-chlorophenyl)]-2-N-{[4-((R)-2-methyl-3-oxomorpholin-4-yl)-phenyl]}-(2R)-pyrrolidine-1,2-dicarboxamide, ESI 457;

1-N-[(4-chlorophenyl)]-2-N-{[4-(3-oxomorpholin-4-yl)-2-phenoxy-phenyl]}-(2R)-pyrrolidine-1,2-dicarboxamide, ESI 535;

1-N-[(4-chlorophenyl)]-2-N-{[2-fluoro-4-((R)-2-methyl-3-oxomorpholin-4-yl)phenyl]}-(2R,4R)-4-hydroxypyrrolidine-1,2-dicarboxamide, ESI 491;

1-N-[(4-chlorophenyl)]-3-N-{[4-(3-oxomorpholin-4-yl)phenyl]}-piperidine-1,3-dicarboxamide, ESI 457;

1-N-[(4-chlorophenyl)]-3-N-{[3-methyl-4-(3-oxomorpholin-4-yl)-phenyl]}piperidine-1,3-dicarboxamide, ESI 471;

1-N-[(4-chlorophenyl)]-2-N-{[4-(3-oxo-1,4-oxazepan-4-yl)phenyl]}-(2R,4R)-4-hydroxypyrrolidine-1,2-dicarboxamide, ESI 473;

1-N-[(4-chlorophenyl)]-2-N-{[2-methyl-4-(3-oxomorpholin-4-yl)-phenyl]}-(2R,4R)-4-hydroxypyrrolidine-1,2-dicarboxamide, ESI 473;

1-N-[(4-chlorophenyl)]-2-N-{[4-(3-oxomorpholin-4-yl)phenyl]}-(2R,4R)-4-hydroxypyrrolidine-1,2-dicarboxamide, ESI 459;

1-N-[(4-chlorophenyl)]-2-N-{[2-(3-oxomorpholin-4-yl)phenyl]}-(2R,4R)-4-hydroxypyrrolidine-1,2-dicarboxamide, ESI 459.

EXAMPLE 13-14

The following compounds are obtained analogously to Example 7

N-[4-(3-oxomorpholin-4-yl)phenyl]-(rac)-2-[3-(4-chlorophenyl)ureido]-cyclopentanecarboxamide, ESI 457

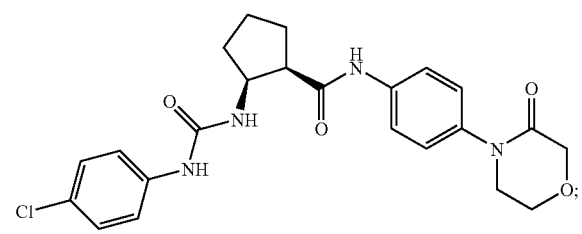

N-[3-methyl-4-(3-oxomorpholin-4-yl)phenyl]-(rac)-2-[3-(4-chloro-phenyl)ureido]cyclopentanecarboxamide, ESI 471.

EXAMPLE 13-15

1-N-[(4-chlorophenyl)]-2-N-{[4-(3-oxomorpholin-4-yl)phenyl]}-(2R,4R)-4-(2-methoxyethoxy)pyrrolidine-1,2-dicarboxamide, ESI 517, is prepared as described below

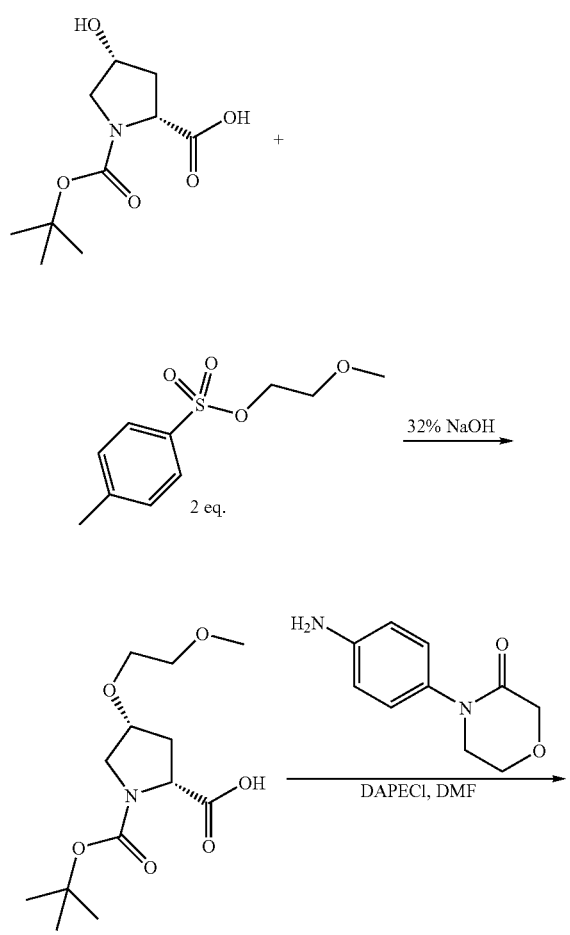

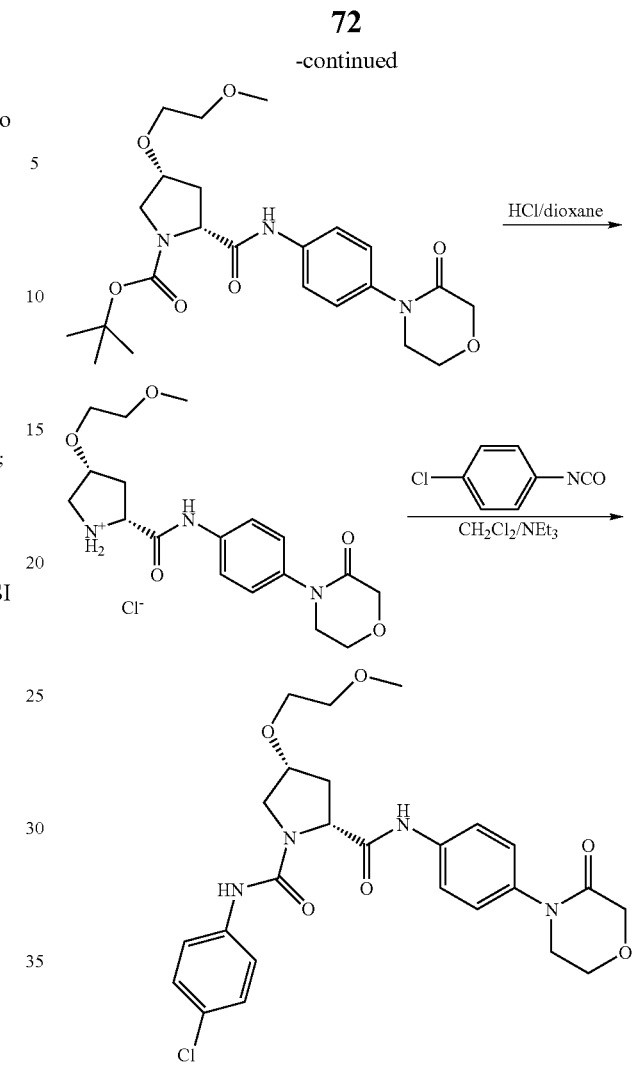

14. Examples of the Preparation of Intermediate Compounds 14.1 All compounds of the following formula VI (where R=H or methyl; n=3, 4 or 5) can be synthesised in accordance with the following scheme.

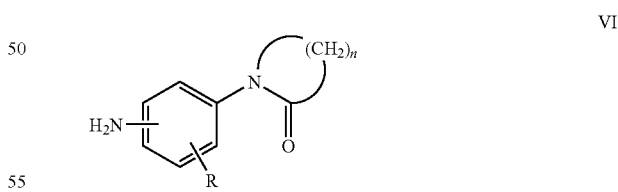

For example, synthesis of 1-(4-amino-2-methylphenyl)piperidin-2-one:

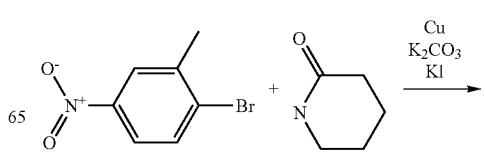

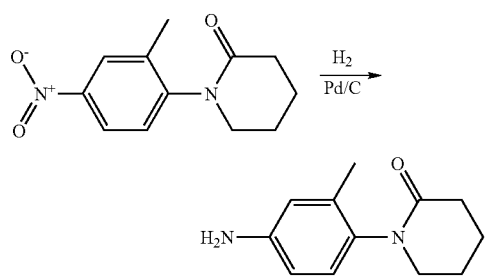
14.2 Synthesis of the Phenylpiperidone Unit without a Methyl Group:
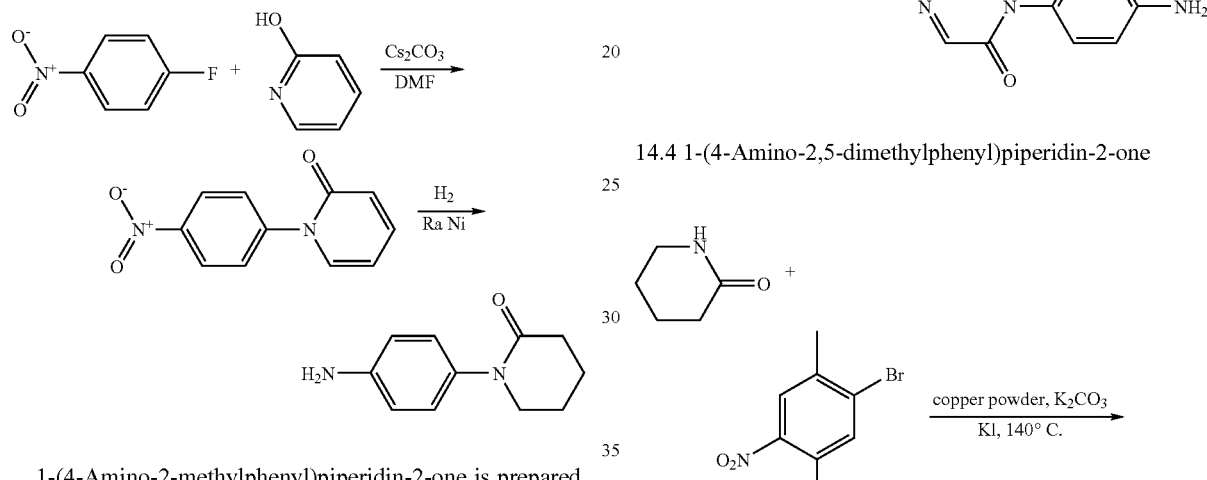
1-(4-Amino-2-methylphenyl)piperidin-2-one is prepared, for example, as indicated below:
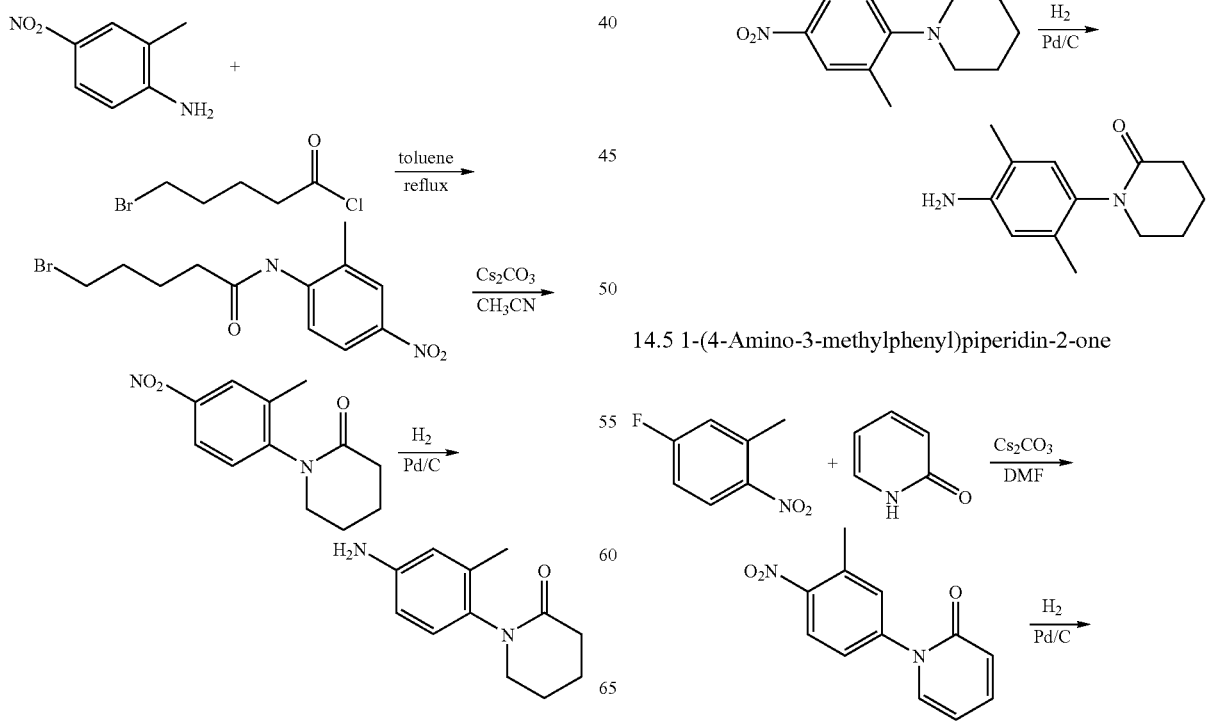
14.3 1-(4-Aminophenyl)-1H-pyrazin-2-one
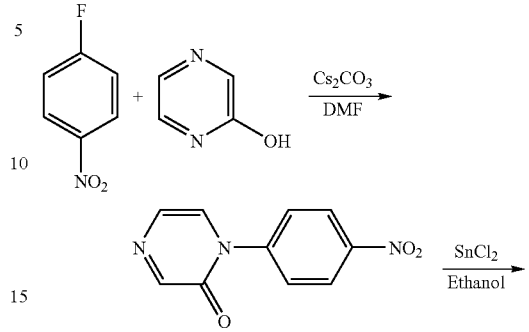
14.4 1-(4-Amino-2,5-dimethylphenyl)piperidin-2-one
14.5 1-(4-Amino-3-methylphenyl)piperidin-2-one -continued
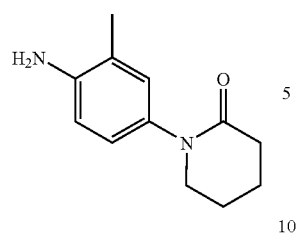
14.6 1-(5-Aminopyridin-2-yl)piperidin-2-one
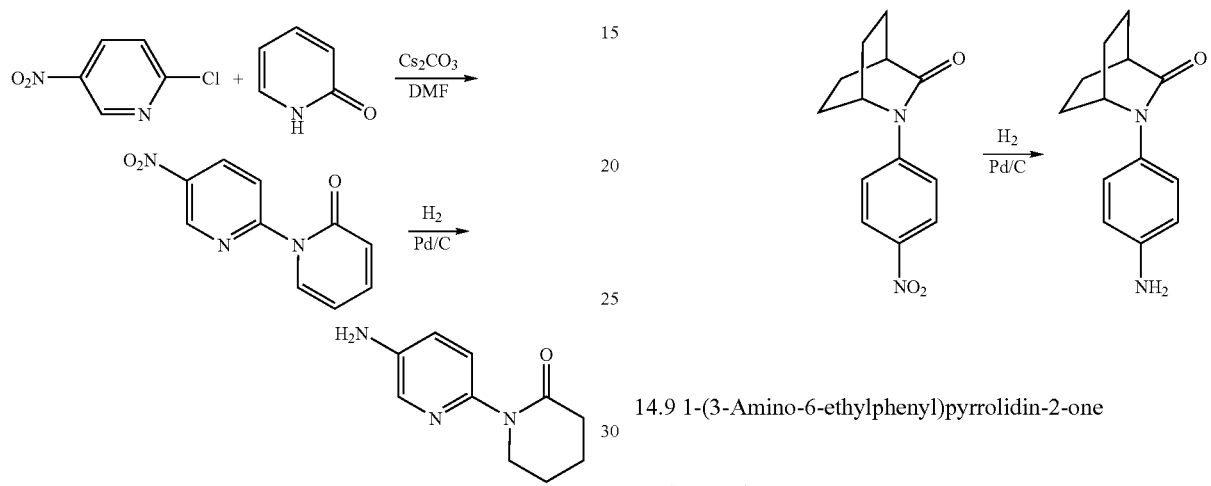
14.7 1-(4-Aminomethylphenyl)piperidin-2-one
14.8 2-(4-Aminophenyl)-2-azabicyclo[2.2.2]octan-3-one
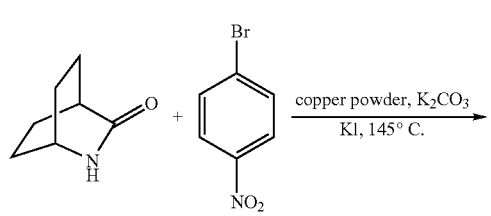
14.9 1-(3-Amino-6-ethylphenyl)pyrrolidin-2-one
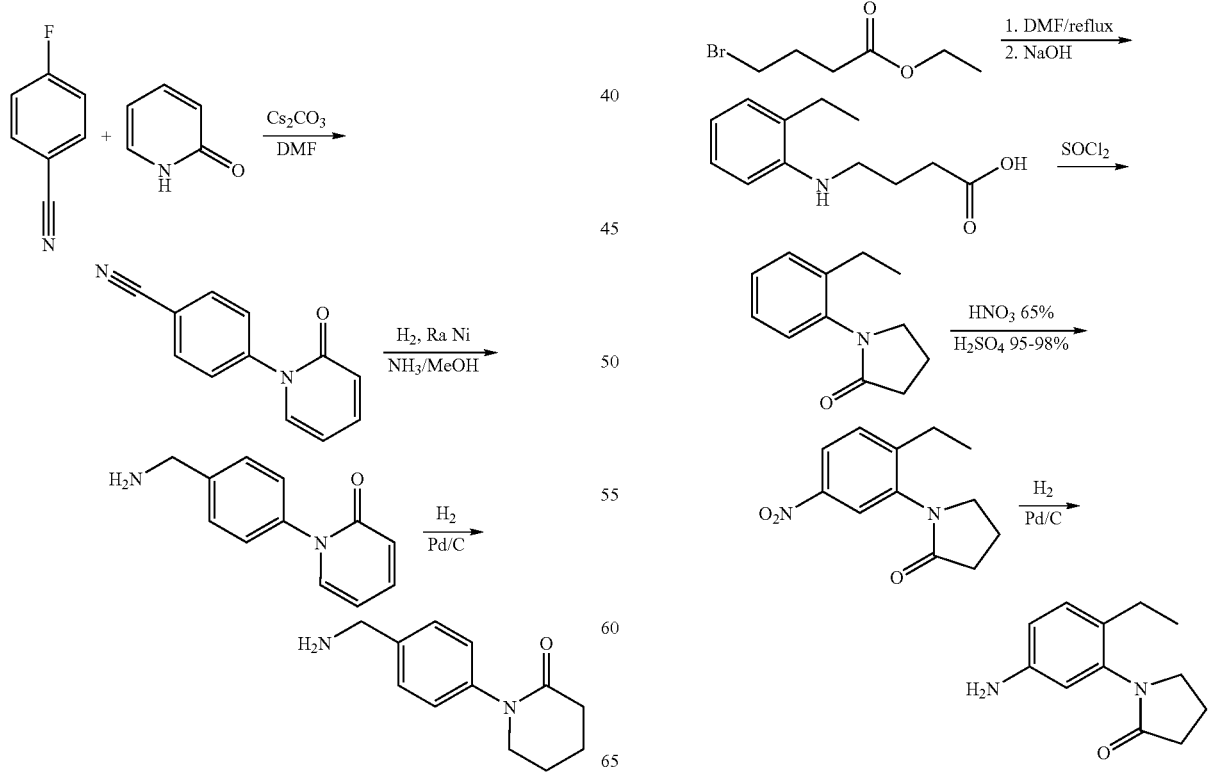

14.10  2-(4-Amino-2-trifluoromethylphenyl)-2-azabicyclo(2.2.2)octan-3-one
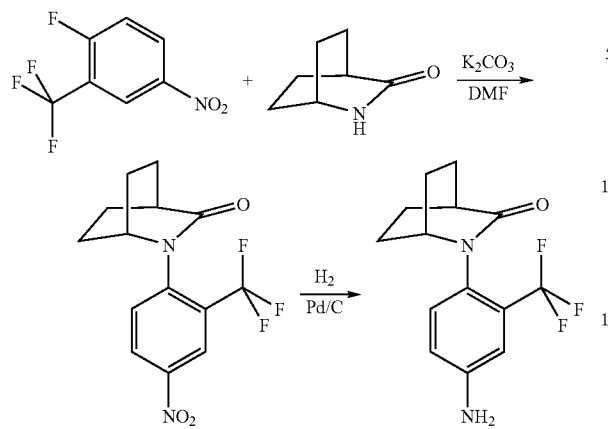
14.11  1-(4-Amino-3-chlorophenyl)pyrrolidin-2-one
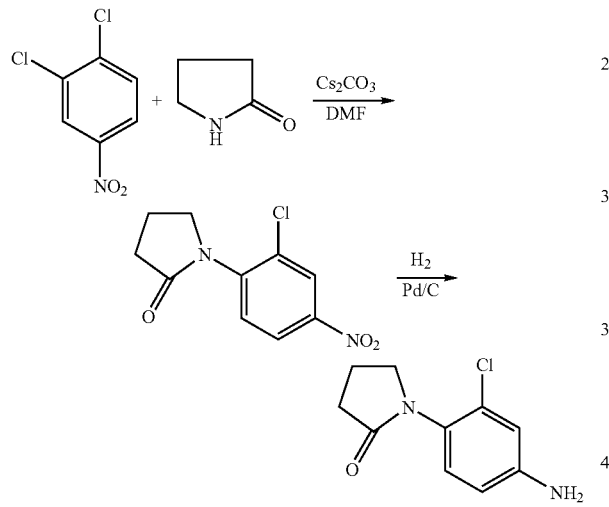
14.12  1-(4-Amino-2-trifluoromethylphenyl)piperidin-2-one
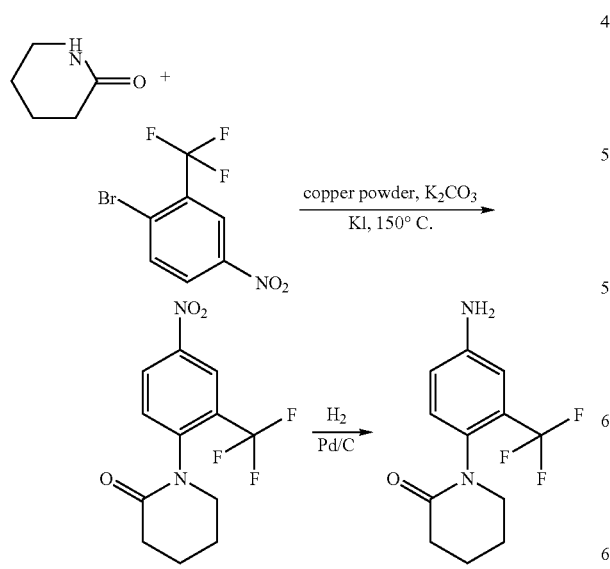
14.13  3-(4-Amino-2-methylphenyl)-1,3-oxazinan-2-one
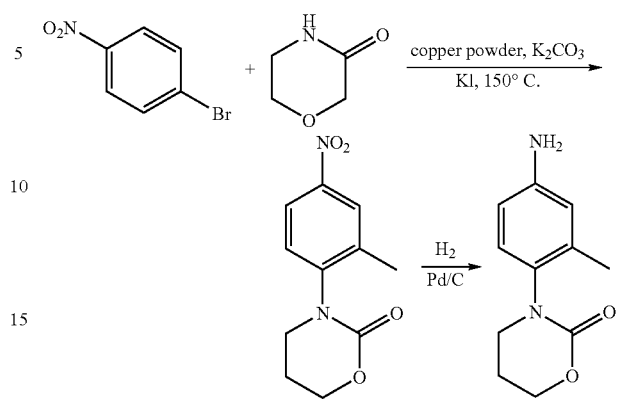
14.14  4-(4-Aminophenyl)morpholin-3-one
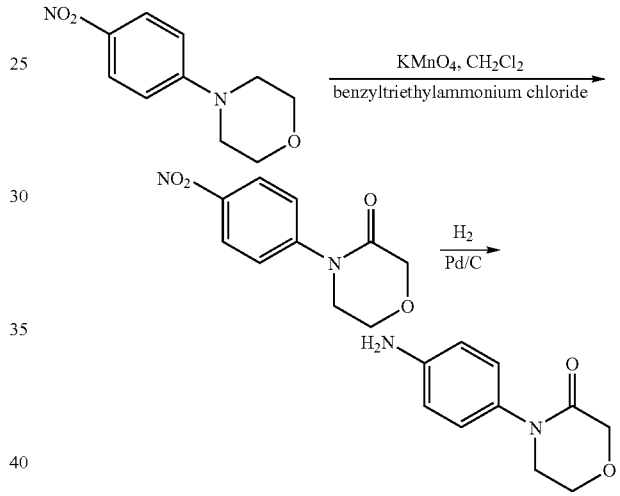
14.15  1-(4-Aminophenyl)pyridin-2-one
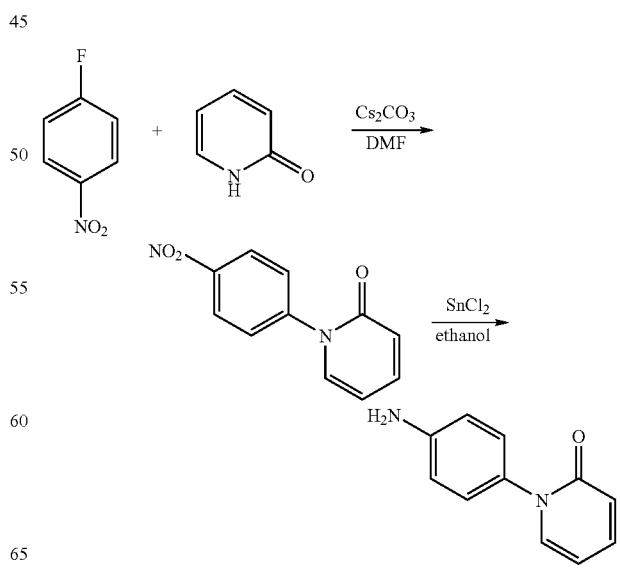

14.16 1-(4-Amino-2-methylphenyl)piperidin-2-one
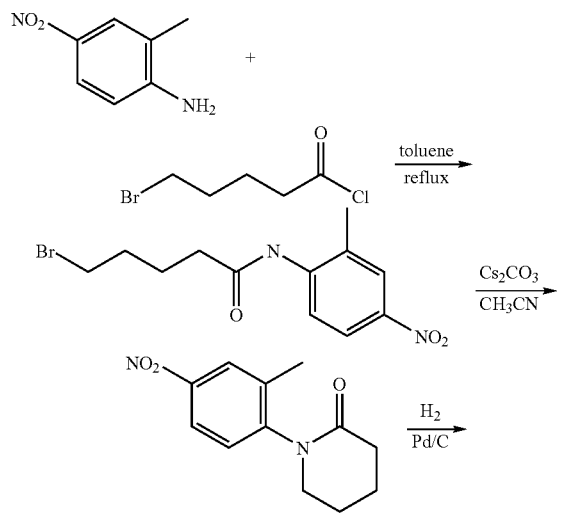
14.17 1-(4-Aminophenyl)-1H-pyridin-4-one
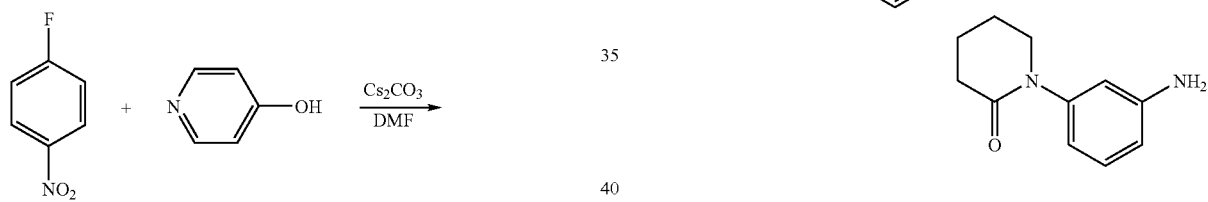
14.18 1-(4-Aminophenyl)-4-tert-butyloxycarbonylpiperazin-2-one
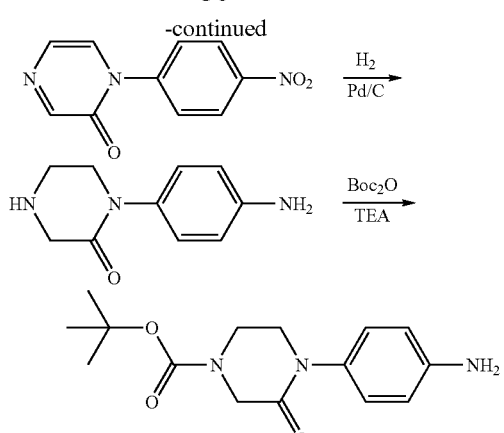
14.19 1-(3-Aminophenyl)piperidin-2-one
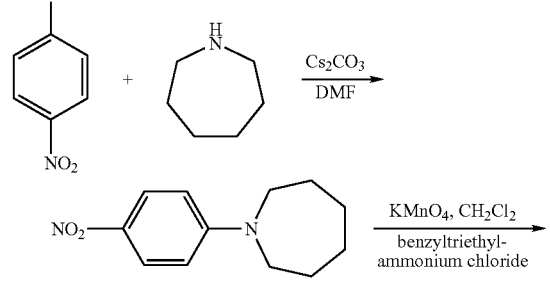
14.20 1-(4-Aminophenyl)-2-caprolactam
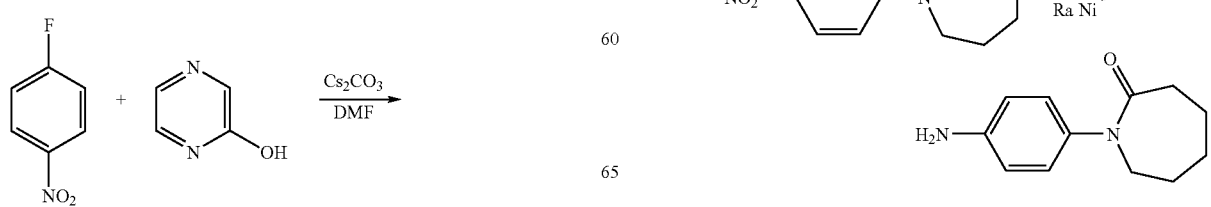

14.21 1-(4-Amino-3-fluorophenyl)piperidin-2-one
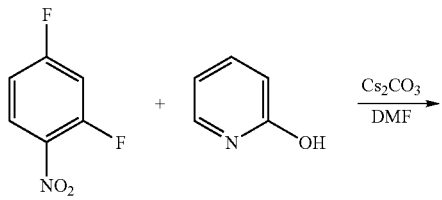
14.22 1-(4-Amino-2-fluorophenyl)piperidin-2-one
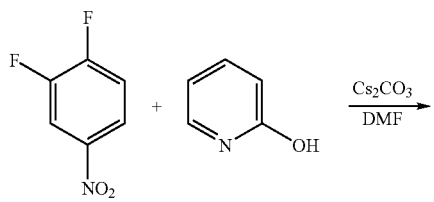
14.23 1-(4-Amino-2-fluorophenyl)-2-caprolactam
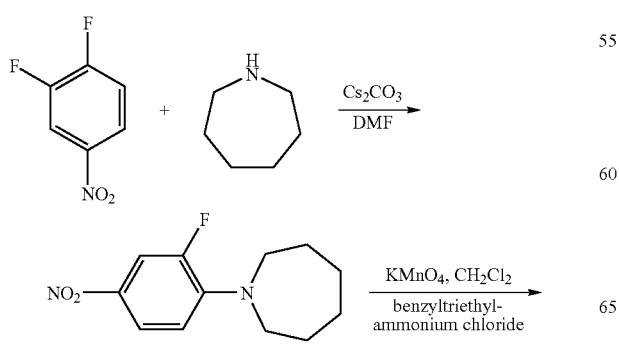
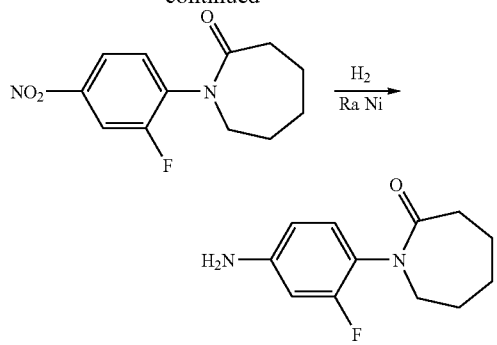
14.24 4-(4-Amino-2-fluorophenyl)-1,4-oxazepan-5-one
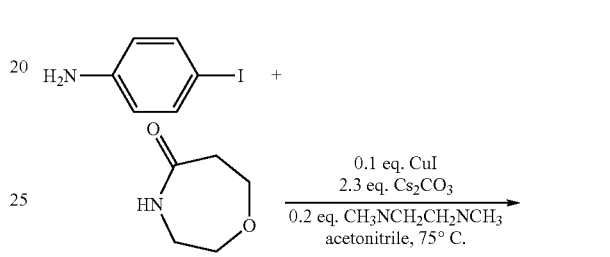
14.25 4-(4-Amino-3-phenoxyphenyl)morpholin-3-one
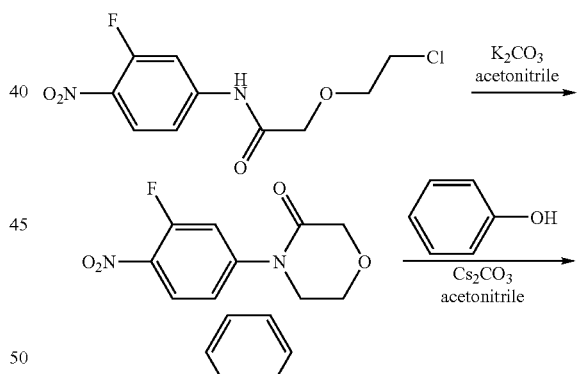

14.26 2-[3-(4-Chlorophenyl)ureido]cyclopentanecarboxylic acid

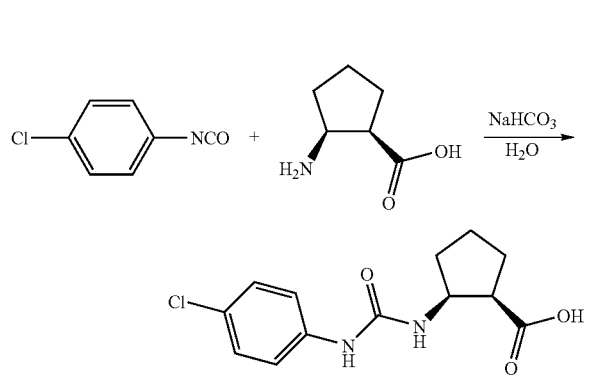

14.27 1-(4-Chlorophenylcarbamoyl)piperidine-3-carboxylic acid

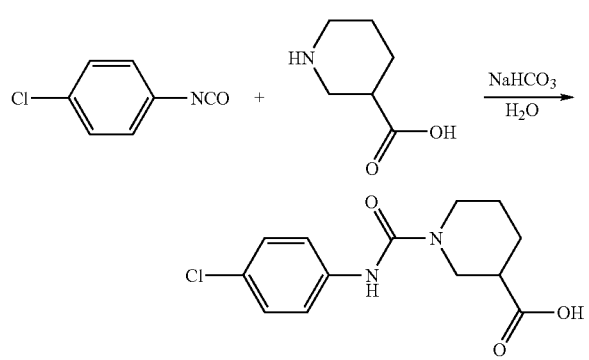

14.28 4-(4-Aminophenyl)-1,4-oxazepan-3-one

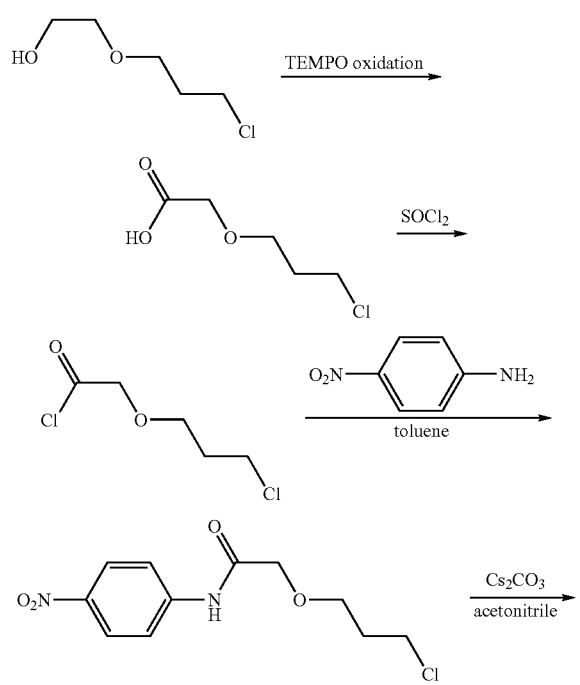

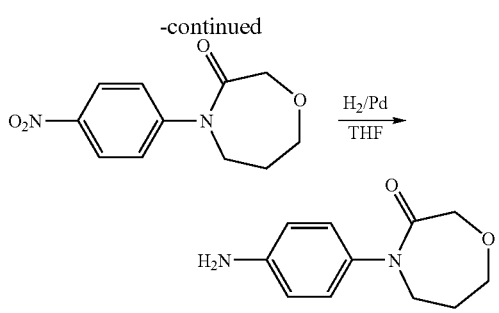

The TEMPO oxidation is carried out in accordance with the following literature:
L. DeLuca et al., J. Org. Chem. 68, 4999-5001 (2003).

Pharmacological Data:
Affinity to Receptors

TABLE 1

| Compound No. | FXa-IC$_{50}$ [M] | TF/FVIIa-IC$_{50}$ [M] |
|---|---|---|
| "A1" | $1.8 \times 10^{-8}$ | $2.3 \times 10^{-8}$ |
| "A2" | $2.7 \times 10^{-8}$ | |
| "AB1" | $1.8 \times 10^{-6}$ | $3.9 \times 10^{-6}$ |
| "A6" | $3.7 \times 10^{-9}$ | |

The following examples relate to pharmaceutical preparations:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2H$_2$O, 28.48 g of Na$_2$HPO$_4$.2H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A method for the treatment of a patient suffering from thromboses, comprising administering to said patient an effective amount of a compound according to formula I

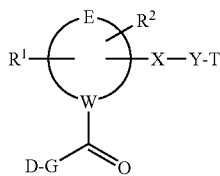

I in which
$R^1$ is H, =O, COOR$^3$, OH, OA, NH$_2$, alkyl having 1, 2, 3, 4, 5 or 6 carbon atoms, N$_3$, ethynyl, vinyl, allyloxy, —OCOR$^3$, NHCOA or NHSO$_2$A,
$R^2$ is H, =O, OH, OA or alkyl having 1, 2, 3, 4, 5 or 6 carbon atoms,
$R^1$ and $R^2$ together can also be a spirocyclically bonded 3- to 6-membered carbocyclic ring,
$R^3$ is H or A,

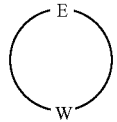

is pyrrolidine-1,2-diyl, piperidine-1,2-diyl, oxazolidine-3,4- or 3,5-diyl, thiazolidine-3,4-diyl, 2,5-dihydro-1H-pyrrole-1, 5-diyl, 1,3-dioxolane-4,5-diyl, 1,3-oxazinane-3,4-diyl, piperazine-1,4-diyl, tetrahydrofuran-3,4-diyl or azetidine-1,2-diyl,
D is phenyl, pyridyl or thienyl, which in each case is monosubstituted or disubstituted by Hal,
G is (CH$_2$)$_n$ or (CH$_2$)$_n$NH—,
X is CONH,
Y is 1,3- or 1,4-phenylene which is unsubstituted or monosubstituted or disubstituted by methyl, trifluoromethyl, ethyl, propyl, Cl or F,
T is morpholin-4-yl, which is monosubstituted or disubstituted by carbonyl oxygen,
A is unbranched or branched alkyl having 1-10 carbon atoms and in which 1-7H atoms are each optionally replaced by F,
Hal is F, Cl, Br or I, and
n is 0, 1 or 2;
or a pharmaceutically usable salt or stereoisomer thereof, including mixtures thereof in all ratios.

2. The method according to claim 1 wherein $R^1$ and $R^2$ are each, independently of one another, H, OH, OA, or alkyl having 1, 2, 3, 4, 5 or 6 carbon atoms.

3. The method according to claim 1, wherein said compound is selected from:
1-N-[(4-chlorophenyl)]-2-N-{[4-(3-oxomorpholin-4-yl) phenyl]}-(R)-pyrrolidine-1,2-dicarboxamide,
1-N-[(4-chlorophenyl)]-2-N-{[3-methyl-4-(3-oxomorpholin-4-yl)phenyl]}-(R)-pyrrolidine-1,2-dicarboxamide,
1-N-[(4-chlorophenyl)]-2-N-{[3-fluoro-4-(3-oxomorpholin-4-yl)phenyl]}-(R)-pyrrolidine-1,2-dicarboxamide,
1-N-[(4-chlorophenyl)]-2-N-{[2-fluoro-4-(3-oxomorpholin-4-yl)phenyl]}-(R)-pyrrolidine-1,2-dicarboxamide,
1-N-[(4-chlorophenyl)]-2-N-{[3-trifluoromethyl-4-(3-oxomorpholin-4-yl)phenyl]}-(R)-pyrrolidine-1,2-dicarboxamide,
1-N-[(4-chlorophenyl)]-2-N-{[3-methyl-4-(3-oxomorpholin-4-yl)phenyl]}-(R)-piperidine-1,2-dicarboxamide,
1-N-[(4-chlorophenyl)]-2-N-{[4-(3-oxomorpholin-4-yl) phenyl]}-(R)-2,5-dihydropyrrole-1,2-dicarboxamide,
N-[4-(3-oxomorpholin-4-yl)phenyl]-(R)-1-(5-chlorothiophene-2-carbonyl)pyrrolidine-2-carboxamide,
N-[3-methyl-4-(3-oxomorpholin-4-yl)phenyl]-(R)-1-(5-chlorothiophene-2-carbonyl)pyrrolidine-2-carboxamide,
3-N-[(4-chlorophenyl)]-4-N-{[4-(3-oxomorpholin-4-yl) phenyl]}-(R)-oxazolidine-3,4-dicarboxamide,
3-N-[(4-chlorophenyl)]-4-N-{[3-methyl-4-(3-oxomorpholin-4-yl)phenyl]}-(R)-oxazolidine-3,4-dicarboxamide, 3-N-[(4-chlorophenyl)]-4-N-{[4-(3-oxomorpholin-4-yl)phenyl]}-(4R,5S)-5-methyloxazolidine-3,4-dicarboxamide,
3-N-[(4-chlorophenyl)-4-N-{[3-methyl-4-(3-oxomorpholin-4-yl)phenyl]}-(4R,5S)-5-methyloxazolidine-3,4-dicarboxamide,
3-N-[(4-chlorophenyl)]-4-N-{[3-fluoro-4-(3-oxomorpholin-4-yl)phenyl]}-(4R,5S)-5-methyloxazolidine-3,4-dicarboxamide,
3-N-[(4-chlorophenyl)]-4-N-{[3-chloro-4-(3-oxomorpholin-4-yl)phenyl]}-(4R,5S)-5-methyloxazolidine-3,4-dicarboxamide,
3-N-[(4-chlorophenyl)]-4-N-{[3-methyl-4-(3-oxomorpholin-4-yl)phenyl]}-(4R,5R)-5-methyloxazolidine-3,4-dicarboxamide,
3-N-[(4-chlorophenyl)]-4-N-{[4-(3-oxomorpholin-4-yl)phenyl]}-(S)-thiazolidine-3,4-dicarboxamide,
3-N-[(4-chlorophenyl)-4-N-{[4-(3-oxomorpholin-4-yl)phenyl]}-(S)-1,1-dioxo-1$\lambda^6$-thiazolidine-3,4-dicarboxamide,
3-N-[(4-chlorophenyl)]-4-N-{[3-methyl-4-(3-oxomorpholin-4-yl)phenyl]}-(S)-thiazolidine-3,4-dicarboxamide,
3-N-[(4-chlorophenyl)]-4-N-{[3-methyl-4-(3-oxomorpholin-4-yl)phenyl]}-(S)-1,1-dioxo-1$\lambda^6$-thiazolidine-3,4-dicarboxamide,
N-[4-(3-oxomorpholin-4-yl)phenyl]-3-(5-chlorothiophene-2-carbonyl)oxazolidine-5-carboxamide,
N-[3-methyl-4-(3-oxomorpholin-4-yl)phenyl]-3-(5-chlorothiophene-2-carbonyl)oxazolidine-5-carboxamide,
1-N-[(5-chloropyridin-2-yl)]-2-N-{[4-(3-oxomorpholin-4-yl)phenyl]}-(2R,4R)-4-hydroxypyrrolidine-1,2-dicarboxamide,
1-N-[(5-chloropyridin-2-yl)]-2-N-{[4-(3-oxomorpholin-4-yl)phenyl]}-(R)-4,4-dimethoxypyrrolidine-1,2-dicarboxamide,
1-N-[(4-chlorophenyl)]-2-N-{[4-(3-oxomorpholin-4-yl)phenyl]}-(2R,4R)-4-hydroxypyrrolidine-1,2-dicarboxamide,
1-N-[(4-chlorophenyl)]-2-N-{[3-methyl-4-(3-oxomorpholin-4-yl)phenyl]}-(2R,4R)-4-hydroxypyrrolidine-1,2-dicarboxamide,
1-N-[(4-chlorophenyl)]-2-N-{[2-fluoro-4-(3-oxomorpholin-4-yl)phenyl]}-(2R,4R)-4-hydroxypyrrolidine-1,2-dicarboxamide,
1-N-[(4-chlorophenyl)]-2-N-{[3-fluoro-4-(3-oxomorpholin-4-yl)phenyl]}-(2R,3R)-3-hydroxypyrrolidine-1,2-dicarboxamide,
1-N-[(4-chlorophenyl)]-2-N-{[3-fluoro-4-(3-oxomorpholin-4-yl)phenyl]}-(2R,3S)-3-hydroxypyrrolidine-1,2-dicarboxamide,
1-N-[(4-chlorophenyl)]-2-N-{[4-(3-oxomorpholin-4-yl)phenyl]}-(2R,4S)-4-hydroxypyrrolidine-1,2-dicarboxamide,
1-N-[(4-chlorophenyl)]-2-N-{[4-(3-oxomorpholin-4-yl)phenyl]}-(2S,4R)-4-hydroxypyrrolidine-1,2-dicarboxamide,
1-N-[(4-chlorophenyl)]-2-N-{[4-(3-oxomorpholin-4-yl)phenyl]}-3,4-dihydroxypyrrolidine-1,2-dicarboxamide,
1-N-[(4-chlorophenyl)]-2-N-{[4-(3-oxomorpholin-4-yl)phenyl]}-(2R,4S)-4-azidopyrrolidine-1,2-dicarboxamide,
1-N-[(4-chlorophenyl)]-2-N-{[4-(3-oxomorpholin-4-yl)phenyl]}-(2R,4S)-4-aminopyrrolidine-1,2-dicarboxamide,
1-N-[(4-chlorophenyl)]-2-N-{[4-(3-oxomorpholin-4-yl)phenyl]}-(2R,4R)-4-azidopyrrolidine-1,2-dicarboxamide,
1-N-[(4-chlorophenyl)]-2-N-{[4-(3-oxomorpholin-4-yl)phenyl]}-(2R,4R)-4-aminopyrrolidine-1,2-dicarboxamide,
1-N-[(4-chlorophenyl)]-2-N-{[4-(3-oxomorpholin-4-yl)phenyl]}-(2R,4S)-4-acetaminopyrrolidine-1,2-dicarboxamide,
1-N-[(4-chlorophenyl)]-2-N-{[4-(3-oxomorpholin-4-yl)phenyl]}-(2R,4R)-4-acetaminopyrrolidine-1,2-dicarboxamide,
1-N-[(4-chlorophenyl)]-2-N-{[4-(3-oxomorpholin-4-yl)phenyl]}-(2R,4S)-4-methylsulfonylaminopyrrolidine-1,2-dicarboxamide,
1-N-[(4-chlorophenyl)]-2-N-{[4-(3-oxomorpholin-4-yl)phenyl]}-(2R,4R)-4-methylsulfonylaminopyrrolidine-1,2-dicarboxamide,
1-N-[(4-chlorophenyl)]-2-N-{[4-(3-oxomorpholin-4-yl)phenyl]}-(2R,4R)-4-methoxypyrrolidine-1,2-dicarboxamide,
1-N-[(4-chlorophenyl)]-2-N-{[4-(3-oxomorpholin-4-yl)phenyl]}-(2R,4R)-4-ethoxypyrrolidine-1,2-dicarboxamide,
1-N-[(4-chlorophenyl)]-2-N-{[4-(3-oxomorpholin-4-yl)phenyl]}-(2R,4R)-4-propoxypyrrolidine-1,2-dicarboxamide,
1-N-[(4-chlorophenyl)]-2-N-{[4-(3-oxomorpholin-4-yl)phenyl]}-(2R,4R)-4-allyloxypyrrolidine-1,2-dicarboxamide,
(3R,5R)-1-(4-chlorophenylcarbamoyl)-5-[4-(3-oxomorpholin-4-yl)-phenylcarbamoyl]pyrrolidin-3-yl isobutyrate,
(3R,5R)-1-(4-chlorophenylcarbamoyl)-5-[4-(3-oxomorpholin-4-yl)-phenylcarbamoyl]pyrrolidin-3-yl propionate,
(3R,5R)-1-(4-chlorophenylcarbamoyl)-5-[4-(3-oxomorpholin-4-yl)-phenylcarbamoyl]pyrrolidin-3-yl acetate,
4-N-[(4-chlorophenyl)]-5-N-{[4-(3-oxomorpholin-4-yl)phenyl]}-1,3-dioxolane-4,5-dicarboxamide,
4-N-[(4-chlorophenyl)]-5-N-{[3-methyl-4-(3-oxomorpholin-4-yl)phenyl]{-1,3-dioxolane-4,5-dicarboxamide,
4-N-[(4-chlorophenyl)]-5-N-{[4-(3-oxomorpholin-4-yl)phenyl]}-1,3-dioxolane-2,2-dimethyl-4,5-dicarboxamide,
4-N-[(4-chlorophenyl)]-5-N-{[3-methyl-4-(3-oxomorpholin-4-yl)phenyl]{-1,3-dioxolane-2,2-dimethyl-4,5-dicarboxamide,
1-N-[4-chlorophenyl)]-2-N-{[4-(3-oxomorpholin-4-yl)phenyl]}-1-BOC-piperazine-1,2-dicarboxamide,
1-N-[4-chlorophenyl)]-2-N-{[4-(3-oxomorpholin-4-yl)phenyl]}piperazine-1,2-dicarboxamide,
1-N-[(4-chlorophenyl)]-2-N-{[4-(3-oxomorpholin-4-yl)phenyl]}-1,3-oxazinane-3,4-dicarboxamide,
1-N-[(4-chlorophenyl)]-2-N-{[4-(3-oxomorpholin-4-yl)phenyl]}-(2R,4S)-4-ethynyl-4-hydroxypyrrolidine-1,2-dicarboxamide,
6-N-[(4-chlorophenyl)]-7-N-{[4-(3-oxomorpholin-4-yl)phenyl]}-4-oxa-6-azaspiro[2,4]heptane-6,7-dicarboxamide,
1-N-[(4-chlorophenyl)]-2-N-[{3-methyl-4-(3-oxomorpholin-4-yl)phenyl]}-(2R,4S)-4-acetaminopyrrolidine-1,2-dicarboxamide,
1-N-[(4-chlorophenyl)]-2-N-{[4-(3-oxomorpholin-4-yl)phenyl]}-(2R,4S)-4-butylsulfonylaminopyrrolidine-1,2-dicarboxamide, 1-N-[(4-chlorophenyl)]-2-N-{[4-(3-oxomorpholin-4-yl)phenyl]}-(R)-4-oxopyrrolidine-1,2-dicarboxamide, 1-N-[(4-chlorophenyl)]-2-N-[{3-methyl-4-(3-oxomorpholin-4-yl)phenyl]}-(2R,4S)-4-aminopyrrolidine-1,2-dicarboxamide, 1-N-[(4-chlorophenyl)]-2-N-[{3-methyl-4-(3-oxomorpholin-4-yl)phenyl]}-(S)-pyrrolidine-1,2-dicarboxamide, 1-N-[(4-chlorophenyl)]-2-N-{[2-fluoro-4-(3-oxomorpholin-4-yl)phenyl]}-(2R,4R)-4-hydroxypyrrolidine-1,2-dicarboxamide, N-[4-(3-oxomorpholin-4-yl)phenyl]-(2R,4R)-1-[2-(4-chlorophenyl)acetyl]-4-hydroxypyrrolidine-2-carboxamide, N-[4-(3-oxomorpholin-4-yl)phenyl]-(2R,4R)-1-(4-chlorobenzoyl)-4-hydroxypyrrolidine-2-carboxamide, 1-N-[(4-chlorophenyl)]-2-N-[{3-methyl-4-(3-oxomorpholin-4-yl)phenyl]}-(2R,4R)-4-methoxypyrrolidine-1,2-dicarboxamide, 1-N-[(4-chlorophenyl)]-2-N-{[2-fluoro-4-(3-oxomorpholin-4-yl)phenyl]}-(2R,4R)-4-methoxypyrrolidine-1,2-dicarboxamide, 1-N-[(4-chlorophenyl)]-2-N-{[4-(3-oxomorpholin-4-yl)phenyl]}-(2R,4S)-4-(2-methylpropanoylamino)pyrrolidine-1,2-dicarboxamide, N-[4-(3-oxomorpholin-4-yl)phenyl]-(2R,4R)-1-(1-1H-indol-3-ylmethanoyl)-4-hydroxypyrrolidine-2-carboxamide, N-[4-(3-oxomorpholin-4-yl)phenyl]-(2R,4R)-1-(1-1H-indol-6-ylmethanoyl)-4-hydroxypyrrolidine-2-carboxamide, 1-N-[(4-chlorophenyl)]-2-N-[{3-methyl-4-(3-oxomorpholin-4-yl)phenyl]}-(2R,4R)-4-ethoxypyrrolidine-1,2-dicarboxamide, 1-N-[(4-chlorophenyl)]-2-N-{[2-fluoro-4-(3-oxomorpholin-4-yl)phenyl]}-(2R,4R)-4-ethoxypyrrolidine-1,2-dicarboxamide, 2-N-[(4-chlorophenyl)]-1-N-{[4-(3oxomorpholin-4-yl)phenyl]}-(R)-pyrrolidine-1,2-dicarboxamide, 2-N-[(4-chlorophenyl)]-1-N-{[4-(3oxomorpholin-4-yl)phenyl]}-(S)-pyrrolidine-1,2-dicarboxamide, N-(4-chlorophenyl)-(R)-1-{2-[4(3-oxomorpholin-4-yl)phenyl]acetyl}pyrrolidine-2-carboxamide, N-(4-chlorophenyl)-(S)-1-{2-[4-(3-oxomorpholin-4-yl)phenyl]acetyl}pyrrolidine-2-carboxamide, N-(4-chlorophenyl)-(2R,4R)-1-{2-[4(3-oxomorpholin-4-yl)phenyl]acetyl}-4-methoxypyrrolidine-2-carboxamide, N-(4-chlorophenyl)-(2R,4S)-1-{2-[4(3-oxomorpholin-4-yl)phenyl]acetyl}-4-methoxypyrrolidine-2-carboxamide, N-(4-chlorophenyl)-(2S ,4R)-1-{2-[4(3-oxomorpholin-4-yl)phenyl]acetyl}-4-methoxypyrrolidine-2-carboxamide, 1-N-[(4-chlorophenyl)]-2-N-{[3-fluoro-4-(3-oxomorpholin-4-yl)phenyl]}-(2R,4R)-4-ethoxypyrrolidine-1,2-dicarboxamide, 1-N-[(4-chlorophenyl)]-2-N-{[4-(3-oxomorpholin-4-yl)phenyl]}-(2R,4R)-4-(prop-2-ynyloxy)pyrrolidine-1,2-dicarboxamide, 1-N-[(4-chlorophenyl)]-2-N-{[4-(3-oxomorpholin-4-yl)phenyl]}-(2R,4R)-4-(but-2-ynyloxy)pyrrolidine-1,2-dicarboxamide, 1-N-[(4-chlorophenyl)]-2-N-{[4-(3-oxomorpholin-4-yl)phenyl]}-(2R,4R)-4-(2,3-dihydroxypropoxy)pyrrolidine-1,2-dicarboxamide, 1-N-[(4-chlorophenyl)]-2-N-{[4-(3-oxomorpholin-4-yl)phenyl]}-(2R,4R)-4-(2-hydroxy-3-pyrrolidin-1-ylpropoxy)pyrrolidine-1,2-dicarboxamide, 1-N-[(4-chlorophenyl)]-2-N-{[4-(3-oxomorpholin-4-yl)phenyl]}-(2R,4R)-4-(2-oxooxazolidin-5-ylmethoxy)pyrrolidine-1,2-dicarboxamide, 1-N-[(4-chlorophenyl)]-2-N-{[4-(3-oxomorpholin-4-yl)phenyl]}-(2R,4R)-4-(3-amino-2-hydroxypropoxy)pyrrolidine-1,2-dicarboxamide, 1-N-[(4-chlorophenyl)]-2-N-{[3-fluoro-4-(3-oxomorpholin-4-yl)phenyl]}-(R)-2,5-dihydropyrrole-1,2-dicarboxamide, 1-N-[(4-chlorophenyl)]-2-N-{[2-fluoro-4-(3-oxomorpholin-4-yl)phenyl]}-(R)-2,5-dihydropyrrole-1,2-dicarboxamide, 1-N-[(4-chlorophenyl)]-2-N-{[4-(3-oxomorpholin-4-yl)phenyl]}-(2S ,3S)-3-hydroxypyrrolidine-1,2-dicarboxamide, 1-N-[(4-chlorophenyl)]-2-N-{[4-(3-oxomorpholin-4-yl)phenyl]}-(2S ,4S)-4-hydroxypyrrolidine-1,2-dicarboxamide, 1-N-[(4-chlorophenyl)]-2-N-{[2-carboxy-4-(3-oxomorpholin-4-yl)phenyl]}-(2R,4R)-3-hydroxypyrrolidine-1,2-dicarboxamide, 1-N-[(4-chlorophenyl)]-2-N-{[4-(3-oxomorpholin-4-yl)phenyl]}-(2R,3S,4R)-3,4-dihydroxypyrrolidine-1,2-dicarboxamide, 1-N-[(4-chlorophenyl)]-2-N-{[2-fluoro-4-(3-oxomorpholin-4-yl)phenyl]}-(2R,4R)-4-allyloxypyrrolidine-1,2-dicarboxamide, 1-N-[(4-chlorophenyl)]-2-N-{[2-fluoro-4-(3-oxomorpholin-4-yl)phenyl]}-(2R,4R)-4-(prop-2-ynyloxy)pyrrolidine-1,2-dicarboxamide, 1-N-[(4-chlorophenyl)]-2-N-{[2-fluoro-4-(3-oxomorpholin-4-yl)phenyl]}-(2R,4S)-4-(prop-2-ynyloxy)pyrrolidine-1,2-dicarboxamide, 1-N-[(4-chlorophenyl)]-2-N-{[4-(3-oxomorpholin-4-yl)phenyl]}-(2R,4R)-4-(methoxycarbonylmethoxy)pyrrolidine-1,2-dicarboxamide, 1-N-[(4-chlorophenyl)]-2-N-{[4-(3-oxomorpholin-4-yl)phenyl]}-(2R,4R)-4-(carboxymethoxy)pyrrolidine-1,2-dicarboxamide, 1-N-[(4-bromophenyl)]-2-N-{[2-fluoro-4-(3-oxomorpholin-4-yl)phenyl]}-(2R,4R)-4-methoxypyrrolidine-1,2-dicarboxamide, 1-N-[(4-chlorophenyl)]-2-N-{[2-fluoro-4-(3-oxomorpholin-4-yl)phenyl]}-(2R,4R)-4-(2,3-dihydroxypropoxy)pyrrolidine-1,2-dicarboxamide, 1-N-[(4-chlorophenyl)]-2-N-{N-methoxycarbonylmethyl-N'-[4-(3-oxomorpholin-4-yl)phenyl]}-(2R,4R)-4-methoxypyrrolidine-1,2-dicarboxamide, 1-N-[(4-chlorophenyl)]-2-N-{[4-(3-oxomorpholin-4-yl)cyclohexan-1-yl]}-(2R,4R)-4-hydroxypyrrolidine-1,2-dicarboxamide, 1-N-[(4-chlorophenyl)]-2-N-{[2-aminocarbonyl-4-(3-oxomorpholin-4-yl)phenyl]}-(2R,4R)-4-hydroxypyrrolidine-1,2-dicarboxamide;

1-N-[(4-chlorophenyl)]-2-N-{[4-(3-oxomorpholin-4-yl)phenyl]}-(2R,4R)-4-hydroxy-2-methylpyrrolidine-1,2-dicarboxamide, N-[4-(3-oxomorpholin-4-yl)phenyl]-(2R,4R)-1-[(E)-3-(5-chlorothiophen-2-yl)acryloyl]-4-hydroxypyrrolidine-2-carboxamide, N-[4-(3-oxomorpholin-4-yl)phenyl]-(2R,4R)-1-[(E)-3-thiophen-3-ylacryloyl]-4-hydroxypyrrolidine-2-carboxamide, N-[4-(3-oxomorpholin-4-yl)phenyl]-(2R,4R)-1-[(2E,4E)-5-phenylpenta-2,4-dienyloyl]-4-hydroxypyrrolidine-2-carboxamide, N-[4-(3-oxomorpholin-4-yl)phenyl]-(2R,4R)-1-[(E)-3-(5-methylfuran-2-yl)acryloyl]-4-hydroxypyrrolidine-2-carboxamide, N-[4-(3-oxomorpholin-4-yl)phenyl]-(2R,4R)-1-[(E)-3-thiophen-2-ylacryloyl]-4-hydroxypyrrolidine-2-carboxamide, N-[2-fluoro-4-(3-oxomorpholin-4-yl)phenyl]-(2R,4R)-1-[(E)-3-(5-chlorothiophen-2-yl)acryloyl]-4-methoxypyrrolidine-2-carboxamide, N-[2-fluoro-4-(3-oxomorpholin-4-yl)phenyl]-(2R,4R)-1-[(E)-3-(5-chlorothiophen-2-yl)acryloyl]-4-hydroxypyrrolidine-2-carboxamide, N-[4-(3-oxomorpholin-4-yl)phenyl]-(2R,4R)-1-[(E)-3-(4-chlorophenyl)acryloyl]-4-hydroxypyrrolidine-2-carboxamide, N-[4-(3-oxomorpholin-4-yl)phenyl]-(2R,4R)-1-[(E)-3-(3,4-dichlorophenyl)acryloyl]-4-hydroxypyrrolidine-2-carboxamide, N-[4-(3-oxomorpholin-4-yl)phenyl]-(2R,4R)-1-[(E)-3-(4-chlorophenyl)acryloyl]-4-methoxypyrrolidine-2-carboxamide, N-[4-(3-oxomorpholin-4-yl)phenyl]-(2R,4R)-1-[(E)-3-(3,4-dichlorophenyl)acryloyl]-4-methoxypyrrolidine-2-carboxamide, N-[4-(3-oxomorpholin-4-yl)phenyl]-(2R,4R)-1-[(E)-3-1H-imidazol-4-ylacryloyl]-4-hydroxypyrrolidine-2-carboxamide, N-[4-(3-oxomorpholin-4-yl)phenyl]-(2R,4R)-1-[(E)-3-(5-chlorothiophen-2-yl)acryloyl]-4-methoxypyrrolidine-2-carboxamide, N-[4-(3-oxomorpholin-4-yl)phenyl]-(2R,4R)-1-[(E)-3-(5-chlorofuran-2-yl)acryloyl]-4-hydroxypyrrolidine-2-carboxamide, N-[4-(3-oxomorpholin-4-yl)phenyl]-(2R,4R)-1-[(E)-3-(5-chlorofuran-2-yl)acryloyl]-4-methoxypyrrolidine-2-carboxamide, N-[4-(3-oxomorpholin-4-yl)phenyl]-(2R,4R)-1-[(E)-3-(4-chlorophenyl)acryloyl]-4-ethoxypyrrolidine-2-carboxamide, N-[4-(3-oxomorpholin-4-yl)phenyl]-(2R,4R)-1-[(E)-3-(3,4-dichlorophenyl)acryloyl]-4-ethoxypyrrolidine-2-carboxamide, N-[4-(3-oxomorpholin-4-yl)phenyl]-(2R,4R)-1-[(E)-3-(5-chlorofuran-2-yl)acryloyl]-4-ethoxypyrrolidine-2-carboxamide, N-[4-(3-oxomorpholin-4-yl)phenyl]-(2R,4R)-1-[(E)-3-(5-chlorothiophen-2-yl)acryloyl]-4-ethoxypyrrolidine-2-carboxamide, N-[2-fluoro-4-(3-oxomorpholin-4-yl)phenyl]-(2R,4R)-1-[(E)-3-(4-chloro-phenyl)acryloyl]-4-hydroxypyrrolidine-2-carboxamide, N-[2-fluoro-4-(3-oxomorpholin-4-yl)phenyl]-(2R,4R)-1-[(E)-3-(3,4-dichlorophenyl)acryloyl]-4-hydroxypyrrolidine-2-carboxamide, N-[2-fluoro-4-(3-oxomorpholin-4-yl)phenyl]-(2R,4R)-1-[(E)-3-(5-chlorofuran-2-yl)acryloyl]-4-hydroxypyrrolidine-2-carboxamide, N-[2-fluoro-4-(3-oxomorpholin-4-yl)phenyl]-(2R,4R)-1-[(E)-3-(5-chlorofuran-2-yl)acryloyl]-4-methoxypyrrolidine-2-carboxamide, N-[2-fluoro-4-(3-oxomorpholin-4-yl)phenyl]-(2R,4R)-1-[(E)-3-(4-chlorophenyl)acryloyl]-4-methoxypyrrolidine-2-carboxamide, N-[2-fluoro-4-(3-oxomorpholin-4-yl)phenyl]-(2R,4R)-1-[(E)-3-(3,4-dichlorophenyl)acryloyl]-4-methoxypyrrolidine-2-carboxamide, N-[2-fluoro-4-(3-oxomorpholin-4-yl)phenyl]-(2R,4R)-1-[(E)-3-(4-chlorophenyl)acryloyl]-4-ethoxypyrrolidine-2-carboxamide, N-[2-fluoro-4-(3-oxomorpholin-4-yl)phenyl]-(2R,4R)-1-[(E)-3-(3,4-dichlorophenyl)acryloyl]-4-ethoxypyrrolidine-2-carboxamide, N-[2-fluoro-4-(3-oxomorpholin-4-yl)phenyl]-(2R,4R)-1-[(E)-3-(5-chlorofuran-2-yl)acryloyl]-4-ethoxypyrrolidine-2-carboxamide, N-[2-fluoro-4-(3-oxomorpholin-4-yl)phenyl]-(2R,4R)-1-[(E)-3-(5-chlorothiophen-2-yl)acryloyl]-4-ethoxypyrrolidine-2-carboxamide, N-[4-(3-oxomorpholin-4-yl)phenyl]-(2R,4R)-1-[(E)-3-1H-imidazol-4-ylacryloyl]-4-ethoxypyrrolidine-2-carboxamide, N-[2-fluoro-4-(3-oxomorpholin-4-yl)phenyl]-(2R,4R)-1-[(E)-3-1H-imidazol-4-ylacryloyl]-4-hydroxypyrrolidine-2-carboxamide, N-[2-fluoro-4-(3-oxomorpholin-4-yl)phenyl]-(2R,4R)-1-[(E)-3-1H-imidazol-4-ylacryloyl]-4-methoxypyrrolidine-2-carboxamide, N-[2-fluoro-4-(3-oxomorpholin-4-yl)phenyl]-(2R,4R)-1-[(E)-3-1H-imidazol-4-ylacryloyl]-4-ethoxypyrrolidine-2-carboxamide, N-[2-fluoro-4-(3-oxomorpholin-4-yl)phenyl]-(2R,4R)-1-[(E)-3-pyridin-3-ylacryloyl]-4-hydroxypyrrolidine-2-carboxamide, N-[4-(3-oxomorpholin-4-yl)phenyl]-(2R,4R)-1-[(E)-3-pyridin-3-ylacryloyl]-4-ethoxypyrrolidine-2-carboxamide, N-[2-fluoro-4-(3-oxomorpholin-4-yl)phenyl]-(2R,4R)-1-[(E)-3-pyridin-3-ylacryloyl]-4-methoxypyrrolidine-2-carboxamide, N-[2-fluoro-4-(3-oxomorpholin-4-yl)phenyl]-(2R,4R)-1-[(E)-3-pyridin-3-ylacryloyl]-4-ethoxypyrrolidine-2-carboxamide, N-[4-(3-oxomorpholin-4-yl)phenyl]-(2R,4R)-1-[(E)-3-pyridin-3-ylacryloyl]-4-hydroxypyrrolidine-2-carboxamide, N-[4-(3-oxomorpholin-4-yl)phenyl]-(2R,4R)-1-[(E)-3-pyridin-3-ylacryloyl]-4-methoxypyrrolidine-2-carboxamide, N-[4-(3-oxomorpholin-4-yl)phenyl]-(2R,4R)-1-[(E)-3-pyridin-4-ylacryloyl]-4-hydroxypyrrolidine-2-carboxamide, N-[4-(3-oxomorpholin-4-yl)phenyl]-(2R,4R)-1-[(E)-3-pyridin-4-ylacryloyl]-4-ethoxypyrrolidine-2-carboxamide, N-[4-(3-oxomorpholin-4-yl)phenyl]-(2R,4R)-1-[(E)-3-1H-imidazol-4-ylacryloyl]-4-methoxypyrrolidine-2-carboxamide, N-[4-(3-oxomorpholin-4-yl)phenyl]-(2R,4R)-1-[(E)-3-(4-bromothiophen-2-yl)acryloyl]-4-hydroxypyrrolidine-2-carboxamide, N-[4-(3-oxomorpholin-4-yl)phenyl]-(2R,4R)-1-[(E)-3-(4-bromothiophen-2-yl)acryloyl]-4-ethoxypyrrolidine-2-carboxamide, N-[4-(3-oxomorpholin-4-yl)phenyl]-(2R,4R)-1-[(E)-3-(5-bromothiophen-2-yl)acryloyl]-4-hydroxypyrrolidine-2-carboxamide, N-[4-(3-oxomorpholin-4-yl)phenyl]-(2R,4R)-1-[(E)-3-(5-bromothiophen-2-yl)acryloyl]-4-ethoxypyrrolidine-2-carboxamide, 1-N-[4-chlorophenyl)]-2-N-{[4-((S)-2-methyl-3-oxomorpholin-4-yl)phenyl]}-(2R,4R)-4-hydroxypyrrolidine-1,2-dicarboxamide,
1-N-[(4-chlorophenyl)]-2-N-{[4-((S)-2-methyl-3-oxomorpholin-4-yl)phenyl]}-(2R)-pyrrolidine-1,2-dicarboxamide,
1-N-[(4-chlorophenyl)]-2-N-{[4-((R)-2-methyl-3-oxomorpholin-4-yl)phenyl]}-(2R,4R)-4-hydroxypyrrolidine-1,2-dicarboxamide,
1-N-[(4-chlorophenyl)]-2-N-{[4-((R)-2-methyl-3-oxomorpholin-4-yl)phenyl]}-(2R)-pyrrolidine-1,2-dicarboxamide,
1-N-[(4-chlorophenyl)]-2-N-{[4-(3-oxomorpholin-4-yl)-2-phenoxyphenyl]}-(2R)-pyrrolidine-1,2-dicarboxamide,
1-N-[(4-chlorophenyl)]-2-N-{[2-fluoro-4-((R)-2-methyl-3-oxomorpholin-4-yl)-phenyl]}-(2R,4R)-4-hydroxypyrrolidine-1,2-dicarboxamide,
1-N-[(4-chlorophenyl)]-3-N-{[4-(3oxomorpholin-4-yl)phenyl]}piperidine-1,3-dicarboxamide,
1-N-[(4-chlorophenyl)]-3-N-[{3-methyl-4-(3-oxomorpholin-4-yl)phenyl]}piperidine-1,3-dicarboxamide,
1-N-[(4-chlorophenyl)]-2-N-{[4-(3-oxomorpholin-4-yl)phenyl]}-(2R,4R)-4-(2-methoxyethoxy)pyrrolidine-1,2-dicarboxamide,
1-N-[(4-chlorophenyl)]-2-N-{[2-methyl-4-(3-oxomorpholin-4-yl)phenyl]}-(2R,4R)-4-hydroxypyrrolidine-1,2-dicarboxamide,
1-N-[(4-chlorophenyl)]-2-N-{[4-(3-oxomorpholin-4-yl)phenyl]}-(2R,4R)-4-hydroxypyrrolidine-1,2-dicarboxamide,
1-N-[(4-chlorophenyl)]-2-N-{[2-(3-oxomorpholin-4-yl)phenyl]}-(2R,4R)-4-hydroxypyrrolidine-1,2-dicarboxamide,
or a pharmaceutically usable salt or stereoisomer thereof, including mixtures thereof in all ratios.

4. The method according to claim 1, wherein said compound is selected from:
N-[4-(3-oxomorpholin-4-yl)phenyl]-(rac)-2-[3-(4-chlorophenyl)-ureido]cyclopentanecarboxamide,
N-[3-methyl-4-(3-oxomorpholin-4-yl)phenyl]-(rac)-2-[3-(4-chloro-phenyl)ureido]cyclopentanecarboxamide,
or a pharmaceutically usable salt or stereoisomer thereof, including mixtures thereof in all ratios.

5. The method according to claim 1, wherein said compound inhibits coagulation factor IXa.

6. The method according to claim 1, wherein said compound inhibits coagulation factor VIIa.

7. A method according to claim 1, further comprising administering to said patient at least one further medicament active ingredient.

8. A method according to claim 7, wherein 1-N-[(4-chlorophenyl)-2-N-{[4-(3-oxomorpholin-4-yl)phenyl]}-(2R,4R)-4-hydroxypyrrolidine-1,2-dicarboxamide and/or a pharmaceutically usable salt or stereoisomer thereof, including mixtures thereof in all ratios, and aspirin are administered to said patient.

9. The method according to claim 1, wherein

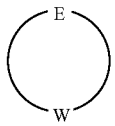

is pyrrolidine-1,2-diyl,
G is —NH—,
X is CONH, and
Ar is phenyl which is substituted or unsubstituted.

10. The method according to claim 1, wherein $R^1$ is H, =O, COOA, OH, OA, $NH_2$, alkyl having 1, 2, 3, 4, 5 or 6 carbon atoms, $N_3$, ethynyl, vinyl, allyloxy, methylcarbonyloxy, acetamino, or methylsulfonylamino.

11. The method according to claim 1, wherein $R^2$ is H, =O, OH, methoxy, or alkyl having 1, 2, 3, 4, 5 or 6 carbon atoms.

12. The method according to claim 1, wherein $R^3$ is H.

13. The method according to claim 1, wherein

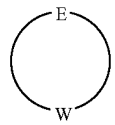

is pyrrolidine-1,2-diyl.

14. The method according to claim 1, wherein

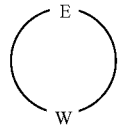

is piperidine-1,2-diyl.

15. The method according to claim 1, wherein

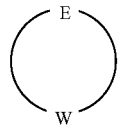

is oxazolidine-3,4- or 3,5-diyl.

16. The method according to claim 1, wherein

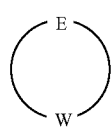

is thiazolidine-3,4-diyl.

17. The method according to claim 1, wherein

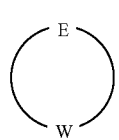

is 2,5-dihydro-1H-pyrrole-1,5-diyl.

18. The method according to claim 1, wherein

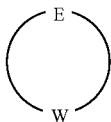

is 1,3-dioxolane-4,5-diyl.

19. The method according to claim 1, wherein

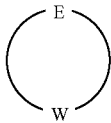

is 1,3-oxazinane-3,4-diyl.

20. The method according to claim 1, wherein

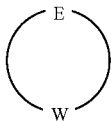

is piperazine-1,4-diyl.

21. The method according to claim 1, wherein

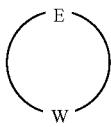

is tetrahydrofuran-3,4-diyl.

22. The method according to claim 1, wherein

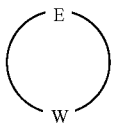

is azetidine-1,2-diyl.

23. The method according to claim 1, wherein D is phenyl which is monosubstituted or disubstituted by Hal.

24. The method according to claim 1, wherein D is pyridyl which is monosubstituted or disubstituted by Hal.

25. The method according to claim 1, wherein D is thienyl which is monosubstituted or disubstituted by Hal.

26. The method according to claim 1, wherein G is —(CH$_2$)$_n$—.

27. The method according to claim 1, wherein G is —(CH$_2$)$_n$NH—.

28. The method according to claim 1, wherein said compound is selected from:
1-N-[(4-chlorophenyl)]-2-N-{[4-(3-oxomorpholin-4-yl)phenyl]}-(R)-pyrrolidine-1,2-dicarboxamide,
1-N-[(4-chlorophenyl)]-2-N-{[3-methyl-4-(3-oxomorpholin-4-yl)phenyl]}-(R)-pyrrolidine-1,2-dicarboxamide,
1-N-[(4-chlorophenyl)]-2-N-{[3-fluoro-4-(3-oxomorpholin-4-yl)phenyl]}-(R)-pyrrolidine-1,2-dicarboxamide,
1-N-[(4-chlorophenyl)]-2-N-{[2-fluoro-4-(3-oxomorpholin-4-yl)phenyl]}-(R)-pyrrolidine-1,2-dicarboxamide,
1-N-[(4-chlorophenyl)]-2-N-{[3-trifluoromethyl-4-(3-oxomorpholin-4-yl)phenyl]}-(R)-pyrrolidine-1,2-dicarboxamide,
N-[4-(3-oxomorpholin-4-yl)phenyl]-(R)-1-(5-chlorothiophene-2-carbonyl)pyrrolidine-2-carboxamide,
N-[3-methyl-4-(3-oxomorpholin-4-yl)phenyl]-(R)-1-(5-chlorothiophene-2-carbonyl)pyrrolidine-2-carboxamide,
or a pharmaceutically usable salt or stereoisomer thereof, including mixtures thereof in all ratios.

29. The method according to claim 1, wherein said compound is selected from:
1-N-[(4-chlorophenyl)]-2-N-{[3-methyl-4-(3-oxomorpholin-4-yl)phenyl]}-(R)-piperidine-1,2-dicarboxamide,
1-N-[(4-chlorophenyl)]-2-N-{[4-(3-oxomorpholin-4-yl)phenyl]}-(R)-2,5-dihydropyrrole-1,2-dicarboxamide,
3-N-[(4-chlorophenyl)]-4-N-{[4-(3-oxomorpholin-4-yl)phenyl]}-(R)-oxazolidine-3,4-dicarboxamide,
3-N-[(4-chlorophenyl)]-4-N-{[3-methyl-4-(3-oxomorpholin-4-yl)phenyl]}-(R)-oxazolidine-3,4-dicarboxamide,
3-N-[(4-chlorophenyl)]-4-N-{[4-(3-oxomorpholin-4-yl)phenyl]}-(4R,5S)-5-methyloxazolidine-3,4-dicarboxamide,
3-N-[(4-chlorophenyl)-4-N-{[3-methyl-4-(3-oxomorpholin-4-yl)phenyl]}-(4R,5S)-5-methyloxazolidine-3,4-dicarboxamide,
3-N-[(4-chlorophenyl)]-4-N-{[3-fluoro-4-(3-oxomorpholin-4-yl)phenyl]}-(4R,5S)-5-methyloxazolidine-3,4-dicarboxamide,
3-N-[(4-chlorophenyl)]-4-N-{[3-chloro-4-(3-oxomorpholin-4-yl)phenyl]}-(4R,5S)-5-methyloxazolidine-3,4-dicarboxamide,
3-N-[(4-chlorophenyl)]-4-N-{[3-methyl-4-(3-oxomorpholin-4-yl)phenyl]}-(4R,5R)-5-methyloxazolidine-3,4-dicarboxamide,
N-[4-(3-oxomorpholin-4-yl)phenyl]-3-(5-chlorothiophene-2-carbonyl)oxazolidine-5-carboxamide,
N-[3-methyl-4-(3-oxomorpholin-4-yl)phenyl]-3-(5-chlorothiophene-2-carbonyl)oxazolidine-5-carboxamide,
or a pharmaceutically usable salt or stereoisomer thereof, including mixtures thereof in all ratios.

30. The method according to claim 1, wherein said compound is selected from:
3-N-[(4-chlorophenyl)]-4-N-{[4-(3-oxomorpholin-4-yl)phenyl]}-(S)-thiazolidine-3,4-dicarboxamide,
3-N-[(4-chlorophenyl)]-4-N-{[4-(3-oxomorpholin-4-yl)phenyl]}-(S)-1,1-dioxo-1$\lambda^6$-thiazolidine-3,4-dicarboxamide,
3-N-[(4-chlorophenyl)]-4-N-{[3-methyl-4-(3-oxomorpholin-4-yl)phenyl]}-(S)-thiazolidine-3,4-dicarboxamide,
3-N-[(4-chlorophenyl)]-4-N-{[3-methyl-4-(3-oxomorpholin-4-yl)phenyl]}-(S)-1,1-dioxo-1$\lambda^6$-thiazolidine-3,4-dicarboxamide,
or a pharmaceutically usable salt or stereoisomer thereof, including mixtures thereof in all ratios.

31. The method according to claim 1, wherein said compound is selected from:
- 1-N-[(5-chloropyridin-2-yl)]-2-N-{[4-(3-oxomorpholin-4-yl)phenyl]}-(2R,4R)-4-hydroxypyrrolidine-1,2-dicarboxamide,
- 1-N-[(5-chloropyridin-2-yl)]-2-N-{[4-(3-oxomorpholin-4-yl)phenyl]}-(R)-4,4-dimethoxypyrrolidine-1,2-dicarboxamide,
- 1-N-[(4-chlorophenyl)]-2-N-{[4-(3-oxomorpholin-4-yl)phenyl]}-(2R,4R)-4-hydroxypyrrolidine-1,2-dicarboxamide,
- 1-N-[(4-chlorophenyl)]-2-N-{[3-methyl-4-(3-oxomorpholin-4-yl)phenyl]}-(2R,4R)-4-hydroxypyrrolidine-1,2-dicarboxamide,
- 1-N-[(4-chlorophenyl)]-2-N-{[2-fluoro-4-(3-oxomorpholin-4-yl)phenyl]}-(2R,4R)-4-hydroxypyrrolidine-1,2-dicarboxamide,
- 1-N-[(4-chlorophenyl)]-2-N-{[3-fluoro-4-(3-oxomorpholin-4-yl)phenyl]}-(2R,3R)-3-hydroxypyrrolidine-1,2-dicarboxamide,
- 1-N-[(4-chlorophenyl)]-2-N-{[3-fluoro-4-(3-oxomorpholin-4-yl)phenyl]}-(2R,3S)-3-hydroxypyrrolidine-1,2-dicarboxamide,
- 1-N-[(4-chlorophenyl)]-2-N-{[4-(3-oxomorpholin-4-yl)phenyl]}-(2R,4S)-4-hydroxypyrrolidine-1,2-dicarboxamide,
- 1-N-[(4-chlorophenyl)]-2-N-{[4-(3-oxomorpholin-4-yl)phenyl]}-(2S,4R)-4-hydroxypyrrolidine-1,2-dicarboxamide,
- 1-N-[(4-chlorophenyl)]-2-N-{[4-(3-oxomorpholin-4-yl)phenyl]}-3,4-dihydroxypyrrolidine-1,2-dicarboxamide, or a pharmaceutically usable salt or stereoisomer thereof, including mixtures thereof in all ratios.

32. The method according to claim 1, wherein said compound is selected from:
- 1-N-[(4-chlorophenyl)]-2-N-{[4-(3-oxomorpholin-4-yl)phenyl]}-(2R,4S)-4-azidopyrrolidine-1,2-dicarboxamide,
- 1-N-[(4-chlorophenyl)]-2-N-{[4-(3-oxomorpholin-4-yl)phenyl]}-(2R,4S)-4-aminopyrrolidine-1,2-dicarboxamide,
- 1-N-[(4-chlorophenyl)]-2-N-{[4-(3-oxomorpholin-4-yl)phenyl]}-(2R,4R)-4-azidopyrrolidine-1,2-dicarboxamide,
- 1-N-[(4-chlorophenyl)]-2-N-{[4-(3-oxomorpholin-4-yl)phenyl]}-(2R,4R)-4-aminopyrrolidine-1,2-dicarboxamide,
- 1-N-[(4-chlorophenyl)]-2-N-{[4-(3-oxomorpholin-4-yl)phenyl]}-(2R,4S)-4-acetaminopyrrolidine-1,2-dicarboxamide,
- 1-N-[(4-chlorophenyl)]-2-N-{[4-(3-oxomorpholin-4-yl)phenyl]}-(2R,4R)-4-acetaminopyrrolidine-1,2-dicarboxamide,
- 1-N-[(4-chlorophenyl)]-2-N-{[4-(3-oxomorpholin-4-yl)phenyl]}-(2R,4S)-4-methylsulfonylaminopyrrolidine-1,2-dicarboxamide,
- 1-N-[(4-chlorophenyl)]-2-N-{[4-(3-oxomorpholin-4-yl)phenyl]}-(2R,4R)-4-methylsulfonylaminopyrrolidine-1,2-dicarboxamide,
- 1-N-[(4-chlorophenyl)]-2-N-{[4-(3-oxomorpholin-4-yl)phenyl]}-(2R,4R)-4-methoxypyrrolidine-1,2-dicarboxamide,
- 1-N-[(4-chlorophenyl)]-2-N-{[4-(3-oxomorpholin-4-yl)phenyl]}-(2R,4R)-4-ethoxypyrrolidine-1,2-dicarboxamide,
- 1-N-[(4-chlorophenyl)]-2-N-{[4-(3-oxomorpholin-4-yl)phenyl]}-(2R,4R)-4-propoxypyrrolidine-1,2-dicarboxamide,
- 1-N-[(4-chlorophenyl)]-2-N-{[4-(3-oxomorpholin-4-yl)phenyl]}-(2R,4R)-4-allyloxypyrrolidine-1,2-dicarboxamide,
- (3R,5R)-1-(4-chlorophenylcarbamoyl)-5-[4-(3-oxomorpholin-4-yl)-phenylcarbamoyl]pyrrolidin-3-yl isobutyrate,
- (3R,5R)-1-(4-chlorophenylcarbamoyl)-5-[4-(3-oxomorpholin-4-yl)-phenylcarbamoyl]pyrrolidin-3-yl propionate,
- (3R,5R)-1-(4-chlorophenylcarbamoyl)-5-[4-(3-oxomorpholin-4-yl)-phenylcarbamoyl]pyrrolidin-3-yl acetate, or a pharmaceutically usable salt or stereoisomer thereof, including mixtures thereof in all ratios.

33. The method according to claim 1, wherein said compound is selected from:
- 4-N-[(4-chlorophenyl)]-5-N-{[4-(3-oxomorpholin-4-yl)phenyl]}-1,3-dioxolane-4,5-dicarboxamide,
- 4-N-[(4-chlorophenyl)]-5-N-{[3-methyl-4-(3-oxomorpholin-4-yl)phenyl]{-1,3-dioxolane-4,5-dicarboxamide,
- 4-N-[(4-chlorophenyl)]-5-N-{[4-(3-oxomorpholin-4-yl)phenyl]}-1,3-dioxolane-2,2-dimethyl-4,5-dicarboxamide,
- 4-N-[(4-chlorophenyl)]-5-N-{[3-methyl-4-(3-oxomorpholin-4-yl)phenyl]{-1,3-dioxolane-2,2-dimethyl-4,5-dicarboxamide,
- 1-N-[4-chlorophenyl)]-2-N-{[4-(3-oxomorpholin-4-yl)phenyl]}-1-BOC-piperazine-1,2-dicarboxamide,
- 1-N-[4-chlorophenyl)]-2-N-{[4-(3-oxomorpholin-4-yl)phenyl]}piperazine-1,2-dicarboxamide,
- 1-N-[4-chlorophenyl)]-2-N-{[4-(3-oxomorpholin-4-yl)phenyl]}-1,3-oxazinane-3,4-dicarboxamide,
- 1-N-[(4-chlorophenyl)]-2-N-{[4-(3-oxomorpholin-4-yl)phenyl]}-(2R,4S)-4-ethynyl-4-hydroxypyrrolidine-1,2-dicarboxamide,
- 6-N-[(4-chlorophenyl)]-7-N-{[4-(3-oxomorpholin-4-yl)phenyl]}-4-oxa-6-azaspiro[2,4]heptane-6,7-dicarboxamide,
- 1-N-[(4-chlorophenyl)]-2-N-[{3-methyl-4-(3-oxomorpholin-4-yl)phenyl]}-(2R,4S)-4-acetaminopyrrolidine-1,2-dicarboxamide,
- 1-N-[(4-chlorophenyl)]-2-N-{[4-(3-oxomorpholin-4-yl)phenyl]}-(2R,4S)-4-butylsulfonylaminopyrrolidine-1,2-dicarboxamide,
- 1-N-[(4-chlorophenyl)]-2-N-{[4-(3-oxomorpholin-4-yl)phenyl]}-(R)-4-oxopyrrolidine-1,2-dicarboxamide,
- 1-N-[(4-chlorophenyl)]-2-N-[{3-methyl-4-(3-oxomorpholin-4-yl)phenyl]}-(2R,4S)-4-aminopyrrolidine-1,2-dicarboxamide,
- 1-N-[(4-chlorophenyl)]-2-N-[{3-methyl-4-(3-oxomorpholin-4-yl)phenyl]}-(S)-pyrrolidine-1,2-dicarboxamide, or a pharmaceutically usable salt or stereoisomer thereof, including mixtures thereof in all ratios.

34. The method according to claim 1, wherein said compound is selected from:
- 1-N-[(4-chlorophenyl)]-2-N-{[2-fluoro-4-(3-oxomorpholin-4-yl)phenyl]}-(2R,4R)-4-hydroxypyrrolidine-1,2-dicarboxamide,
- N-[4-(3-oxomorpholin-4-yl)phenyl]-(2R,4R)-1-[2-(4-chlorophenyl)acetyl]-4-hydroxypyrrolidine-2-carboxamide,
- N-[4-(3-oxomorpholin-4-yl)phenyl]-(2R,4R)-1-(4-chlorobenzoyl)-4-hydroxypyrrolidine-2-carboxamide, 1-N-[(4-chlorophenyl)]-2-N-[{3-methyl-4-(3-oxomorpholin-4-yl)phenyl]}-(2R,4R)-4-methoxypyrrolidine-1,2-dicarboxamide, 1-N-[(4-chlorophenyl)]-2-N-{[4-(3-oxomorpholin-4-yl)phenyl]}-(2R,4S)-4-(2-methylpropanoylamino)pyrrolidine-1,2-dicarboxamide, N-[4-(3-oxomorpholin-4-yl)phenyl]-(2R,4R)-1-(1-1H-indol-3-ylmethanoyl)-4-hydroxypyrrolidine-2-carboxamide, N-[4-(3-oxomorpholin-4-yl)phenyl]-(2R,4R)-1-(1-1H-indol-6-ylmethanoyl)-4-hydroxypyrrolidine-2-carboxamide, 1-N-[(4-chlorophenyl)]-2-N-[{3-methyl-4-(3-oxomorpholin-4-yl)phenyl]}-(2R,4S)-4-ethoxypyrrolidine-1,2-dicarboxamide, 1-N-[(4-chlorophenyl)]-2-N-{[2-fluoro-4-(3-oxomorpholin-4-yl)phenyl]}-(2R,4R)-4-ethoxypyrrolidine-1,2-dicarboxamide, 2-N-[(4-chlorophenyl)]-1-N-{[4-(3oxomorpholin-4-yl)phenyl]}-(R)-pyrrolidine-1,2-dicarboxamide, 2-N-[(4-chlorophenyl)]-1-N-{[4-(3oxomorpholin-4-yl)phenyl]}-(S)-pyrrolidine-1,2-dicarboxamide, or a pharmaceutically usable salt or stereoisomer thereof, including mixtures thereof in all ratios.

35. The method according to claim 1, wherein said compound is selected from:

N-(4-chlorophenyl)-(R)-1-{2-[4-(3-oxomorpholin-4-yl)phenyl]acetyl}pyrrolidine-2-carboxamide, N-(4-chlorophenyl)-(S)-1-{2-[4-(3-oxomorpholin-4-yl)phenyl]acetyl}pyrrolidine-2-carboxamide, N-(4-chlorophenyl)-(2R,4R)-1-{2-[4-(3-oxomorpholin-4-yl)phenyl]acetyl}-4-methoxypyrrolidine-2-carboxamide, N-(4-chlorophenyl)-(2R,4S)-1-{2-[4-(3-oxomorpholin-4-yl)phenyl]acetyl}-4-methoxypyrrolidine-2-carboxamide, N-(4-chlorophenyl)-(2S,4R)-1-{2-[4-(3-oxomorpholin-4-yl)phenyl]acetyl}-4-methoxypyrrolidine-2-carboxamide, 1-N-[(4-chlorophenyl)]-2-N-{]3-fluoro-4-(3-oxomorpholin-4-yl)phenyl]}-(2R,4R)-4-ethoxypyrrolidine-1,2-dicarboxamide, 1-N-[(4-chlorophenyl)]-2-N-{[4-(3-oxomorpholin-4-yl)phenyl]}-(2R,4R)-4-(prop-2-ynyloxy)pyrrolidine-1,2-dicarboxamide, 1-N-[(4-chlorophenyl)]-2-N-{[4-(3-oxomorpholin-4-yl)phenyl]}-(2R,4R)-4-(but-2-ynyloxy)pyrrolidine-1,2-dicarboxamide, 1-N-[(4-chlorophenyl)]-2-N-{[4-(3-oxomorpholin-4-yl)phenyl]}-(2R,4R)-4-(2,3-dihydroxypropoxy)pyrrolidine-1,2-dicarboxamide, 1-N-[(4-chlorophenyl)]-2-N-{[4-(3-oxomorpholin-4-yl)phenyl]}-(2R,4R)-4-(2-hydroxy-3-pyrrolidin-1-ylpropoxy)pyrrolidine-1,2-dicarboxamide, or a pharmaceutically usable salt or stereoisomer thereof, including mixtures thereof in all ratios.

36. The method according to claim 1, wherein said compound is selected from:

1-N-[(4-chlorophenyl)]-2-N-{[4-(3-oxomorpholin-4-yl)phenyl]}-(2R,4R)-4-(2-oxooxazolidin-5-ylmethoxy)pyrrolidine-1,2-dicarboxamide, 1-N-[(4-chlorophenyl)]-2-N-{[4-(3-oxomorpholin-4-yl)phenyl]}-(2R,4R)-4-(3-amino-2-hydroxypropoxy)pyrrolidine-1,2-dicarboxamide, 1-N-[(4-chlorophenyl)]-2-N-{[3-fluoro-4-(3-oxomorpholin-4-yl)phenyl]}-(R)-2,5-dihydropyrrole-1,2-dicarboxamide, 1-N-[(4-chlorophenyl)]-2-N-{[2-fluoro-4-(3-oxomorpholin-4-yl)phenyl]}-(R)-2,5-dihydropyrrole-1,2-dicarboxamide, 1-N-[(4-chlorophenyl)]-2-N-{[4-(3-oxomorpholin-4-yl)phenyl]}-(2S,3S)-3-hydroxypyrrolidine-1,2-dicarboxamide, 1-N-[(4-chlorophenyl)]-2-N-{[4-(3-oxomorpholin-4-yl)phenyl]}-(2S,4S)-4-hydroxypyrrolidine-1,2-dicarboxamide, 1-N-[(4-chlorophenyl)]-2-N-{[2-carboxy-4-(3-oxomorpholin-4-yl)phenyl]}-(2R,4R)-3-hydroxypyrrolidine-1,2-dicarboxamide, 1-N-[(4-chlorophenyl)]-2-N-{[4-(3oxomorpholin-4-yl)phenyl]}-(2R,3S,4R)-3,4-dihydroxypyrrolidine-1,2-dicarboxamide, 1-N-[(4-chlorophenyl)]-2-N-{[2-fluoro-4-(3-oxomorpholin-4-yl)phenyl]}-(2R,4R)-4-allyloxypyrrolidine-1,2-dicarboxamide, 1-N-[(4-chlorophenyl)]-2-N-{[2-fluoro-4-(3-oxomorpholin-4-yl)phenyl]}-(2R,4R)-4-(prop-2-ynyloxy)pyrrolidine-1,2-dicarboxamide, or a pharmaceutically usable salt or stereoisomer thereof, including mixtures thereof in all ratios.

37. The method according to claim 1, wherein said compound is selected from:

1-N-[(4-chlorophenyl)]-2-N-{[2-fluoro-4-(3-oxomorpholin-4-yl)phenyl]}-(2R,4S)-4-(prop-2-ynyloxy)pyrrolidine-1,2-dicarboxamide, 1-N-[(4-chlorophenyl)]-2-N-{[4-(3-oxomorpholin-4-yl)phenyl]}-(2R,4R)-4-(methoxycarbonylmethoxy)pyrrolidine-1,2-dicarboxamide, 1-N-[(4-chlorophenyl)]-2-N-{[4-(3-oxomorpholin-4-yl)phenyl]}-(2R,4R)-4-(carboxymethoxy)pyrrolidine-1,2-dicarboxamide, 1-N-[(4-bromophenyl)]-2-N-{[2-fluoro-4-(3-oxomorpholin-4-yl)phenyl]}-(2R,4R)-4-methoxypyrrolidine-1,2-dicarboxamide, 1-N-[(4-chlorophenyl)]-2-N-{[2-fluoro-4-(3-oxomorpholin-4-yl)phenyl]}-(2R,4R)-4-(2,3-dihydroxypropoxy)pyrrolidine-1,2-dicarboxamide, 1-N-[(4-chlorophenyl)]-2-N-{N-methoxycarbonylmethyl-N'-[4-(3-oxomorpholin-4-yl)phenyl]}-(2R,4R)-4-methoxypyrrolidine-1,2-dicarboxamide, 1-N-[(4-chlorophenyl)]-2-N-{[4-(3-oxomorpholin-4-yl)cyclohexan-1-yl]}-(2R,4R)-4-hydroxypyrrolidine-1,2-dicarboxamide, 1-N-[(4-chlorophenyl)]-2-N-{[2-aminocarbonyl-4-(3-oxomorpholin-4-yl)phenyl]}-(2R,4R)-4-hydroxypyrrolidine-1,2-dicarboxamide;

1-N-[(4-chlorophenyl)]-2-N-{[4-(3-oxomorpholin-4-yl)phenyl]}-(2R,4R)-4-hydroxy-2-methylpyrrolidine-1,2-dicarboxamide, N-[4-(3-oxomorpholin-4-yl)phenyl]-(2R,4R)-1-[(E)-3-(5-chlorothiophen-2-yl)aryloyl]-4-hydroxypyrrolidine-2-carboxamide, or a pharmaceutically usable salt or stereoisomer thereof, including mixtures thereof in all ratios.

38. The method according to claim 1, wherein said compound is selected from:

N-[4-(3-oxomorpholin-4-yl)phenyl]-(2R,4R)-1-[(E)-3-thiophen-3-ylacryloyl]-4-hydroxypyrrolidine-2-carboxamide, N-[4-(3-oxomorpholin-4-yl)phenyl]-(2R,4R)-1-[(2E,4E)-5-phenylpenta-2,4-dienyloyl]-4-hydroxypyrrolidine-2-carboxamide, N-[4-(3-oxomorpholin-4-yl)phenyl]-(2R,4R)-1-[(E)-3-(5-methylfuran-2-yl)aryloyl]-4-hydroxypyrrolidine-2-carboxamide, N-[4-(3-oxomorpholin-4-yl)phenyl]-(2R,4R)-1-[(E)-3-thiophen-2-ylacryloyl]-4-hydroxypyrrolidine-2-carboxamide, N-[2-fluoro-4-(3-oxomorpholin-4-yl)phenyl]-(2R,4R)-1-[(E)-3-(5-chlorothiophen-2-yl)aryloyl]-4-methoxypyrrolidine-2-carboxamide, N-[2-fluoro-4-(3-oxomorpholin-4-yl)phenyl]-(2R,4R)-1-[(E)-3-(5-chlorothiophen-2-yl)aryloyl]-4-hydroxypyrrolidine-2-carboxamide, N-[4-(3-oxomorpholin-4-yl)phenyl]-(2R,4R)-1-[(E)-3-(4-chlorophenyl)acryloyl]-4-hydroxypyrrolidine-2-carboxamide, N-[4-(3-oxomorpholin-4-yl)phenyl]-(2R,4R)-1-[(E)-3-(3,4-dichlorophenyl)acryloyl]-4-hydroxypyrrolidine-2-carboxamide, N-[4-(3-oxomorpholin-4-yl)phenyl]-(2R,4R)-1-[(E)-3-(4-chlorophenyl)acryloyl]-4-methoxypyrrolidine-2-carboxamide, or a pharmaceutically usable salt or stereoisomer thereof, including mixtures thereof in all ratios.

39. The method according to claim 1, wherein said compound is selected from:

N-[4-(3-oxomorpholin-4-yl)phenyl]-(2R,4R)-1-[(E)-3-(3,4-dichlorophenyl)acryloyl]-4-methoxypyrrolidine-2-carboxamide, N-[4-(3-oxomorpholin-4-yl)phenyl]-(2R,4R)-1-[(E)-3-1H-imidazol-4-ylacryloyl]-4-hydroxypyrrolidine-2-carboxamide, N-[4-(3-oxomorpholin-4-yl)phenyl]-(2R,4R)-1-[(E)-3-(5-chlorothiophen-2-yl)acryloyl]-4-methoxypyrrolidine-2-carboxamide, N-[4-(3-oxomorpholin-4-yl)phenyl]-(2R,4R)-1-[(E)-3-(5-chlorofuran-2-yl)acryloyl]-4-hydroxypyrrolidine-2-carboxamide, N-[4-(3-oxomorpholin-4-yl)phenyl]-(2R,4R)-1-[(E)-3-(5-chlorofuran-2-yl)acryloyl]-4-methoxypyrrolidine-2-carboxamide, N-[4-(3-oxomorpholin-4-yl)phenyl]-(2R,4R)-1-[(E)-3-(4-chlorophenyl)acryloyl]-4-ethoxypyrrolidine-2-carboxamide, N-[4-(3-oxomorpholin-4-yl)phenyl]-(2R,4R)-1-[(E)-3-(3,4-dichlorophenyl)acryloyl]-4-ethoxypyrrolidine-2-carboxamide, N-[4-(3-oxomorpholin-4-yl)phenyl]-(2R,4R)-1-[(E)-3-(5-chlorofuran-2-yl)acryloyl]-4-ethoxypyrrolidine-2-carboxamide, N-[4-(3-oxomorpholin-4-yl)phenyl]-(2R,4R)-1-[(E)-3-(5-chlorothiophen-2-yl)acryloyl]-4-ethoxypyrrolidine-2-carboxamide, or a pharmaceutically usable salt or stereoisomer thereof, including mixtures thereof in all ratios.

40. The method according to claim 1, wherein said compound is selected from:

N-[2-fluoro-4-(3-oxomorpholin-4-yl)phenyl]-(2R,4R)-1-[(E)-3-(4-chloro-phenyl)acryloyl]-4-hydroxypyrrolidine-2-carboxamide, N-[2-fluoro-4-(3-oxomorpholin-4-yl)phenyl]-(2R,4R)-1-[(E)-3-(3,4-dichlorophenyl)acryloyl]-4-hydroxypyrrolidine-2-carboxamide, N-[2-fluoro-4-(3-oxomorpholin-4-yl)phenyl]-(2R,4R)-1-[(E)-3-(5-chlorofuran-2-yl)acryloyl]-4-hydroxypyrrolidine-2-carboxamide, N-[2-fluoro-4-(3-oxomorpholin-4-yl)phenyl]-(2R,4R)-1-[(E)-3-(5-chlorofuran-2-yl)acryloyl]-4-methoxypyrrolidine-2-carboxamide, N-[2-fluoro-4-(3-oxomorpholin-4-yl)phenyl]-(2R,4R)-1-[(E)-3-(4-chlorophenyl)acryloyl]-4-methoxypyrrolidine-2-carboxamide, N-[2-fluoro-4-(3-oxomorpholin-4-yl)phenyl]-(2R,4R)-1-[(E)-3-(3,4-dichlorophenyl)acryloyl]-4-methoxypyrrolidine-2-carboxamide, N-[2-fluoro-4-(3-oxomorpholin-4-yl)phenyl]-(2R,4R)-1-[(E)-3-(4-chlorophenyl)acryloyl]-4-ethoxypyrrolidine-2-carboxamide, N-[2-fluoro-4-(3-oxomorpholin-4-yl)phenyl]-(2R,4R)-1-[(E)-3-(3,4-dichlorophenyl)acryloyl]-4-ethoxypyrrolidine-2-carboxamide, N-[2-fluoro-4-(3-oxomorpholin-4-yl)phenyl]-(2R,4R)-1-[(E)-3-(5-chlorofuran-2-yl)acryloyl]-4-ethoxypyrrolidine-2-carboxamide, N-[2-fluoro-4-(3-oxomorpholin-4-yl)phenyl]-(2R,4R)-1-[(E)-3-(5-chlorothiophen-2-yl)acryloyl]-4-ethoxypyrrolidine-2-carboxamide, N-[4-(3-oxomorpholin-4-yl)phenyl]-(2R,4R)-1-[(E)-3-1H-imidazol-4-ylacryloyl]-4-ethoxypyrrolidine-2-carboxamide, or a pharmaceutically usable salt or stereoisomer thereof, including mixtures thereof in all ratios.

41. The method according to claim 1, wherein said compound is selected from:

N-[2-fluoro-4-(3-oxomorpholin-4-yl)phenyl]-(2R,4R)-1-[(E)-3-1H-imidazol-4-ylacryloyl]-4-hydroxypyrrolidine-2-carboxamide, N-[2-fluoro-4-(3-oxomorpholin-4-yl)phenyl]-(2R,4R)-1-[(E)-3-1H-imidazol-4-ylacryloyl]-4-methoxypyrrolidine-2-carboxamide, N-[2-fluoro-4-(3-oxomorpholin-4-yl)phenyl]-(2R,4R)-1-[(E)-3-1H-imidazol-4-ylacryloyl]-4-ethoxypyrrolidine-2-carboxamide, N-[2-fluoro-4-(3-oxomorpholin-4-yl)phenyl]-(2R,4R)-1-[(E)-3-pyridin-3-ylacryloyl]-4-hydroxypyrrolidine-2-carboxamide, N-[4-(3-oxomorpholin-4-yl)phenyl]-(2R,4R)-1-[(E)-3-pyridin-3-ylacryloyl]-4-ethoxypyrrolidine-2-carboxamide, N-[2-fluoro-4-(3-oxomorpholin-4-yl)phenyl]-(2R,4R)-1-[(E)-3-pyridin-3-ylacryloyl]-4-methoxypyrrolidine-2-carboxamide, N-[2-fluoro-4-(3-oxomorpholin-4-yl)phenyl]-(2R,4R)-1-[(E)-3-pyridin-3-ylacryloyl]-4-ethoxypyrrolidine-2-carboxamide, N-[4-(3-oxomorpholin-4-yl)phenyl]-(2R,4R)-1-[(E)-3-pyridin-3-ylacryloyl]-4-hydroxypyrrolidine-2-carboxamide, N-[4-(3-oxomorpholin-4-yl)phenyl]-(2R,4R)-1-[(E)-3-pyridin-3-ylacryloyl]-4-methoxypyrrolidine-2-carboxamide, N-[4-(3-oxomorpholin-4-yl)phenyl]-(2R,4R)-1-[(E)-3-pyridin-4-ylacryloyl]-4-hydroxypyrrolidine-2-carboxamide, N-[4-(3-oxomorpholin-4-yl)phenyl]-(2R,4R)-1-[(E)-3-pyridin-4-ylacryloyl]-4-ethoxypyrrolidine-2-carboxamide, N-[4-(3-oxomorpholin-4-yl)phenyl]-(2R,4R)-1-[(E)-3-1H-imidazol-4-ylacryloyl]-4-methoxypyrrolidine-2-carboxamide, or a pharmaceutically usable salt or stereoisomer thereof, including mixtures thereof in all ratios.

42. The method according to claim 1, wherein said compound is selected from:
- N-[4-(3-oxomorpholin-4-yl)phenyl]-(2R,4R)-1-[(E)-3-(4-bromothiophen-2-yl)acryloyl]-4-hydroxypyrrolidine-2-carboxamide,
- N-[4-(3-oxomorpholin-4-yl)phenyl]-(2R,4R)-1-[(E)-3-(4-bromothiophen-2-yl)acryloyl]-4-ethoxypyrrolidine-2-carboxamide,
- N-[4-(3-oxomorpholin-4-yl)phenyl]-(2R,4R)-1-[(E)-3-(5-bromothiophen-2-yl)acryloyl]-4-hydroxypyrrolidine-2-carboxamide,
- N-[4-(3-oxomorpholin-4-yl)phenyl]-(2R,4R)-1-[(E)-3-(5-bromothiophen-2-yl)acryloyl]-4-ethoxypyrrolidine-2-carboxamide,
- 1-N-[(4-chlorophenyl)]-2-N-{[4((R)-2-methyl-3-oxomorpholin-4-yl)phenyl]}-(2R,4R)-4-hydroxypyrrolidine-1,2-dicarboxamide,
- 1-N-[(4-chlorophenyl)]-2-N-{[4((R)-2-methyl-3-oxomorpholin-4-yl)phenyl]}-(2R)-pyrrolidine-1,2-dicarboxamide,
- 1-N-[(4-chlorophenyl)]-2-N-{[4-((R)-2-methyl-3-oxomorpholin-4-yl)phenyl]}-(2R,4R)-4-hydroxypyrrolidine-1,2-dicarboxamide,
- 1-N-[(4-chlorophenyl)]-2-N-{[4-((R)-2-methyl-3-oxomorpholin-4-yl)phenyl]}-(2R)-pyrrolidine-1,2-dicarboxamide,
- 1-N-[(4-chlorophenyl)]-2-N-{[4-(3-oxomorpholin-4-yl)-2-phenoxyphenyl]}-(2R)-pyrrolidine-1,2-dicarboxamide, or a pharmaceutically usable salt or stereoisomer thereof, including mixtures thereof in all ratios.

43. The method according to claim 1, wherein said compound is selected from:
- 1-N-[(4-chlorophenyl)]-2-N-{[2-fluoro-4-((R)-2-methyl-3-oxomorpholin-4-yl)-phenyl]}-(2R,4R)-4-hydroxy-pyrrolidine-1,2-dicarboxamide,
- 1-N-[(4-chlorophenyl)]-3-N-{[4-(3oxomorpholin-4-yl)phenyl]}piperidine-1,3-dicarboxamide,
- 1-N-[(4-chlorophenyl)]-3-N-{[3-methyl-4-(3-oxomorpholin-4-yl)phenyl]}piperidine-1,3-dicarboxamide,
- 1-N-[(4-chlorophenyl)]-2-N-{[4-(3-oxomorpholin-4-yl)phenyl]}-(2R,4R)-4-(2-methoxyethoxy)pyrrolidine-1,2-dicarboxamide,
- 1-N-[(4-chlorophenyl)]-2-N-{[2-methyl-4-(3-oxomorpholin-4-yl)phenyl]}-(2R,4R)-4-hydroxypyrrolidine-1,2-dicarboxamide,
- 1-N-[(4-chlorophenyl)]-2-N-{[4-(3-oxomorpholin-4-yl)phenyl]}-(2R,4R)-4-hydroxypyrrolidine-1,2-dicarboxamide,
- 1-N-[(4-chlorophenyl)]-2-N-{[2-(3-oxomorpholin-4-yl)phenyl]}-(2R,4R)-4-hydroxypyrrolidine-1,2-dicarboxamide, or a pharmaceutically usable salt or stereoisomer thereof, including mixtures thereof in all ratios.

* * * * *